(12) United States Patent
Cowart et al.

(10) Patent No.: US 8,106,088 B2
(45) Date of Patent: Jan. 31, 2012

(54) FUSED BICYCLIC-SUBSTITUTED AMINES AS HISTAMINE-3 RECEPTOR LIGANDS

(75) Inventors: Marlon D. Cowart, Round Lake Beach, IL (US); Yi-Yin Ku, Buffalo Grove, IL (US); Sou-Jen Chang, Prairie View, IL (US); Dilinie P. Fernando, Gurnee, IL (US); Timothy A. Grieme, Chicago, IL (US); Robert J. Altenbach, Chicago, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/847,942

(22) Filed: Jul. 30, 2010

(65) Prior Publication Data
US 2010/0298291 A1 Nov. 25, 2010

Related U.S. Application Data

(62) Division of application No. 12/022,041, filed on Jan. 29, 2008, now Pat. No. 7,807,697, which is a division of application No. 11/357,584, filed on Feb. 16, 2006, now Pat. No. 7,358,263, which is a division of application No. 10/837,162, filed on Apr. 30, 2004, now Pat. No. 7,094,790.

(60) Provisional application No. 60/468,610, filed on May 7, 2003, provisional application No. 60/505,790, filed on Sep. 25, 2003.

(51) Int. Cl.
A61K 31/4025 (2006.01)
A61K 31/404 (2006.01)
C07D 403/06 (2006.01)
C07D 209/04 (2006.01)

(52) U.S. Cl. ......... 514/414; 514/415; 548/469; 548/517

(58) Field of Classification Search .................. None
See application file for complete search history.

(56) References Cited

U.S. PATENT DOCUMENTS

| 5,612,360 | A | 3/1997 | Boyd et al. |
| 6,420,391 | B1 | 7/2002 | Konishi et al. |
| 7,094,790 | B2 * | 8/2006 | Cowart et al. ............. 514/311 |
| 7,358,263 | B2 | 4/2008 | Cowart et al. |
| 7,807,697 | B2 | 10/2010 | Cowart et al. |
| 2004/0224953 | A1 * | 11/2004 | Cowart et al. ............. 514/249 |

FOREIGN PATENT DOCUMENTS

| EP | 754455 A1 | 1/1997 |
| EP | 978512 A1 | 2/2000 |
| ES | 2010142AF | 10/1989 |
| GB | 1178400 A | 1/1970 |
| JP | 200139957 | 2/2001 |
| WO | WO9308179 A1 | 4/1993 |
| WO | WO9408962 A1 | 4/1994 |
| WO | WO9421626 A1 | 9/1994 |
| WO | WO9424105 A1 | 10/1994 |
| WO | WO9718201 A1 | 5/1997 |
| WO | WO9731635 A1 | 9/1997 |
| WO | WO9838156 A1 | 9/1998 |
| WO | WO9857931 A2 | 12/1998 |
| WO | WO9943672 A1 | 9/1999 |
| WO | WO0006254 A2 | 2/2000 |
| WO | WO02074758 A2 | 9/2002 |
| WO | WO2004043458 A1 | 5/2004 |

OTHER PUBLICATIONS

Abreo, et al., "Novel 3-Pyridyl Ethers with Subnanomolar Affinity for Central Neuronal Nicotonic Acetylcholine Receptors," Journal of Medicinal Chemistry, 1996, vol. 39 (4), pp. 817-825.
Airaksinen, et al., "Histamine Neurons in Human Hypothalamus: Anatomy in Normal and Alzheimer Diseased Brains," Neuroscience, 1991, vol. 44 (2), pp. 465-481.
Andres, et al., "A Simple Stereoselective Synthesis of Enantiopure 2-Substituteed Pyrrolidines and Piperidines from Chiral (R)-Phenylglycinol-Derived Bicyclic 1,3-Oxazolidines," European Journal of Organic Chemistry, 2000, pp. 1719-1726.
Arrang, et al., "Auto-inhibition of Brain Histamine Release Mediated by a Novel Class ($H_3$) of Histamine Receptor," Nature, 1983, vol. 302, pp. 832-837.
Arrang, et al., "Highly Potent and Selective Ligands for Histamine $H_3$-Receptors," Nature, 1987, vol. 327, pp. 117-123.
Arrang, et al., "Histamine $H_3$ Receptor Binding Sites in Rat Brain Membranes: Modulations by Guanine Nucleotides and Divalent Cations," European Journal of Pharmacology, 1990, vol. 188, pp. 219-227.
Bjenning, et al., "Peripherally Administered Ciproxifan Elevates Hypothalamic Histamine Levels and Potently Reduces Food Intake in the Sprague Dawley Rat" in: Histamine Research in the New Mellennium, Watanabe T., et al., eds., Elsevier Science, 2001, pp. 449-450.
Cheng, et al., "Relationship Between the Inhibition Constant ($K_I$) and the Concentration of Inhibitor Which Causes 50 Per Cent Inhibition ($I_{.sub.50}$) of An Enzymatic Reaction," Biochemical Pharmacology, 1973, vol. 22, pp. 3099-3108.
Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.
De Almeida, et al., "Memory Facilitation by Histamine," Archives Internationales De Physiologie Et De Biochimie, 1986, vol. 283 (2), pp. 193-198.

(Continued)

Primary Examiner — Yong Chu

(57) ABSTRACT

Compounds of formula (I)

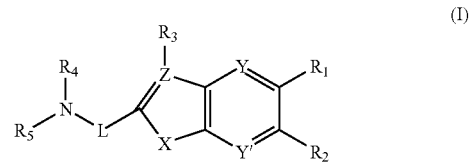

are useful in treating conditions or disorders prevented by or ameliorated by histamine-3 receptor ligands. Also disclosed are pharmaceutical compositions comprising the histamine-3 receptor ligands and methods for using such compounds and compositions.

12 Claims, No Drawings

OTHER PUBLICATIONS

Delaunois, et al., "Modulation of Acetylcholine, Capsaicin and substance P Effects by Histamine $H_3$ Receptors in Isolated Perfused Rabbit Lungs," European Journal of Pharmacology, 1995, vol. 277 (2-3), pp. 243-250.

Dimitriadou, et al., "Functional Relationship Between Mast Cells and C-Sensitive Nerve Fibres Evidenced by Histamine $H_3$-Receptor Modulation in Rat Lung and Spleen," Clinical Science, 1994, vol. 87, pp. 151-163.

Dumery, et al., "Development of Amygdaloid Cholinergic Mediation of Passive Avoidance Learning in the Rat," Experimental Brain Research, 1987, vol. 67(1), pp. 61-69.

Elworthy, et al., "The Configurational Stability of Chiral Lithio α-Amino Carbanions. The Effect of Li-O vs. Li-N Complexation," Tetrahedron, 1994, vol. 50 (20), pp. 6089-6096.

Fitzsimons, et al., "Histamine Receptors Signaling in Epidermal Tumor Cell Lines with H-Ras Gene Alterations," Inflammation Research, 1998, vol. 47 (1), pp. S50-S51.

Fox, et al., "Effects of Histamine $H_3$ Receptor Ligands GT2331 and Ciproxifan in a Repeated Acquisition Response in the Spontaneously Hypertensive Rat Pup," Behavioural Brain Research, 2002, vol. 131 (1-2), pp. 151-161.

Furniss, et al., Vogel's Textbook of Practical Organic Chemistry, 5th Edition, Longman Scientific & Technical, 1989, Table of Contents.

Gaffield, et al., "Chiroptical Properties of N-Nitrosopyrrolidines and N-Nitrosamino Acids," Tetrahedron, 1981, vol. 37, pp. 1861-1869.

Haas, et al., "Subcortical Modulation of Synaptic Plasticity in the Hippocampus," Behavioural Brain Research, 1995, vol. 66 (1-2), pp. 41-44.

Hatta, et al., "Activation of Histamine $H_3$ Receptors Inhibits Carrier-Mediated Norepinephrine Release in a Human Model of Protracted Myocardial Ischennia.sup.1, 2," The Journal of Pharmacology and Experimental Therapeutics, 1997, vol. 283 (2), pp. 494-500.

Higuchi, et al., eds., Pro-drugs as Novels Delivery Systems, vol. 14, ACS Symposium Series, 1975, Table of Contents.

Imamura, et al., "Activation of Histamine $H_3$ -Receptors Inhibits Carrier-Mediated Norepinephrine Release During Protracted Myocardial Ischemia," Circulation Research, 1996, vol. 78 (3), pp. 475-481.

Imamura, et al., "Histamine $H_3$-Receptors-Mediated Inhibition of Calcitonin Gene-Related Peptide Release From Cardiac C Fibers," Circulation Research, 1996, vol. 78 (5), pp. 863-869.

International Search Report for Application No. PCT/US2004/ 013606, mailed on Oct. 11, 2004, 2 pages.

Itoh, et al., "Thioperamide, A Histamine $H_3$ Receptor Antagonist, Powerfully Suppresses Peptide YY-Induced Food Intake in Rats," Biological Psychiatry, 1999, vol. 45 (4), pp. 475-481.

Kamei, et al., "Influence of Certain $H_1$-Blockers on the Step-Through Active Avoidance Response in Rats," Psychopharmacology, 1990, vol. 102 (3), pp. 312-318.

Kamei, et al., "Participation of Histamine in the Step-Through Active Avoidance Response and Its Inhibition by $H_1$-Blockers," Japan Journal of Pharmacology, 1991, vol. 57 (4), pp. 473-482.

Karrer, et al., "Conversion of Optically Active α-Aminocarboxylicacids into Optically Active Amines with Identically Carbon Structures," Helvetica Chimica Acta, 1951, vol. 34, pp. 2202-2210.

Kim, et al., "The Efficient Resolution of Protected Diols and Hydroxy Aldehydes by Lipases: Steric Auxiliary Approach and Synthetic Applications," Bioorganic Medical Chemical Letters, 1996, vol. 6 (1), pp. 71-76.

Leurs, et al., "The Histamine $H_3$ Receptor: A Target for New Drugs," vol. 30, Elsevier Science B.V., 1998, The Table of Contents.

Leurs, et al., "Histamine Homologues Discriminating between Two Functional $H_3$ Receptor Assays. Evidence for $H_3$ Receptor," Journal of Pharmacology and Experimental Therapeutics, 1996, vol. 276 (3), pp. 1009-1015.

Leurs, et al., The Histamine $H_3$-Receptor: A Target for Developing New Drugs, Elsevier Science, 1998, vol. 39, pp. 127-165.

Leurs, et al., "The Medicinal Chemistry and Therapeutic Potentials of Ligands of the Histamine $H_3$ Receptor," Progress in Drug Research, 1995, vol. 45, pp. 107-165.

Leurs, et al., "Therapeutic Potential of Histamine $H_3$-Receptor Agonists and Antagonists," Trends in Pharmacological Sciences, 1998, vol. 19 (5), pp. 177-183.

Levi, et al., "Histamine $H_3$-Receptors: A New Frontier in Myocardial Ischemia," The Journal of Pharmacology and Experimental Therapeutics, 2000, vol. 292 (3), pp. 825-830.

Lin, et al., "Involvement of Histaminergic Neurons in Arousal Mechanisms Demonstrated with $H_3$-Receptor Ligands in the Cat," Brain Research, 1990, vol. 523 (2), pp. 325-330.

Matsubara, et al., "UK-14,304, R(−) .alpha.-Methyl-Histamine and SMS 201-995 Block Plasma Protein Leakage Within Dura Mater by Prejunctional Mechanisms," European Journal of Pharmacology, 1992, vol. 224 (2-3), pp. 145-150.

Mazurkiewicz-Kwilecki, et al., "Changes in the Regional Brain Histamine and Histidine Levels in Postmortem Brains of Alzheimer Patients," Canadian Journal of Physiology and Pharmacology, 1989, vol. 67 (1), pp. 75-78.

McLeod, et al., "Histamine $H_3$ Antagonists," Progress in Respiratory Research, 2001, vol. 31, pp. 133-136.

Monti, et al., "Sleep and Waking During Acute Histamine $H_3$ Agonist BP2.94 or $H_3$ Antagonist Carboperamide (MR 16155) Administration in Rats," Neuropsychopharmacology, 1996, vol. 15 (1), pp. 31-35.

Monti, et al., "Effects of Selective Activation or Blockade of the Histamine $H_3$ Receptor on Sleep and Wakefulness," Journal of Pharmacology, 1991, vol. 205, pp. 283-287.

Murakami, et al., "AQ-0145, A Newly Developed Histamine $H_3$ Antagonist, Decreased Seizure Susceptibility of Electrically Induced Convulsions in Mice," Methods and Findings in Experimental and Clinical Pharmacology, 1995, vol. 17 Suppl C, pp. 70-73.

Nijhuis, et al., "Stereochemical Aspects of the "Tert-Amino Effect." 2. Enantio- and Diastereoselectivity in the Synthesis of Quinolines, Pyrrolo[1,2-a]Quinolines, and [1,4]Oxazino[4,3-a]Quinolines," The Journal of Organic Chemistry, 1989, vol. 54, pp. 209-216.

Nugiel, et al., "Improved P1/P1 Substituents for Cyclic Urea Based HIV-1 Protease Inhibitors: Synthesis, Structure-Activity Relationship, and X-Ray Crystal Structure Analysis," Journal of Medical Chemistry, 1997, vol. 40 (10), pp. 1465-1474.

Onodera, et al., "Neuropharmacology of the Histaminergic Neuron System in the Brain and its Relationship with Behavioral Disorders," Progress in Neurobiology, 1994, vol. 42 (6), pp. 685-702.

Pan, et al., "Histaminergic Ligands Attenuate Barrel Rotation in Rats Following Unilateral Labyrinthectomy," Methods and Findings in Experimental and Clinical Pharmacology, 1998, vol. 20 (9), pp. 771-777.

Panula, et al., "Neuronal Histamine Deficit in Alzheimer's Disease," Neuroscience, 1998, vol. 82 (4), pp. 993-997.

Perez-Garcia, et al., "Effects of Histamine $H_3$ Receptor Ligands in Experimental Models of Anxiety and Depression," Psychopharmacology, 1999, vol. 142 (2), pp. 215-220.

Phillips, et al., "Recent Advances in Histamine $H_3$ Receptor Agents," Annual Reports in Medicinal Chemistry, 1998, vol. 33, pp. 31-40.

Poste, et al., "Lipid Vesicles as Carriers for Introducing Biologically Active Materials into Cells," Methods in Cell Biology, 1976, vol. 14, pp. 33-71.

Roche, Bioreversible Carries in Drug Design Theory and Application, Pergamon Press, 1987, Table of Contents.

Rouleau, et al., "Bioavailability, Antinociceptive and Antiinflammatory Properties of Bp 2-94, A Histamine $H_3$ Receptor Agonist Prodrug," The Journal of Pharmacology and Experimental Therapeutics, 1997, vol. 281 (3), pp. 1085-1094.

Sakai, et al., "Effects of Thioperamide, a Histamine $H_3$ Receptor Antagonist, on Locomotor Activity and Brain Histamine Content in Mast Cell-Deficient Wiwv Mice," Life Sciences, 1991, vol. 48 (25), pp. 2397-2404.

Schwartz, et al., "Histamine", in: Psychopharmacology: The Fourth Generation of Progress, Chapter 35, Bloom F.E., et al., eds., Raven Press, 1995, pp. 397-405.

Schwartz, et al., "Histaminergic Transmission in the Mammalian Brain," Physiological Reviews, 1991, vol. 71 (1), pp. 1-51.

Shaywitz, et al., "Dopaminergic But Not Noradrenergic Mediation of Hyperactivity and Performance Deficits in the Developing Rat Pup," Psychopharmacology, 1984, vol. 82 (1-2), pp. 73-77.

Szelag, "Role of Histamine $H_3$-Receptors in the Proliferation Neoplastic Cells in Vitro," Medical Science Monitor, 1998, vol. 4 (5), pp. 747-755.

Tedford, "Clinical Application of HA $H_3$ Receptor Antagonists in Learning and Memory Disorders", in: The Histamine $H_3$ Receptor, vol. 30, Timmerman H., et al., eds., Elsevier, 1998, pp. 269-286.

Tedford, "Pharmacological Characterization of Gt-2016, A Non-Thiourea-Containing Histamine $H_3$ Antagonist: in Vitro and in Vivo Studies," The Journal of Pharmacology and Experimental Therapeutics, 1995, vol. 275 (2), pp. 598-604.

Tedford, et al., "Cognition and Locomotor Activity in the Developing Rat: Comparisons of Histamine $H_3$ Receptor Antagonists and ADHD Therapeutics," Society for Neuroscience Abstr, vol. 22, pp. 22, 1996.

Wada, et al., "Is the Histaminergic Neuron System a Regulatory Center for Whole-Brain Activity?" Trends in Neurosciences, 1991, vol. 14 (9), pp. 415-418.

Yates, et al., "Effects of a novel histamine $H_3$ receptor antagonist, GT2394, on food intake and weight gain in Sprague-Dawley rats," Society for Neuroscience, vol. 102 (10), pp. 219, 2000.

Yokoyama, et al., "Effect of Thioperamide, a Histamine $H_3$ Receptor Antagonist, on Electrically Induced Convulsions in Mice," Journal of Pharmacology, 1993, vol. 234 (1), pp. 129-133.

Yokoyama, et al., "Histamine and Seizures Implications for the Treatment of Epilepsy," CNS Drugs, 1996, vol. 5 (5), pp. 321-330.

* cited by examiner

FUSED BICYCLIC-SUBSTITUTED AMINES AS HISTAMINE-3 RECEPTOR LIGANDS

This application is a divisional application of U.S. patent application Ser. No. 12/022,041, Jan. 29, 2008, which is a divisional application of U.S. patent application Ser. No. 11/357,584, filed Feb. 16, 2006, and issued as U.S. Pat. No. 7,358,263 on Apr. 15, 2008, which is a divisional application of U.S. patent application Ser. No. 10/837,162, filed Apr. 30, 2004, and issued as U.S. Pat. No. 7,094,790 on Aug. 22, 2006, which claims the benefit of U.S. Provisional Application Ser. No. 60/468,610, filed May 7, 2003, and U.S. Provisional Application Ser. No. 60/505,790, filed Sep. 25, 2003.

BACKGROUND OF THE INVENTION

1. Technical Field

The invention relates to fused bicyclic-substituted amine compounds, compositions comprising such compounds, and methods of treating conditions and disorders using such compounds and compositions.

2. Description of Related Technology

Histamine is a well-known modulator of neuronal activity. At least four types of histamine receptors have been reported in the literature, typically referred to as histamine-1, histamine-2, histamine-3, and histamine-4. The class of histamine receptor known as histamine-3 receptors is believed to play a role in neurotransmission in the central nervous system.

The histamine-3 ($H_3$) receptor was first characterized pharmacologically on histaminergic nerve terminals (Nature, 302: 832-837 (1983)), where it regulates the release of neurotransmitters in both the central nervous system and peripheral organs, particularly the lungs, cardiovascular system and gastrointestinal tract. $H_3$ receptors are thought to be disposed presynaptically on histaminergic nerve endings, and also on neurons possessing other activity, such as adrenergic, cholinergic, serotoninergic, and dopaminergic activity. The existence of $H_3$ receptors has been confirmed by the development of selective $H_3$ receptor agonists and antagonists ((Nature, 327:117-123 (1987); Leurs and Timmerman, ed. "The History of $H_3$ Receptor: a Target for New Drugs," Elsevier (1998)).

The activity at the $H_3$ receptors can be modified or regulated by the administration of $H_3$ receptor ligands. The ligands can exhibit antagonist, agonist, partial agonist, or inverse agonist properties. For example, $H_3$ receptors have been linked to conditions and disorders related to memory and cognition processes, neurological processes, cardiovascular function, and regulation of blood sugar, among other systemic activities. Although various classes of compounds demonstrating $H_3$ receptor-modulating activity exist, it would be beneficial to provide additional compounds demonstrating activity at the $H_3$ receptors that can be incorporated into pharmaceutical compositions useful for therapeutic methods.

SUMMARY OF THE INVENTION

The invention is directed to substituted amines and, more particularly, fused bicyclic-substituted amines. The compounds of the invention have the formula:

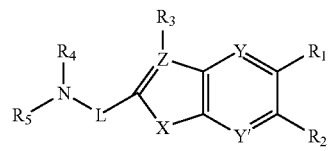

(I)

or a pharmaceutically acceptable salt, ester, amide, or prodrug thereof, wherein:

X is O, S, NH, or N(alkyl);

Y, and Y' are each independently selected from the group consisting of CH, CF, and N;

Z is C or N, provided that when X is O or S, Z is N;

one of $R_1$ and $R_2$ is selected from the group consisting of aryl, heteroaryl, and heterocycle;

the other of $R_1$ and $R_2$ is selected from the group consisting of hydrogen, alkyl, alkoxy, aryl, cycloalkyl, halo, cyano, and thioalkoxy;

$R_3$ is absent when Z is N and, when present, $R_3$ is selected from the group consisting of hydrogen, methyl, alkoxy, halo, and cyano;

$R_4$ and $R_5$ are each independently selected from the group consisting of alkyl, haloalkyl, hydroxyalkyl, alkoxyalkyl, cycloalkyl, and cycloalkylalkyl, or $R_4$ and $R_5$ taken together with the nitrogen atom to which each is attached form a non-aromatic ring of the structure (a):

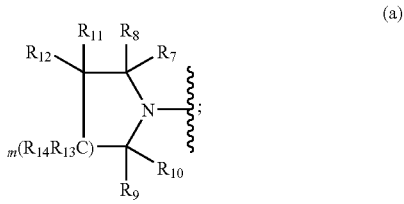

(a)

$R_7$, $R_8$, $R_9$, and $R_{10}$ are each independently selected from the group consisting of hydrogen, hydroxyalkyl, fluoroalkyl, and alkyl; or one of the pair $R_7$ and $R_8$ or the pair $R_9$ and $R_{10}$ is taken together to form a $C_3$-$C_6$ ring, wherein 0, 1, or 2 heteroatoms selected from O, N, or S replace a carbon atom in the ring;

$R_{11}$ and $R_{12}$ are each independently selected from the group consisting of hydrogen, hydroxy, hydroxyalkyl, alkyl, and fluoro;

$R_{13}$ and $R_{14}$ at each occurrence are independently selected from the group consisting of hydrogen, alkyl, and fluoro;

L is —$[C(R_{15})(R_{16})]_n$—;

$R_{15}$ and $R_{16}$ at each occurrence are independently selected from the group consisting of hydrogen, alkyl, alkoxy, and fluoro;

m is an integer from 0-3; and n is an integer from 2-3.

Another aspect of the invention relates to pharmaceutical compositions comprising compounds of the invention. Such compositions can be administered in accordance with a method of the invention, typically as part of a therapeutic regimen for treatment or prevention of conditions and disorders related to $H_3$ receptor activity.

Yet another aspect of the invention relates to a method of selectively modulating $H_3$ receptor activity. The method is useful for treating and/or preventing conditions and disorders related to $H_3$ receptor modulation in mammals. More particularly, the method is useful for conditions and disorders related to memory and cognition processes, neurological processes, cardiovascular function, and body weight.

The compounds, compositions comprising the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "acyl" as used herein, means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein, means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein, means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido" as used herein, means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein, means a —$NH_2$ group.

The term "aryl" as used herein, means a monocyclic or bicyclic aromatic ring system. Representative examples of aryl include, but are not limited to, phenyl and naphthyl.

The aryl groups of this invention are substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, formyl, haloalkoxy, haloalkyl, halo, hydroxy, hydroxyalkyl, mercapto, nitro, thioalkoxy, —$NR_AR_B$, and ($NR_AR_B$)sulfonyl.

The term "carbonyl" as used herein, means a —C(O)— group.

The term "carboxy" as used herein, means a —$CO_2H$ group, which may be protected as an ester group —$CO_2$-alkyl.

The term "cyano" as used herein, means a —CN group.

The term "cycloalkyl" as used herein, means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The cycloalkyl groups of the invention are substituted with 0, 1, 2, 3, or 4 substituents selected from acyl, acyloxy, alkenyl, alkoxy, alkoxyalkoxy, alkoxyalkyl, alkoxycarbonyl, alkoxyimino, alkyl, alkynyl, amido, carboxy, cyano, ethylenedioxy, formyl, haloalkoxy, haloalkyl, halo, hydroxy, hydroxyalkyl, methylenedioxy, thioalkoxy, and —$NR_AR_B$.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "ethylenedioxy" as used herein, means a —$O(CH_2)_2O$— group wherein the oxygen atoms of the ethylenedioxy group are attached to the parent molecular moiety through one carbon atom forming a five-membered ring or the oxygen atoms of the ethylenedioxy group are attached to the parent molecular moiety through two adjacent carbon atoms forming a six-membered ring.

The term "fluoro" as used herein means —F.

The term "fluoroalkyl" as used herein, means at least one fluoro group, as defined herein, appended to the parent molecular moiety through an alkyl group, as defined herein. Representative example of fluoroalkyl include, but are not limited to, fluoromethyl, difluoromethyl, trifluoromethyl, pentafluoroethyl, and 2,2,2-trifluoroethyl.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, refers to an aromatic five- or six-membered ring wherein 1, 2, 3, or 4 heteroatoms are independently selected from nitrogen, oxygen, or sulfur, or a tautomer thereof. Heteroaryl also refers to fused aromatic ten, eleven- and twelve-membered bicyclic rings containing 1, 2, 3, or 4 heteroatoms independently selected from nitrogen, oxygen, or sulfur, or a tautomer thereof. Examples of such rings include, but are not limited to, a ring wherein one carbon is replaced with an O or S atom; one, two, or three N atoms arranged in a suitable manner to provide an aromatic ring, or a ring wherein two carbon atoms in the ring are replaced with one O or S atom and one N atom. The heteroaryl groups are connected to the parent molecular moiety through a carbon or nitrogen atom. Representative examples of heteroaryl include, but are not limited to, furyl, imidazolyl, isoxazolyl, isothiazolyl, oxadiazolyl, oxazolyl, pyrazinyl, pyrazolyl, pyridazinyl, pyridazinonyl, pyridinyl, pyrimidinyl, pyrrolyl, tetrazolyl, thiadiazolyl, thiazolyl, thienyl, triazinyl, triazolyl, benzothiazolyl, benzofuryl, benzothienyl, isoquinolyl, indolyl, indolizin-2-yl, indazolyl, imidazo[1,2-a]pyridin-2-yl, pyrazolo[1,5-a]pyridin-2-yl, 3-oxo-2H-pyridazin-2-yl, quinolyl, and 2-oxo-1H-pyridin-1-yl.

The heteroaryl groups of the invention are substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, formyl, haloalkoxy, haloalkyl, halo, hydroxy, hydroxyalkyl, mercapto, nitro, thioalkoxy, —NR$_A$R$_B$, and (NR$_A$R$_B$)sulfonyl.

The term "heterocycle," as used herein, refers to a three-, four-, five-, six-, seven-, or eight-membered ring containing one, two, or three heteroatoms independently selected from the group consisting of nitrogen, oxygen, and sulfur. Rings containing at least four members can be saturated or unsaturated. For example, the four- and five-membered ring has zero or one double bond. The six-membered ring has zero, one, or two double bonds. The seven- and eight-membered rings have zero, one, two, or three double bonds. The heterocycle groups of the invention can be attached to the parent molecular moiety through a carbon atom or a nitrogen atom. Representative examples of nitrogen-containing heterocycles include, but are not limited to, azepanyl, azetidinyl, aziridinyl, azocanyl, morpholinyl, piperazinyl, piperidinyl, pyrrolidinyl, pyrrolyl, and thiomorpholinyl. Representative examples of non-nitrogen containing heterocycles include, but are not limited to, tetrahydrofuryl and tetrahydropyranyl. Heterocycles typically comprise a non-aromatic ring, suitable for a ring represented by formula (a) in the claims, as described therein.

The heterocycles of the invention are substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, arylalkyl, arylalkoxycarbonyl, carboxy, cyano, formyl, haloalkoxy, haloalkyl, halo, hydroxy, hydroxyalkyl, mercapto, nitro, oxo, thioalkoxy, —NR$_A$R$_B$, and (NR$_A$R$_B$)sulfonyl.

The term "hydroxy" as used herein means a —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, CH$_2$I$_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "mercapto" as used herein, means a —SH group.

The term "methylenedioxy" as used herein, means a —OCH$_2$O— group wherein the oxygen atoms of the methylenedioxy are attached to the parent molecular moiety through two adjacent carbon atoms.

The term "—NR$_A$R$_B$" as used herein, means two groups, R$_A$ and R$_B$, which are appended to the parent molecular moiety through a nitrogen atom. R$_A$ and R$_B$ are independently selected from hydrogen, alkyl, acyl and formyl. Representative examples of —NR$_A$R$_B$ include, but are not limited to, amino, methylamino, acetylamino, and acetylmethylamino.

The term "(NR$_A$R$_B$)sulfonyl" as used herein, means a —NR$_A$R$_B$ group, as defined herein, appended to the parent molecular moiety through a sulfonyl group, as defined herein. Representative examples of (NR$_A$R$_B$)sulfonyl include, but are not limited to, aminosulfonyl, (methylamino)sulfonyl, (dimethylamino)sulfonyl and (ethylmethylamino)sulfonyl.

The term "sulfonyl" as used herein means a —S(O)$_2$— group.

The term "thioalkoxy" as used herein means an alkyl group, as defined herein, appended to the parent molecular moiety through a sulfur atom. Representative examples of thioalkoxy include, but are no limited to, methylthio, ethylthio, and propylthio.

As used herein, the term "antagonist" encompasses and describes compounds that prevent receptor activation by an H$_3$ receptor agonist alone, such as histamine, and also encompasses compounds known as "inverse agonists". Inverse agonists are compounds that not only prevent receptor activation by an H$_3$ receptor agonist, such as histamine, but inhibit intrinsic receptor activity.

Compounds of the Invention

Compounds of the invention can have the general formula (I) as described above.

Typically, one of $R_1$ and $R_2$ is selected from aryl and heteroaryl and the other of $R_1$ and $R_2$ is selected from the group consisting of hydrogen, alkyl, alkoxy, aryl, cycloalkyl, halo, cyano, and thioalkoxy, independent of the substituents at other defined positions. Preferably, $R_1$ is aryl or heteroaryl and, more particularly, $R_1$ is heteroaryl. Examples of specific substituents for $R_1$ and $R_2$ from which each is independently selected include, but are not limited to, furyl, imidazolyl, isoxazolyl, isothiazolyl, oxadiazolyl, oxazolyl, nicotinyl, phenyl, pyrazinyl, pyrazolyl, pyridazinyl, pyridazinonyl, pyridinyl, pyrimidinyl, pyrrolyl, tetrazolyl, thiadiazolyl, thiazolyl, thienyl, triazinyl, triazolyl, azepanyl, azetidinyl, aziridinyl, azocanyl, morpholinyl, piperazinyl, piperidinyl, pyrrolidinyl, pyrrolyl, thiomorpholinyl, tetrahydrofuryl, and tetrahydropyranyl, benzothienyl, isoquinolyl, indolyl, indolizin-2-yl, indazolyl, imidazo[1,2-a]pyridin-2-yl, pyrazolo[1,5-a]pyridin-2-yl, 3-oxo-2H-pyridazin-2-yl, quinolyl, and 2-oxo-1H-pyridin-1-yl. More particularly, $R_1$ and $R_2$ each can be substituted phenyl, unsubstituted phenyl, substituted pyridine, and unsubstituted pyridine. Groups for $R_1$ and $R_2$, and particularly $R_1$, include but are not limited to, cyanophenyl, chlorophenyl, fluorophenyl, nicotinyl, pyridinyl, and quinolyl.

$R_3$ is absent when Z is N. When $R_3$ is present, it is selected from the group consisting of hydrogen, methyl, alkoxy, halo, and cyano, irrespective of the substituents at other positions. Preferably, $R_3$ is hydrogen or methyl.

$R_4$ and $R_5$ can each independently selected from the group consisting of alkyl, haloalkyl, hydroxyalkyl, alkoxyalkyl, cycloalkyl, and cycloalkylalkyl. More specifically, $R_4$ and $R_5$ can be independently selected from methyl, ethyl, and isopropyl. Also, $R_4$ and $R_5$ can be taken together with the nitrogen atom to which each is attached to form a non-aromatic ring of the structure (a), shown above in the Summary of the Invention. Preferably, $R_4$ and $R_5$ taken together with the nitrogen atom to which each is attached form a 4- to 7-membered non-aromatic ring represented by formula (a). More particularly, it is preferred that the 4- to 7-membered non-aromatic ring is selected from the group consisting of azepanyl, pyrrolidinyl, and piperidinyl. More specific examples are those wherein the 4- to 7-membered non-aromatic ring is selected from the group consisting of methylpyrrolidinyl, ethylpyrrolidinyl, dimethylaminopyrrolidinyl, isopropylpyrrolidinyl, isobutylpyrrolidinyl, hydroxymethylpyrrolidinyl, and fluoromethylpyrrolidinyl.

The substituents $R_7$, $R_8$, $R_9$, and $R_{10}$ are each independently selected from the group consisting of hydrogen, hydroxyalkyl, fluoroalkyl, and alkyl. One particular embodiment contemplated includes that wherein at least one substituent represented by $R_7$, $R_8$, $R_9$, and $R_{10}$ is selected from the group consisting of alkyl, halo, fluoroalkyl, and hydroxyalkyl. Alternatively, one of the pair $R_7$ and $R_8$ or the pair $R_9$ and $R_{10}$ is taken together to form a $C_3$-$C_6$ ring, wherein 0, 1, or 2 heteroatoms selected from O, N, or S replace a carbon atom in the ring.

Another embodiment includes at least one substituent represented by $R_7$, $R_8$, $R_9$, and $R_{10}$ is hydroxyalkyl, fluoroalkyl, or alkyl.

Yet another embodiment includes one substituent represented by $R_7$, $R_8$, $R_9$, and $R_{10}$ is methyl, ethyl, fluoromethyl, or hydroxymethyl.

Yet another embodiment includes one substituent represented by $R_7$, $R_8$, $R_9$, and $R_{10}$ is alkyl and the other three substituents are hydrogen.

$R_{11}$ and $R_{12}$ are each independently selected from the group consisting of hydrogen, hydroxy, hydroxyalkyl, alkyl, and fluoro, irrespective of the substituents at other positions.

$R_{13}$ and $R_{14}$ at each occurrence are independently selected from the group consisting of hydrogen, alkyl, and fluoro, irrespective of the substituents at other positions. For a more particular example, $R_{13}$ and $R_{14}$ at each occurrence are each independently selected from the group consisting of hydrogen and alkyl.

One specific embodiment contemplated includes that wherein $R_{11}$, $R_{12}$, $R_{13}$, and $R_{14}$ are each hydrogen.

L is a group of the formula —[C($R_{15}$)($R_{16}$)]$_n$—. More particularly, L can be selected from the group consisting of —CH$_2$CH$_2$— or —CH$_2$CH$_2$CH$_2$—.

$R_{15}$ and $R_{16}$ at each occurrence are independently selected from the group consisting of hydrogen, alkyl, alkoxy, and fluoro. Preferably, $R_{15}$ and $R_{16}$ are each hydrogen.

The variable "m" represents an number from 0-3. Preferably, the integer is 0, 1, or 2.

The variable "n" is an integer from 2-3. Preferably, the integer is 2.

X is O, S, —NH—, or —N(alkyl)-.

Y and Y' are each independently CH, CF, or N.

Z is C or N, provided that when X is O or S, Z is N. Also, when Z is N, $R_3$ is absent.

Specific embodiments contemplated include, but are not limited to, compounds of formula (I), as defined, wherein:
  X is O and Z is N;
  X is —NH— or —N(alkyl)- and Z is C;
  X is —NH— or —N(alkyl)- and Z is N; and
  X is S and Z is N.

In addition, compounds of formula (I) include those wherein $R_1$ is heteroaryl; $R_2$ and $R_3$ are hydrogen; L is —CH$_2$CH$_2$—; m is 1; and $R_4$ and $R_5$ are taken together to form a pyrrolidinyl ring of formula (a), wherein one of $R_7$, $R_8$, $R_9$, and $R_{10}$ is methyl and the remaining three substituents are hydrogen, particularly where X is O or S and Z is N.

Specific examples of compounds of the invention include, but are not limited to:
  4-{2-[2-(2-methyl-pyrrolidin-1-yl)-ethyl]-benzooxazol-5-yl}-benzonitrile;
  4-{2-[2-(2-(R)-methyl-pyrrolidin-1-yl)-ethyl]-benzooxazol-5-yl}-benzonitrile;
  4-[2-(2-Pyrrolidin-1-yl-ethyl)-benzooxazol-5-yl]-benzonitrile;
  4-{2-[2-(2-(S)-methyl-pyrrolidin-1-yl)-ethyl]-benzooxazol-5-yl}-benzonitrile;
  4-{2-[2-(3-(R)-Hydroxy-pyrrolidin-1-yl)-ethyl]-benzooxazol-5-yl}-benzonitrile;
  4-{2-[2-(2-(S)-Hydroxymethyl-pyrrolidin-1-yl)-ethyl]-benzooxazol-5-yl}-benzonitrile;
  4-{2-[2-(2-(R),5-(R)-Dimethyl-pyrrolidin-1-yl)-ethyl]-benzooxazol-5-yl}-benzonitrile;
  4-[2-(2-Piperidin-1-yl-ethyl)-benzooxazol-5-yl]-benzonitrile;
  4-{2-[2-(2-(R)-methyl-piperidin-1-yl)-ethyl]-benzooxazol-5-yl}-benzonitrile;
  4-{2-[2-(2-(S)-Methoxymethyl-pyrrolidin-1-yl)-ethyl]-benzooxazol-5-yl}-benzonitrile;
  4-[2-(2-Azepan-1-yl-ethyl)benzooxazol-5-yl]-benzonitrile;
  4-[2-(2-Diethylamino-ethyl)-benzooxazol-5-yl]-benzonitrile;
  4-{2-[2-(Isopropyl-methyl-amino)-ethyl]-benzooxazol-5-yl}-benzonitrile;
  4-{2-[2-(tert-Butyl-methyl-amino)-ethyl]-benzooxazol-5-yl}-benzonitrile;

4-{2-[2-(Butyl-methyl-amino)-ethyl]-benzooxazol-5-yl}-benzonitrile;
4-{2-[2-(2-Hydroxymethyl-piperidin-1-yl)-ethyl]-benzooxazol-5-yl}-benzonitrile;
4-(2-[2-[2-(2-Hydroxy-ethyl)-piperidin-1-yl]-ethyl]-benzooxazol-5-yl)-benzonitrile;
4-{2-[2-(2-Isopropyl-pyrrolidin-1-yl)-ethyl]-benzooxazol-5-yl}-benzonitrile;
4-{2-[2-(2-(R)-Methyl-azetidin-1-yl)-ethyl]-benzooxazol-5-yl}-benzonitrile;
4-{2-[2-(2-(S)-Fluoromethyl-azetidin-1-yl)-ethyl]-benzooxazol-5-yl}-benzonitrile;
4-{2-[2-(2-(S)-Hydroxymethyl-azetidin-1-yl)-ethyl]-benzooxazol-5-yl}-benzonitrile;
4-[2-(2-Azetidin-1-yl-ethyl)-benzooxazol-5-yl]-benzonitrile;
4-(2-{2-[cis-2,6-dimethyl-piperidin-1-yl]-ethyl}-benzooxazol-5-yl)-benzonitrile;
4-(2-{2-[1,4,5,6-tetrahydropyrimidin-1-yl]-ethyl}-benzooxazol-5-yl)-benzonitrile;
4-(2-{2-[ethyl-isopropyl-amino]-ethyl}-benzooxazol-5-yl)-enzonitrile;
4-{2-[2-(2-(2-methyl-propyl)-pyrrolidin-1-yl)-ethyl]-benzooxazol-5-yl}-benzonitrile;
4-{2-[2-(2-(R)-Methyl-pyrrolidin-1-yl)-ethyl]-1H-indol-5-yl}-benzonitrile;
4-{1-Methyl-2-[2-(2-(R)-methyl-pyrrolidin-1-yl)-ethyl]-1H-indol-5-yl}-benzonitrile;
3-{1-Methyl-2-[2-(2-(R)-methyl-pyrrolidin-1-yl)-ethyl]-1H-indol-5-yl}-benzonitrile;
3-{2-[2-(2-(R)-Methyl-pyrrolidin-1-yl)-ethyl]-1H-indol-5-yl}-benzonitrile;
5-(4-Fluoro-phenyl)-2-[2-(2-(R)-methyl-pyrrolidin-1-yl)-ethyl]-1H-indole;
5-(3,5-Difluoro-phenyl)-2-[2-(2-(R)-methyl-pyrrolidin-1-yl)-ethyl]-1H-indole;
2-[2-(2-(R)-Methyl-pyrrolidin-1-yl)-ethyl]-5-(4-trifluoromethoxy-phenyl)-1H-indole;
2-[2-(2-(R)-Methyl-pyrrolidin-1-yl)-ethyl]-5-pyridin-3-yl-1H-indole;
1-(3-{2-[2-(2-(R)-Methyl-pyrrolidin-1-yl)-ethyl]-1H-indol-5-yl}-phenyl)-ethanone;
5-Furan-2-yl-2-[2-(2-(R)-methyl-pyrrolidin-1-yl)-ethyl]-1H-indole;
5-(2,6-Difluoro-pyridin-3-yl)-2-[2-(2-(R)-methyl-pyrrolidin-1-yl)-ethyl]-1H-indole;
5-(6-Methoxy-pyridin-3-yl)-2-[2-(2-(R)-methyl-pyrrolidin-1-yl)-ethyl]-1H-indole;
5-(4-Methanesulfonyl-phenyl)-2-[2-(2-(R)-methyl-pyrrolidin-1-yl)-ethyl]-1H-indole;
5-(2,6-Dimethyl-pyridin-3-yl)-2-[2-(2-(R)-methyl-pyrrolidin-1-yl)-ethyl]-1H-indole;
1-(4-{2-[2-(2-(R)-Methyl-pyrrolidin-1-yl)-ethyl]-1H-indol-5-yl}-phenyl)-ethanone;
5-(3-Fluoro-phenyl)-2-[2-(2-(R)-methyl-pyrrolidin-1-yl)-ethyl]-1H-indole;
Dimethyl-(4-{2-[2-(2-(R)-methyl-pyrrolidin-1-yl)-ethyl]-1H-indol-5-yl}-phenyl)-amine;
5-(4-Chloro-phenyl)-2-[2-(2-(R)-methyl-pyrrolidin-1-yl)-ethyl]-1H-indole;
5-(2,4-Dimethoxy-pyrimidin-5-yl)-2-[2-(2-(R)-methyl-pyrrolidin-1-yl)-ethyl]-1H-indole;
2-[2-(2-(R)-Methyl-pyrrolidin-1-yl)-ethyl]-5-(3-trifluoromethyl-phenyl)-1H-indole;
2-Methyl-5-{2-[2-(2-(R)-methyl-pyrrolidin-1-yl)-ethyl]-1H-indol-5-yl}-benzothiazole;
8-{2-[2-(2-(R)-Methyl-pyrrolidin-1-yl)-ethyl]-1H-indol-5-yl}-quinoline;
5-{2-[2-(2-(R)-Methyl-pyrrolidin-1-yl)-ethyl]-1H-indol-5-yl}-nicotinonitrile;
5-(5-Methoxy-pyridin-3-yl)-2-[2-(2-(R)-methyl-pyrrolidin-1-yl)-ethyl]-1H-indole;
5-(6-Fluoro-pyridin-3-yl)-2-[2-(2-(R)-methyl-pyrrolidin-1-yl)-ethyl]-1H-indole;
2-[2-(2-(R)-Methyl-pyrrolidin-1-yl)-ethyl]-5-pyrimidin-5-yl-1H-indole;
1-Methyl-2-[2-(2-(R)-methyl-pyrrolidin-1-yl)-ethyl]-5-pyridin-3-yl-1H-indole;
1-Methyl-2-[2-(2-(R)-methyl-pyrrolidin-1-yl)-ethyl]-5-pyrimidin-5-yl-1H-indole;
5-{1-Methyl-2-[2-(2-(R)-methyl-pyrrolidin-1-yl)-ethyl]-1H-indol-5-yl}-nicotinonitrile;
4-{2-[2-(2-(R)-Methyl-pyrrolidin-1-yl)-ethyl]-1H-benzoimidazol-5-yl}-benzonitrile;
2-[2-(2-(R)-Methyl-pyrrolidin-1-yl)-ethyl]-5-pyridin-3-yl-1H-benzoimidazole;
5-(4-Fluoro-phenyl)-2-[2-(2-(R)-methyl-pyrrolidin-1-yl)-ethyl]-1H-benzoimidazole;
1-(4-{2-[2-(2-(R)-Methyl-pyrrolidin-1-yl)-ethyl]-1H-benzoimidazol-5-yl}-phenyl)-ethanone;
3-{2-[2-(2-(R)-Methyl-pyrrolidin-1-yl)-ethyl]-1H-benzoimidazol-5-yl}-benzonitrile;
1-(3-{2-[2-(2-(R)-Methyl-pyrrolidin-1-yl)-ethyl]-1H-benzoimidazol-5-yl}-phenyl)-ethanone;
5-(3-Methoxy-phenyl)-2-[2-(2-(R)-methyl-pyrrolidin-1-yl)-ethyl]-1H-benzoimidazole;
5-Furan-2-yl-2-[2-(2-(R)-methyl-pyrrolidin-1-yl)-ethyl]-1H-benzoimidazole;
5-(2,6-Difluoro-pyridin-3-yl)-2-[2-(2-(R)-methyl-pyrrolidin-1-yl)-ethyl]-1H-benzoimidazole;
5-(6-Methoxy-pyridin-3-yl)-2-[2-(2-(R)-methyl-pyrrolidin-1-yl)-ethyl]-1H-benzoimidazole;
5-(4-Methanesulfonyl-phenyl)-2-[2-(2-(R)-methyl-pyrrolidin-1-yl)-ethyl]-1H-benzoimidazole;
5-(2,4-Dimethoxy-pyrimidin-5-yl)-2-[2-(2-(R)-methyl-pyrrolidin-1-yl)-ethyl]-1H-benzoimidazole;
5-Benzo[1,3]dioxol-5-yl-2-[2-(2-(R)-methyl-pyrrolidin-1-yl)-ethyl]-1H-benzoimidazole;
5-(5-Methoxy-pyridin-3-yl)-2-[2-(2-(R)-methyl-pyrrolidin-1-yl)-ethyl]-1H-benzoimidazole;
5-(2,6-Dimethyl-pyridin-3-yl)-2-[2-(2-(R)-methyl-pyrrolidin-1-yl)-ethyl]-1H-benzoimidazole;
4-{2-[2-(2-Methyl-pyrrolidin-1-yl)-ethyl]-1H-benzoimidazol-5-yl}-benzoic acid methyl ester;
2-[2-(2-(R)-Methyl-pyrrolidin-1-yl)-ethyl]-5-(4-methylsulfanyl-phenyl)-1H-benzoimidazole;
5-(3,5-Difluoro-phenyl)-2-[2-(2-(R)-methyl-pyrrolidin-1-yl)-ethyl]-1H-benzoimidazole;
2-[2-(2-(R)-Methyl-pyrrolidin-1-yl)-ethyl]-5-pyrimidin-5-yl-1H-benzoimidazole;
8-{2-[2-(2-(R)-Methyl-pyrrolidin-1-yl)ethyl]-1H-benzoimidazol-5-yl}-quinoline;
Dimethyl-(4-{2-[2-(2-(R)-methyl-pyrrolidin-1-yl)-ethyl]-1H-benzoimidazol-5-yl}-phenyl)-amine; and
5-(6-Fluoro-pyridin-3-yl)-2-[2-(2-(R)-methyl-pyrrolidin-1-yl)-ethyl]-1H-benzoimidazole; or a pharmaceutically acceptable salts, esters, amides, and prodrugs thereof.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Methods for Preparing Compounds of the Invention

The compounds of the invention can be better understood in connection with the following synthetic schemes and methods. Such description illustrates a means by which the compounds can be prepared.

As used in the descriptions of the schemes and the examples, certain abbreviations are intended to have the following meanings: Ac for acetyl; AcOH for acetic acid; atm for atmosphere(s); BINAP for 2,2'-bis(diphenylphosphino)-1,1'-binaphthyl; Boc for butyloxycarbonyl; Bu for butyl; Cy for cyclohexyl; $Cy_2PPh_2$ for 2-dicyclohexylphosphino(biphenyl); dba for dibenzylidineacetone; DCM for dichloromethane; DMAP for 4-(N,N-dimethylamino)pyridine; DMF for N,N-dimethylformamide; DMSO for dimethylsulfoxide; dppf for 1,1'-bis(diphenylphosphino)ferrocene; Et for ethyl; EtOH for ethanol; EtOAc for ethyl acetate; HPLC for high pressure liquid chromatography; i-$Pr_2NH$ for isopropylamine; IPA for isopropyl alcohol; IPAC or IPAc for isopropyl acetate; LiTMP and LTMP for lithium 2,2,6,6-tetramethylpiperidide; LDA for lithium diisopropylamide; NBS for N-bromosuccinimide; NIS for N-iodosuccinimide; NMP for N-methyl-2-pyrrolidone; Me for methyl; MeOH for methanol; Ms for methanesulfonyl; MTBE for tert-butyl methyl ether; Pd for palladium; Ph for phenyl; $Ph_3P$ for triphenylphosphine; Ra Ni/C for Raney nickel on carbon; tBu for tert-butyl; TEA for triethylamine; TFA for trifluoroacetic acid; THF for tetrahydrofuran; TMP for 2,2,6',6'-tetramethylpiperidine; and Ts for p-MePhS(O)$_2$—.

The compounds of this invention can be prepared by a variety of synthetic procedures. Representative procedures are shown in, but are not limited to, Schemes 1-6.

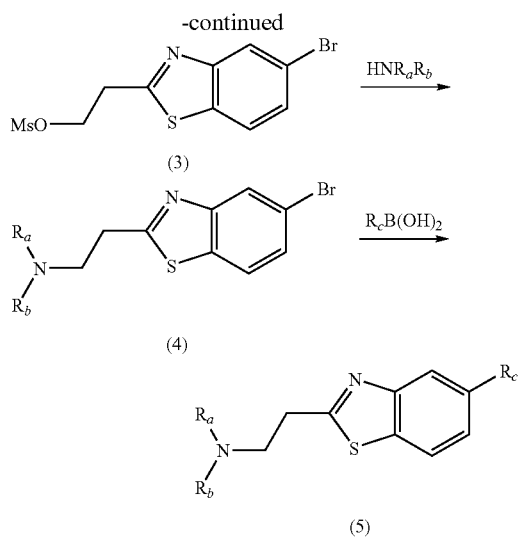

As shown in Scheme 1, compounds of formula (5) can be prepared from 5-bromo-2-methyl-benzothiazole (1). 5-Bromo-2-methyl-benzothiazole (1), Chemical Abstracts number 63837-11-6, is treated with lithium tetra-methyl piperidine followed by paraformaldehyde to provide 2-(5-bromo-benzothiazol-2-yl)-ethanol (2). The hydroxy group of (2) is activated by treatment with mesyl chloride, preferably in the presence of a base, to provide the corresponding methanesulfonic acid 2-(5-bromo-benzothiazol-2-yl)-ethyl ester (3). An amine of formula $HNR_aR_b$ is provided, wherein —$NR_aR_b$ corresponds to groups as defined for —$NR_4R_5$ in the specification, to afford a compound of formula (4). Compound (4) undergoes a Suzuki coupling reaction, wherein $R_cB(OH)_2$ represents a boronic acid where $R_c$ is aryl or heteroaryl, to provide compound (5).

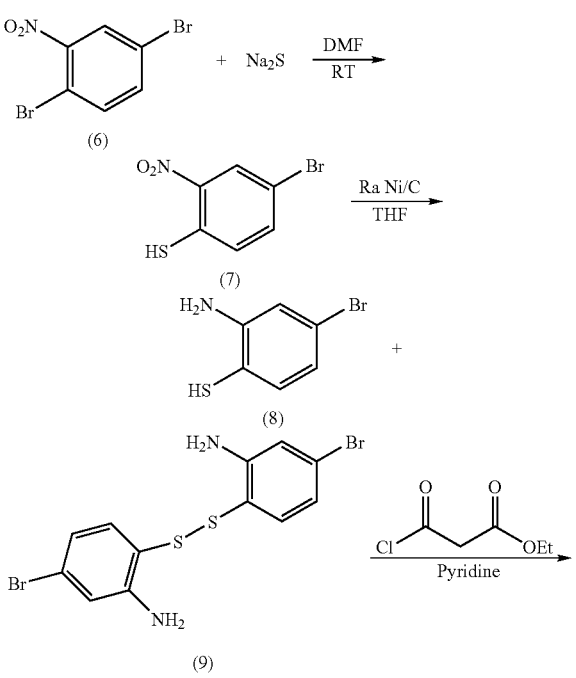

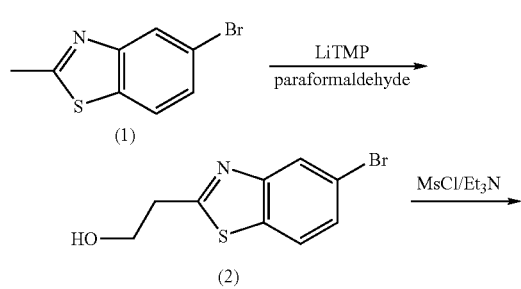

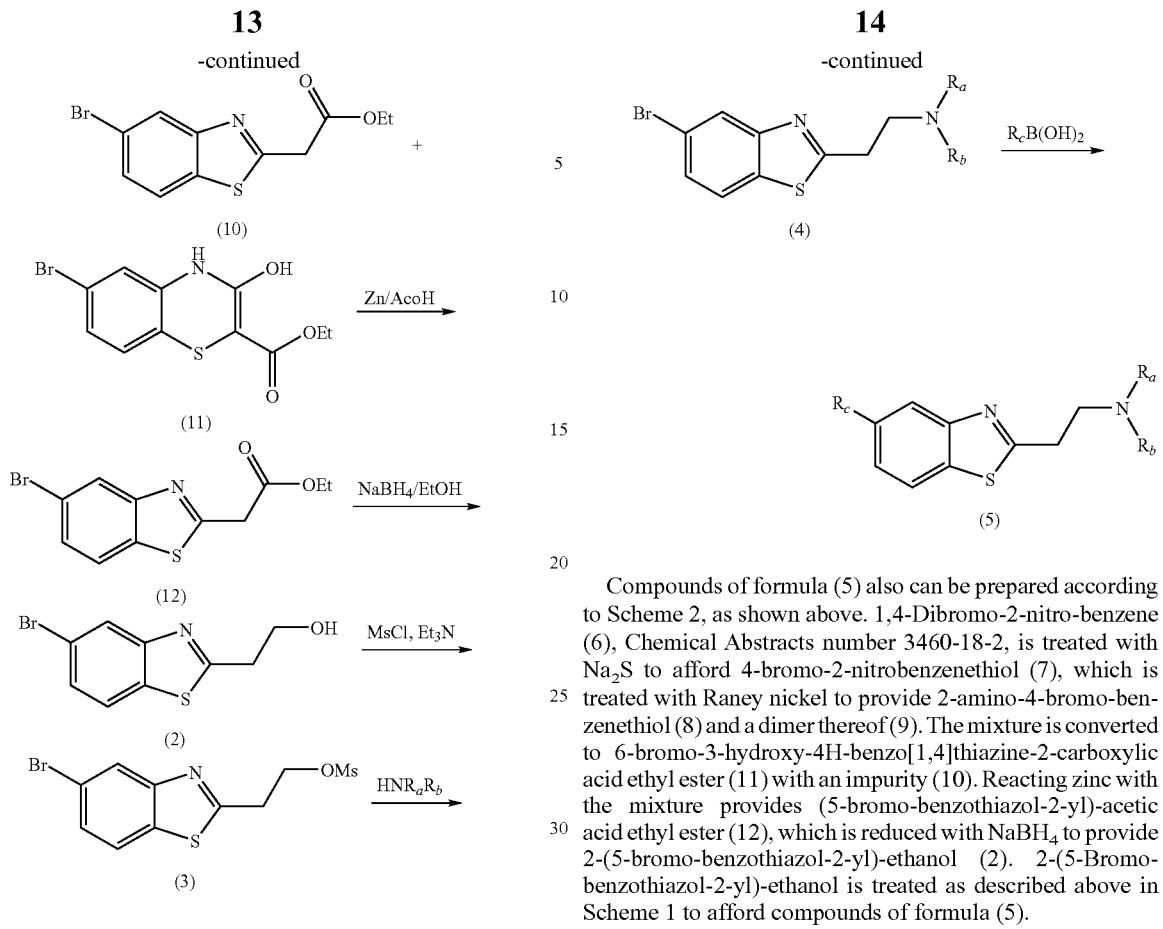

Compounds of formula (5) also can be prepared according to Scheme 2, as shown above. 1,4-Dibromo-2-nitro-benzene (6), Chemical Abstracts number 3460-18-2, is treated with $Na_2S$ to afford 4-bromo-2-nitrobenzenethiol (7), which is treated with Raney nickel to provide 2-amino-4-bromo-benzenethiol (8) and a dimer thereof (9). The mixture is converted to 6-bromo-3-hydroxy-4H-benzo[1,4]thiazine-2-carboxylic acid ethyl ester (11) with an impurity (10). Reacting zinc with the mixture provides (5-bromo-benzothiazol-2-yl)-acetic acid ethyl ester (12), which is reduced with $NaBH_4$ to provide 2-(5-bromo-benzothiazol-2-yl)-ethanol (2). 2-(5-Bromo-benzothiazol-2-yl)-ethanol is treated as described above in Scheme 1 to afford compounds of formula (5).

Scheme 3

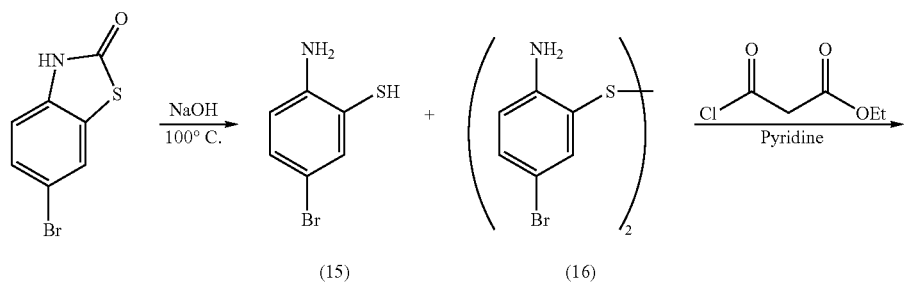

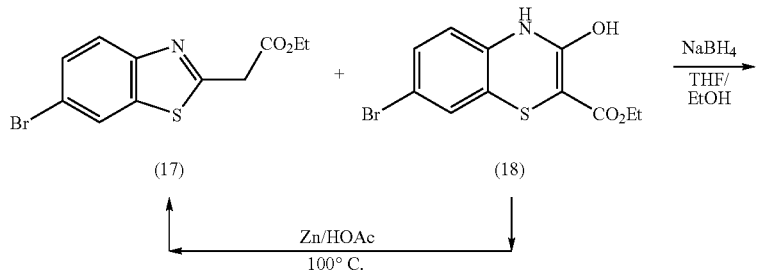

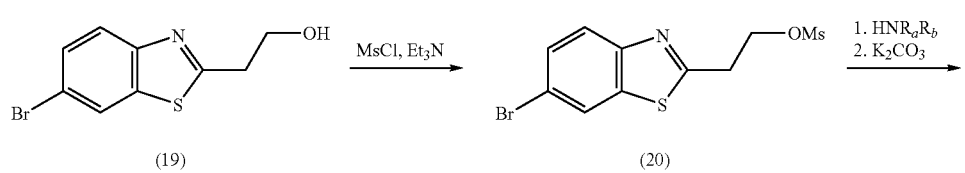

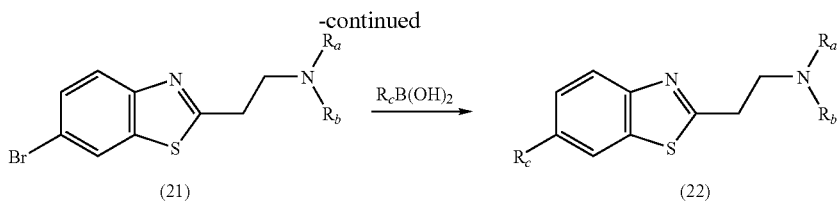

Compounds of formula (22) can be prepared from 6-bromobenzothiazolone as shown in Scheme 3. 6-Bromobenzothiazolone is heated in the presence of NaOH base to provide a mixture of 2-amino-5-bromothiophenol (15) and its disulfide (16). The mixture is treated with chlorocarbonyl-acetic acid ethyl ester to provide 6-bromo-benzothiazol-2-yl-acetic acid ethyl ester (17) and 7-bromo-3-hydroxy-4H-benzo[1,4]thiazine-2-carboxylic acid ethyl ester (18), which can undergo rearrangement by treatment with zinc and ethyl acetate to provide compound (17). Compound (17) is reduced with $NaBH_4$ to provide 2-(6-bromo-benzothiazol-2-yl)-ethanol (19). Compound (19) is treated with mesyl chloride in the presence of triethyl amine to afford the corresponding methanesulfonic acid 2-(6-bromo-benzothiazol-2-yl)-ethyl ester (20), which is treated with an amine of formula $HNR_aR_b$, wherein $R_a$ and $R_b$ each is as defined for $R_4$ and $R_5$, to provide compounds of formula (21). Compounds of formula (21) can be treated with a boronic acid, wherein $R_c$ is aryl or heteroaryl, to provide compounds of formula (22).

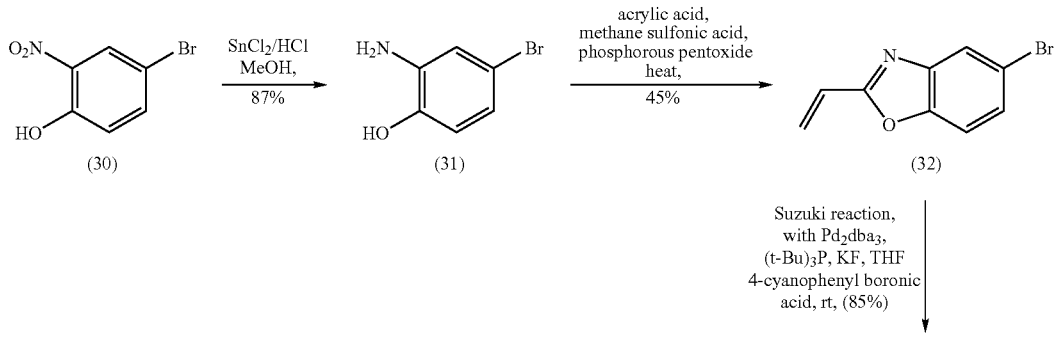

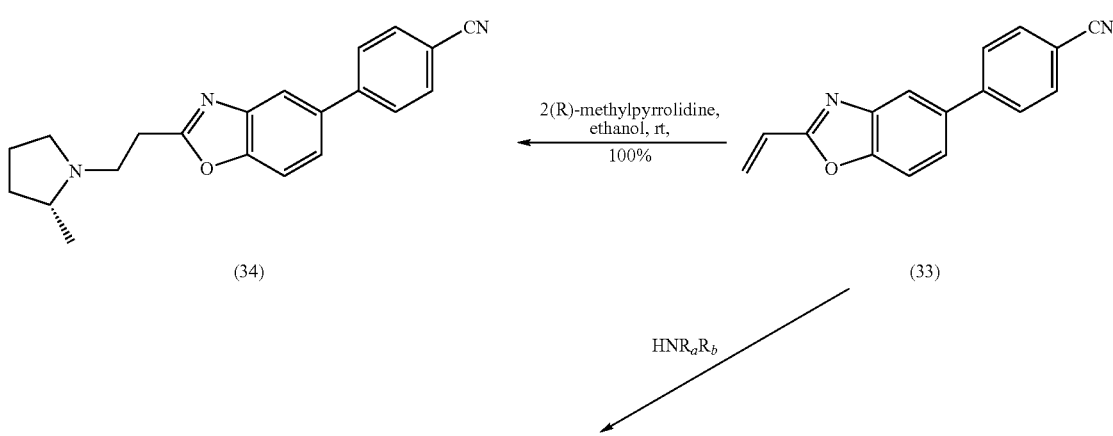

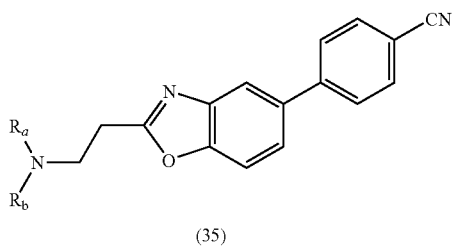

(35)

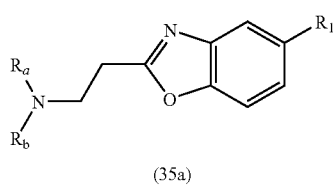

(35a)

Compounds of formula (35) can be prepared from 4-bromo-2-nitro-phenol as shown in Scheme 4, above. 4-Bromo-2-nitro-phenol (30) is reduced to 2-amino-4-bromo-phenol according to methods described in Nugiel, et al., Journal of Medicinal Chemistry 40:1465-1474 (1997) to afford 2-amino-4-bromo-phenol (31). The mixture is heated with methane sulfonic acid and phosphorus pentoxide, followed by acrylic acid, to afford 5-bromo-2-vinyl-benzooxazole (32), which undergoes a Suzuki reaction using 4-cyanophenyl boronic acid to afford a 4-(2-vinyl-benzooxazol-5-yl)-benzonitrile (33). Compound (33) can be treated with an amine $HNR_aR_b$, wherein $R_a$ and $R_b$ are as defined for $R_4$ and $R_5$ to give compounds of formula (35). More particularly, the amine can be 2(R)-methylpyrrolidine, which affords 4-{2-[2-(2-methyl-pyrrolidin-1-yl)-ethyl]-benzooxazol-5-yl}-benzonitrile (34). In addition, the 4-cyanophenylboronic acid can be substituted with other boronic acids of the formula $R_cB(OH)_2$, wherein $R_c$ is aryl, heterocycle, or heteroaryl, to give compounds of general structure (35a) wherein $R_1$ is aryl, heterocycle, or heteroaryl.

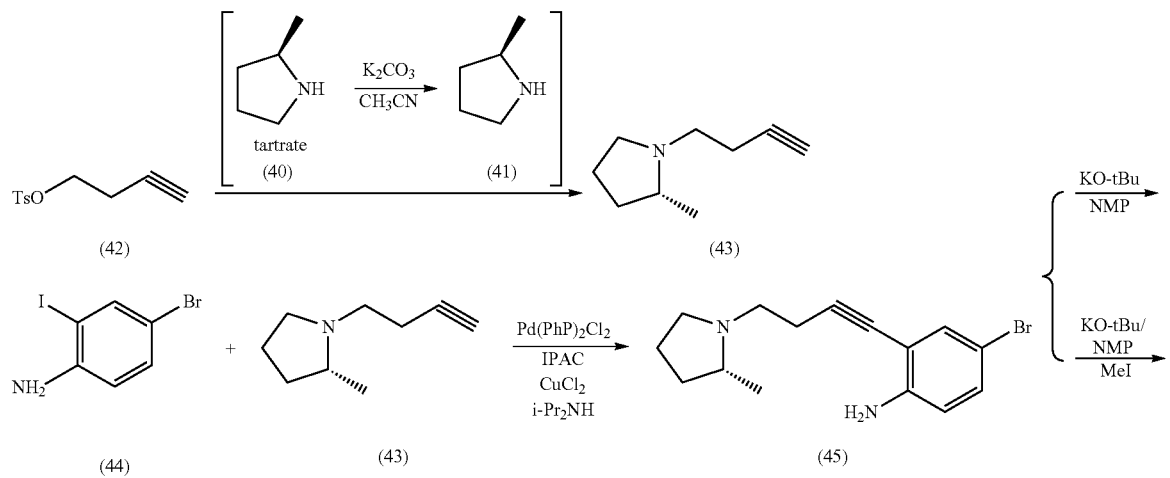

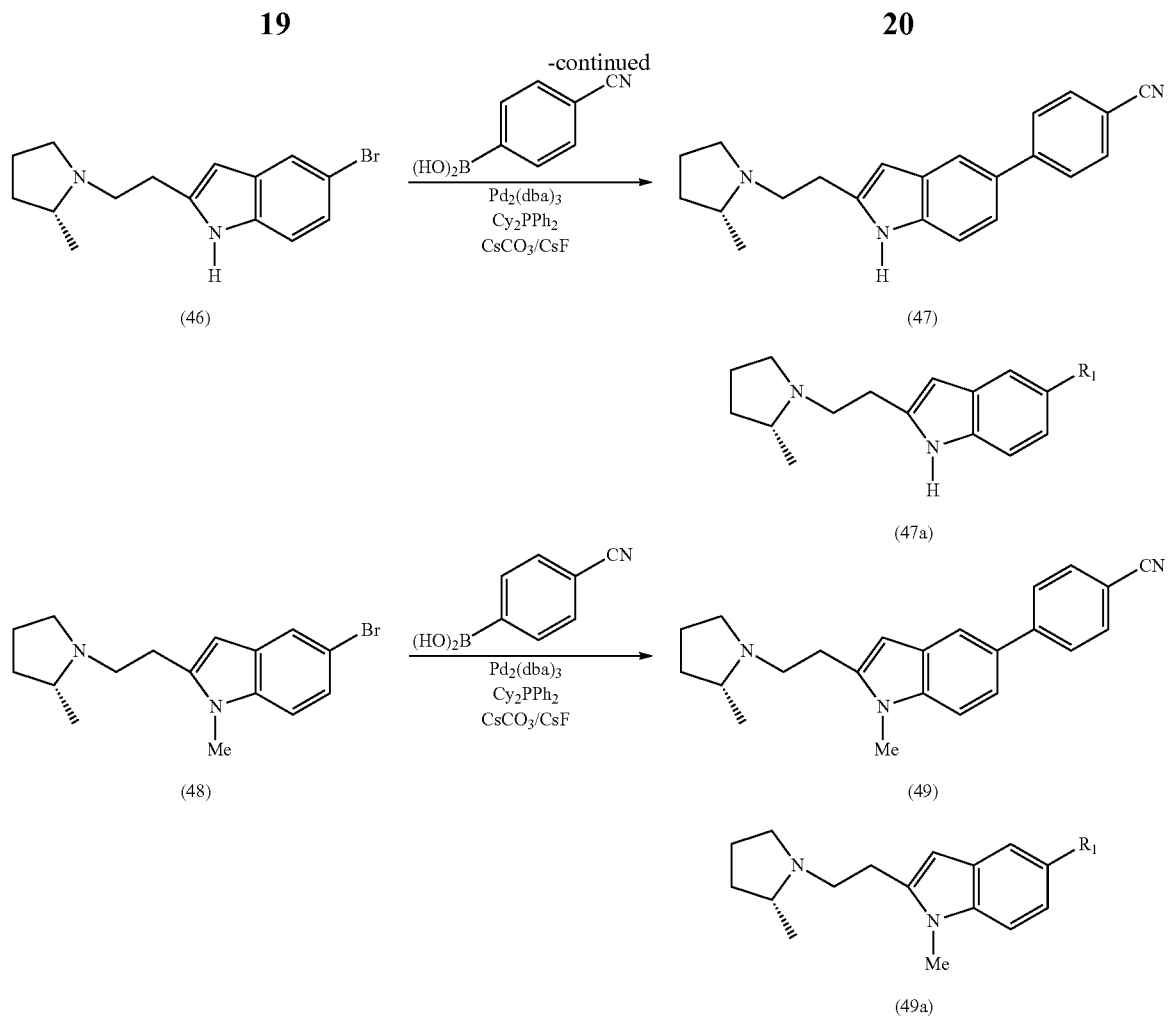

The compound of formula (43) can be prepared from 3-butynyl p-toluenesulfonate (42) and 2(R)-methylpyrrrolidine L-tartrate (40) as shown in Scheme 5. 2(R)-Methylpyrrolidine L-tartrate (40) is treated with potassium carbonate in acetonitrile to provide 2(R)-methylpyrrolidine (41), which is combined with 3-butynyl p-toluenesulfonate (42) to give 1-but-3-ynyl-2-methyl-pyrrolidine (43). Compound (43) is reacted with 4-bromo-2-iodo-phenylamine (44) to provide 4-bromo-2-[4-(2-methyl-pyrrolidin-1-yl)-but-1-ynyl]-phenylamine (45). Compound (45) undergoes cyclization to compound (46) in the presence of a strong base, such as potassium t-butoxide. Compound (46) then is subjected to the Suzuki reaction conditions with an aryl or heteroaryl boronic acid, such as 4-cyanophenylboronic acid, to give compound (47) and (47a). Alternatively, in the presence of base and an alkylating agent, compounds (45) and (46) are alkylated with an alkyl halide such as methyl iodide to give an N-alkyl indole compounds, such as compound (48). Compound formula (48) is then subjected to the Suzuki reaction conditions with an aryl or heteroaryl boronic acid, such as 4-cyanophenylboronic acid, to give compounds such as compound (49) and (49a). Similarly, the compounds (40) and (41) can be substituted with any other suitable amine to provide the corresponding amine-substituted indole compound. In addition, the 4-cyanophenylboronic acid can be substituted with other boronic acids of the formula $R_c B(OH)_2$, wherein $R_c$ is aryl or heteroaryl, to provide compounds of general structures (47a) and (49a), wherein $R_1$ is aryl, heteroaryl, or heterocycle.

Scheme 6

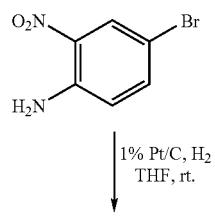

1% Pt/C, $H_2$
THF, rt.

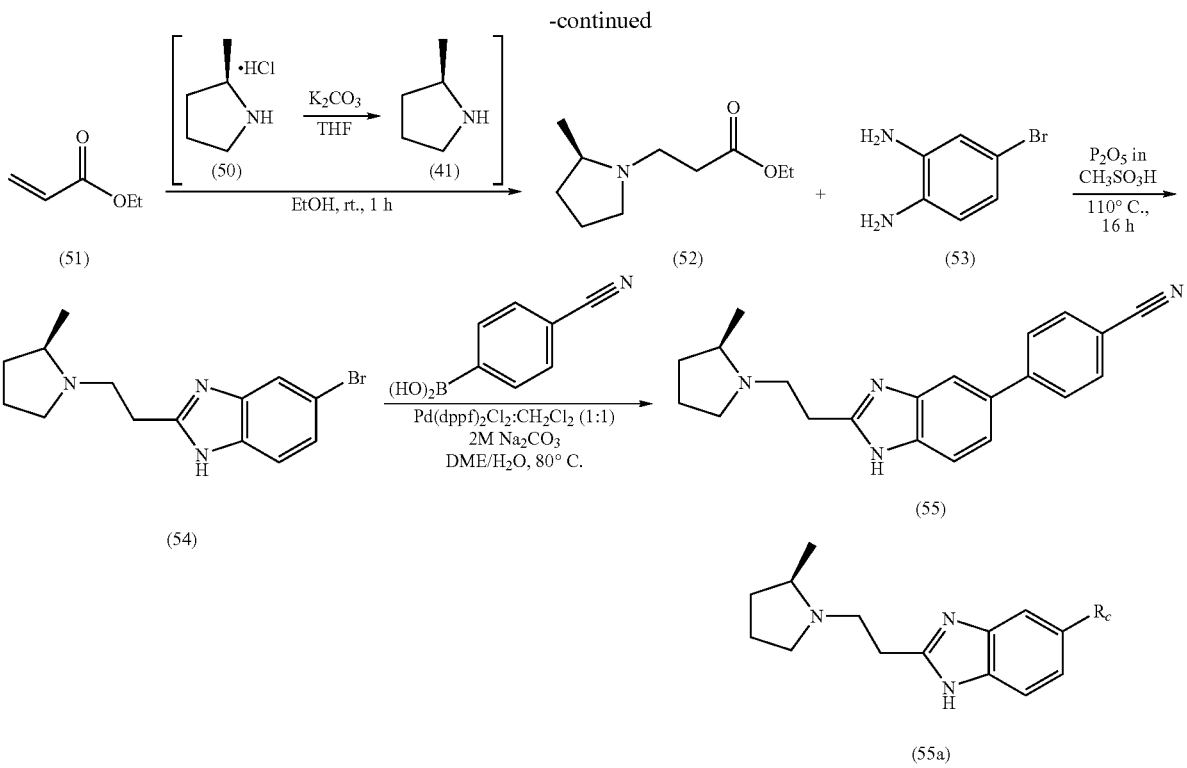

Compounds of formula (55) and (55a) can be prepared from 2(R)-methylpyrrolidine HCl (50) and ethyl acrylate (51) as shown in Scheme 6. 2(R)-Methylpyrrolidine HCl can be treated with potassium carbonate to provide 2(R)-methylpyrrolidine (41), which is reacted with ethyl acrylate (51) to provide 3-(2-methyl-pyrrolidin-1-yl)-propionic acid ethyl ester (52). Compound (52) is reacted with 4-bromo-benzene-1,2-diamine (53), which is produced by controlled hydrogenation of 2-amino-5-bromo-nitrobenzene, Chemical Abstracts number 875-51-4, to provide 5-bromo-2-[2-(2-methyl-pyrrolidin-1-yl)-ethyl]-1H-benzoimidazole (54). Compound (54) can be reacted with a 4-cyanophenylboronic acid to provide 4-{2-[2-(2-methyl-pyrrolidin-1-yl)ethyl]-1H-benzoimidazol-5-yl}-benzonitrile (55). As previously described for Scheme 5, the amine compound (41) can be any amine of the formula $HNR_aR_b$, wherein $R_a$ and $R_b$ are as defined for $R_4$ and $R_5$. Also, the 4-cyanophenylboronic acid can be replaced with any boronic acid of the formula $R_cB(OH)_2$, wherein $R_c$ is aryl or heteroaryl to provide compounds of general structure (55a). Additionally, compounds (55) and (55a) may be alkylated on the benzimidazole nitrogen by treatment with a base, such as cesium carbonate, and an alkylating agent, such as methyl iodide.

Compounds of formula (I), wherein $R_1$ or $R_2$ is halo, particularly bromo, and the remaining substituents are as previously defined for compounds of formula (I), can treated under Negishi coupling conditions. Compounds of formula (I), wherein $R_1$ or $R_2$ is halo, can be reacted with aryl, heteroaryl, or heterocyclic zinc halides, a palladium source such as $Pd(OAc)_2$ or $Pd_2 dba_3$, and a phosphine ligand such as triphenylphosphine, tri-t-butylphosphine, 2-dicyclohexylphosphino(biphenyl) in a solvent, for example THF, typically at 0-150° C.

Alternatively, compounds of formula (I), wherein $R_1$ or $R_2$ is halo, particularly bromo, and the remaining substituents are as previously defined for compounds of formula (I), also can be treated by Stille coupling conditions. The compound of formula (I), wherein $R_1$ or $R_2$ is halo, is reacted with aryl, heteroaryl, or heterocyclic tributylstannane, a palladium source such as $Pd(OAc)_2$ or $Pd_2 dba_3$, and a phosphine ligand such as triphenylphosphine, triphenylarsine, tri(2-furyl)phosphine, or tri-t-butylphosphine, and optionally in the presence of a copper salt such as copper bromide, in a solvent, for example DMF or THF, typically at 0-150° C.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, refer to carboxylate salts, amino acid addition salts, zwitterions, esters and amides of compounds of formula (I) which are, within the scope of sound medical judgement, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgement, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyliodide, benzyl iodide, cyclopentyl iodide. They also may be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgement, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

Methods of the Invention

Compounds and compositions of the invention are useful for modulating the effects of histamine-3 receptors. In particular, the compounds and compositions of the invention can be used for treating and preventing disorders modulated by the histamine-3 receptors. Typically, such disorders can be ameliorated by selectively modulating the histamine-3 receptors in a mammal, preferably by administering a compound or composition of the invention, either alone or in combination with another active agent as part of a therapeutic regimen.

The compounds of the invention, including but not limited to those specified in the examples, possess an affinity for the histamine-3 receptors. As histamine-3 receptor ligands, the compounds of the invention may be useful for the treatment and prevention of diseases or conditions such as acute myocardial infarction, Alzheimer's disease, asthma, attention-deficit hyperactivity disorder, bipolar disorder, cognitive enhancement, cognitive deficits in psychiatric disorders, deficits of memory, deficits of learning, dementia, cutaneous carcinoma, drug abuse, diabetes, type II diabetes, depression, epilepsy, gastrointestinal disorders, inflammation, insulin resistance syndrome, jet lag, medullary thyroid carcinoma, melanoma, Meniere's disease, metabolic syndrome, mild cognitive impairment, migraine, mood and attention alteration, motion sickness, narcolepsy, neurogenic inflammation, obesity, obsessive compulsive disorder, pain, Parkinson's disease, polycystic ovary syndrome, schizophrenia, seizures, septic shock, Syndrome X, Tourette's syndrome, vertigo, and wakefulness.

The ability of the compounds of the invention, including, but not limited to, those specified in the examples, to treat septic shock and cardiovascular disorders, in particular, acute myocardial infarction may be demonstrated by Imamura et al., Circ. Res., 78:475-481 (1996); Imamura et. al., Circ. Res., 78:863-869 (1996); R. Levi and N.C.E. Smith, "Histamine $H_3$-receptors: A new frontier in myocardial ischemia", J. Pharm. Exp. Ther., 292:825-830 (2000); and Hatta, E., K. Yasuda and R. Levi, "Activation of histamine $H_3$ receptors inhibits carrier-mediated norepinephrine release in a human model of protracted myocradial ischemia", J. Pharm. Exp. Ther., 283:494-500 (1997).

The ability of the compounds of the invention, including, but not limited to, those specified in the examples, to treat sleep disorders, in particular, narcolepsy may be demonstrated by Lin et al., Brain Res., 523:325-330 (1990); Monti, et al., Neuropsychopharmacology 15:31-35 (1996); Sakai, et al., Life Sci., 48:2397-2404 (1991); Mazurkiewicz-Kwilecki and Nsonwah, Can. J. Physiol. Pharmacol., 67:75-78 (1989); P. Panula, et al., Neuroscience 44:465-481 (1998); Wada, et al., Trends in Neuroscience 14:415 (1991); and Monti, et al., Eur. J. Pharmacol. 205:283 (1991).

The ability of the compounds of the invention, including, but not limited to, those specified in the examples, to treat cognition and memory process disorders may be demonstrated by Mazurkiewicz-Kwilecki and Nsonwah, Can. J. Physiol. Pharmacol., 67:75-78 (1989); P. Panula, et al., Neuroscience, 82:993-997 (1997); Haas, et al., Behay. Brain Res., 66:41-44 (1995); De Almeida and Izquierdo, Arch. Int. Pharmacodyn., 283:193-198 (1986); Kamei et al., Psychopharmacology, 102:312-318 (1990); Kamei and Sakata, Jpn. J. Pharmacol., 57:437-482 (1991); Schwartz et al., Psychopharmacology, The fourth Generation of Progress. Bloom and Kupfer (eds). Raven Press, New York, (1995) 397; and Wada, et al., Trends in Neurosci., 14:415 (1991).

The ability of the compounds of the invention, including, but not limited to, those specified in the examples, to treat attention-deficit hyperactivity disorder (ADHD) may be demonstrated by Shaywitz et al., Psychopharmacology, 82:73-77 (1984); Dumery and Blozovski, Exp. Brain Res., 67:61-69 (1987); Tedford et al., J. Pharmacol. Exp. Ther., 275:598-604 (1995); Tedford et al., Soc. Neurosci. Abstr., 22:22 (1996); and Fox, et al., Behav. Brain Res., 131:151-161 (2002).

The ability of the compounds of the invention, including, but not limited to, those specified in the examples, to treat seizures, in particular, epilepsy may be demonstrated by Yokoyama, et al., Eur. J. Pharmacol., 234:129 (1993); Yokoyama and Iinuma, CNS Drugs 5:321 (1996); Onodera et al., Prog. Neurobiol., 42:685 (1994); R. Leurs, R. C. Vollinga and H. Timmerman, "The medicinal chemistry and therapeutic potential of ligands of the histamine $H_3$ receptor", Progress in Drug Research 45:170-165, (1995); Leurs and Timmerman, Prog. Drug Res., 39:127 (1992); The Histamine $H_3$ Receptor, Leurs and Timmerman (eds), Elsevier Science, Amsterdam, The Netherlands (1998); H. Yokoyama and K. Iinuma, "Histamine and Seizures: Implications for the treatment of epilepsy", CNS Drugs, 5(5):321-330 (1995); and K. Hurukami, H. Yokoyama, K. Onodera, K. Iinuma and T. Watanabe, "AQ-0145, A newly developed histamine $H_3$ antagonist, decreased seizure susceptibility of electrically induced convulsions in mice", Meth. Find. Exp. Clin. Pharmacol., 17(C):70-73 (1995).

The ability of the compounds of the invention, including, but not limited to, those specified in the examples, to treat motion sickness, Alzheimer's disease, and Parkinson's disease may be demonstrated by Onodera, et al., Prog. Neurobiol., 42:685 (1994); Leurs and Timmerman, Prog. Drug Res., 39:127 (1992); and The Histamine $H_3$ Receptor, Leurs and Timmerman (eds), Elsevier Science, Amsterdam, The Netherlands (1998).

The ability of the compounds of the invention, including, but not limited to, those specified in the examples, to treat narcolepsy, schizophrenia, depression, and dementia may be demonstrated by R. Leurs, R.C. Vollinga and H. Timmerman, "The medicinal chemistry and therapeutic potential of ligands of the histamine $H_3$ receptor", Progress in Drug Research 45:170-165 (1995); The Histamine $H_3$ Receptor, Leurs and Timmerman (eds), Elsevier Science, Amsterdam, The Netherlands (1998); and Perez-Garcia C, et. al., and Psychopharmacology (Berl) 142(2):215-20 (February, 1999).

The ability of the compounds of the invention, including, but not limited to, those specified in the examples, to treat wakefulness, cognitive enhancement, mood and attention alteration, vertigo and motion sickness, and treatment of cognitive deficits in psychiatric disorders may be demonstrated by Schwartz, Physiol. Review 71:1-51 (1991).

The ability of the compounds of the invention, including, but not limited to, those specified in the examples, to treat mild cognitive impairment, deficits of memory, deficits of learning and dementia may be demonstrated by C. E. Tedford, in "The Histamine $H_3$ Receptor: a target for new drugs", the Pharmacochemistry Library, vol. 30 (1998) edited by R. Leurs and H. Timmerman, Elsevier (New York). p. 269 and references also contained therein.

The ability of the compounds of the invention, including, but not limited to, those specified in the examples, to treat obesity may be demonstrated by Leurs, et al., Trends in Pharm. Sci., 19:177-183 (1998); E. Itoh, M. Fujimiay, and A. Inui, "Thioperamide, A histamine $H_3$ receptor antagonist, powerfully suppresses peptide YY-induced food intake in rats," Biol. Psych., 45(4):475-481 (1999); S.I. Yates, et al., "Effects of a novel histamine $H_3$ receptor antagonist, GT-2394, on food intake and weight gain in Sprague-Dawley rats," Abstracts, Society for Neuroscience, 102.10:219 (November, 2000); and C. Bjenning, et al., "Peripherally administered ciproxifan elevates hypothalamic histamine levels and potently reduces food intake in the Sprague Dawley rat," Abstracts, International Sendai Histamine Symposium, Sendai, Japan, #P39 (November, 2000).

The ability of the compounds of the invention, including, but not limited to, those specified in the examples, to treat inflammation and pain may be demonstrated by Phillips, et al., Annual Reports in Medicinal Chemistry 33:31-40 (1998).

The ability of the compounds of the invention, including, but not limited to, those specified in the examples, to treat migraine may be demonstrated by R. Leurs, R.C. Vollinga and H. Timmerman, "The medicinal chemistry and therapeutic potential of ligands of the histamine $H_3$ receptor," Progress in Drug Research 45:170-165 (1995); Matsubara, et al., Eur. J. Pharmacol., 224:145 (1992); and Rouleau, et al., J. Pharmacol. Exp. Ther., 281:1085 (1997).

The ability of the compounds of the invention, including, but not limited to, those specified in the examples, to treat cancer, in particular, melanoma, cutaneous carcinoma and medullary thyroid carcinoma may be demonstrated by Polish Med. Sci. Mon., 4(5):747 (1998); Adam Szelag, "Role of histamine $H_3$-receptors in the proliferation of neoplastic cells in vitro," Med. Sci. Monit., 4(5):747-755 (1998); and C.H. Fitzsimons, et al., "Histamine receptors signalling in epidermal tumor cell lines with H-ras gene alterations," Inflammation Res., 47 (Suppl 1):550-551 (1998).

The ability of the compounds of the invention, including, but not limited to, those specified in the examples, to treat vestibular dysfunctions, in particular, Meniere's disease may be demonstrated by R. Leurs, R.C. Vollinga and H. Timmerman, "The medicinal chemistry and therapeutic potential of ligands of the histamine $H_3$ receptor," Progress in Drug Research 45:170-165 (1995), and Pan, et al., Methods and Findings in Experimental and Chemical Pharmacology 21:771-777 (1998).

The ability of the compounds of the invention, including, but not limited to, those specified in the examples, to treat asthma may be demonstrated by A. Delaunois, et al., "Modulation of acetylcholine, capsaicin and substance P effects by histamine $H_3$ receptors in isolated perfused rabbit lungs," European Journal of Pharmacology 277(2-3):243-250 (1995); and Dimitriadou, et al., "Functional relationship between mast cells and C-sensitive nerve fibres evidenced by histamine $H_3$-receptor modulation in rat lung and spleen," Clinical Science 87(2):151-163 (1994).

The ability of the compounds of the invention, including, but not limited to, those specified in the examples, to allergic rhinitis may be demonstrated by McLeod, et al., Progress in Resp. Research 31:133 (2001).

Compounds of the invention are particularly useful for treating and preventing a condition or disorder affecting the memory or cognition.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 30 mg/kg/day. For purposes of oral administration, more preferable doses can be in the range of from about 0.1 to about 15 mg/kg/day. If desired, the effective daily dose can be divided into multiple doses for purposes of administration; consequently, single dose compositions may contain such amounts or submultiples thereof to make up the daily dose.

The compounds and processes of the invention will be better understood by reference to the following examples and reference examples, which are intended as an illustration of and not a limitation upon the scope of the invention.

REFERENCE EXAMPLES

Reference Example 1

2-(R)-Methyl-azetidine hydrochloride

Reference Example 1A 2-(S)-Methanesulfonyloxymethyl-azetidine-1-carboxylic acid tert-butyl ester 2-(S)-Hydroxymethyl-azetidine-1-carboxylic acid tert-butyl ester (prepared as described in Abreo, et al. J. Med. Chem. 1996, 39, 817-825) (9.7 g, 52 mmol) was taken up in dichloromethane (50 mL), treated with triethylamine (8.7 mL, 62 mmol), cooled to 0° C., treated dropwise with methanesulfonyl chloride (4.4 mL, 57 mmol), stirred overnight at ambient temperature, treated with sodium bicarbonate solution (50 mL) and the layers were separated. The aqueous layer was extracted with dichloromethane (50 mL). The combined organic layers were dried ($MgSO_4$), filtered, concentrated and chromatographed on silica gel eluting with a gradient of 10:1, 5:1, 2:1 and 3:2 hexane:ethyl acetate to provide 10.7 g (78%). $^1$H NMR (300 MHz, $CDCl_3$) δ 1.45 (s, 9 H) 2.27 (m, 2 H) 3.05 (s, 3 H) 3.82 (m, 2 H) 4.28 (dd, J=10.85, 2.71 Hz, 1 H) 4.43 (m, 1 H) 4.54 (dd, J=10.85, 4.07 Hz, 1 H).

Reference Example 1B 2-(R)-Methyl-azetidine-1-carboxylic acid tert-butyl ester 2-(S)-Methanesulfonyloxymethyl-azetidine-1-carboxylic acid tert-butyl ester was (4.83 g, 18.2 mmol) was taken up in THF (11 mL), cooled to 0° C. under $N_2$, treated drop-wise with a lithium triethylborohydride (1.0 M in THF, 73 mL), stirred at ambient temperature for 6 hours, treated with ethyl acetate (500 mL), washed with water, washed with 0.25 M HCl, washed with $NaHCO_3$ solution, washed with brine (2×), dried ($MgSO_4$), filtered, concentrated and purified by chromatography on silica gel eluting with a gradient of 10:1 and then 5:1 hexane:ethyl acetate to provide 0.95 g (30%) of the title compound. $^1$H NMR (300 MHz, $CDCl_3$) δ 1.37 (d, J=6.10 Hz, 3 H) 1.44 (s, 9 H) 1.76 (m, 1 H) 2.27 (m, 1 H) 3.81 (t, J=7.46 Hz, 2 H) 4.28 (m, 1 H).

Reference Example 1C 2-(R)-Methyl-azetidine hydrochloride 2-(R)-Methyl-azetidine-1-carboxylic acid tert-butyl ester (0.95 g) was treated with concentrated HCl (3 mL), stirred for 1 hour, concentrated and dried under vacuum to provide the title compound. $^1$H NMR (300 MHz, $CDCl_3$) δ 1.67 (d, J=6.44 Hz, 3 H) 2.31 (m, 1 H) 2.58 (m, 1 H) 3.97 (m, 2 H) 4.61 (m, 1 H) 9.58 (br. s., 2H).

Reference Example 2

2-(S)-Fluoromethyl-azetidine hydrochloride

Reference Example 2A 2-(S)-Fluoromethyl-azetidine-1-carboxylic acid tert-butyl ester 2-(S)-Methanesulfonyloxymethyl-azetidine-1-carboxylic acid tert-butyl ester (5.62 g, 21.2 mmol) was treated with tetrabutylammonium fluoride (1 M solution in THF, 191 mL) under $N_2$, heated to reflux for 1 hour, cooled to ambient temperature, concentrated to 50 mL, treated with water (100 mL) and extracted with ethyl acetate (2×250 mL). The combined ethyl acetate layers were washed with 0.25 M HCl (100 mL), washed with $NaHCO_3$ solution, washed with brine, dried ($MgSO_4$), filtered, concentrated and chromatographed (10:1 and then 5:1 hexane:ethyl acetate) to provide 2.9 g (72%). $^1$H NMR (300 MHz, $CDCl_3$) δ 1.44 (s, 9 H) 2.26 (m, 2 H) 3.84 (t, J=7.46 Hz, 2 H) 4.35 (m, 1 H) 4.42 (ddd, J=46.36, 9.92, 2.71 Hz, 1 H) 4.72 (ddd, J=48.31, 10.00, 3.05 Hz, 1 H).

Reference Example 2B 2-(S)-Fluoromethyl-azetidine hydrochloride 2-(S)-Fluoromethyl-azetidine-1-carboxylic acid tert-butyl ester (2.9 g, 15 mmol) was treated with concentrated HCl (6 mL), stirred for 1 hour at ambient temperature, concentrated and dried under vacuum. $^1$H NMR (300 MHz, CD$_3$OD) δ 2.59 (m, 2 H) 3.92 (m, 1 H) 4.07 (m, 1 H) 4.65 (d, J=3.73 Hz, 1 H) 4.72 (m, 1 H) 4.81 (d, J=3.39 Hz, 1 H) 4.87 (5, 2 H).

Reference Example 3

2-(S)-Hydroxymethyl-azetidine hydrochloride 2-(S)-Hydroxymethyl-azetidine-1-carboxylic acid tert-butyl ester (1.8 g), prepared as described in Abreo, et al. J. Med. Chem. 1996, 39, 817-825, was treated with concentrated HCl (6 mL), stirred at ambient temperature for 1 hour, concentrated and dried under vacuum. $^1$H NMR (300 MHz, CDCl$_3$) δ 2.50 (m, 2 H) 3.87-4.15 (m, 4 H) 4.27 (br. s, 1 H) 4.66 (m, 1 H) 8.95 (br. s, 1 H) 9.35 (br. s, 1 H).

Reference Example 4

Preparation of (2R)-2-methylpyrrolidine and (2S)-2-methylpyrrolidine (2R)-2-Methylpyrrolidine tartrate was prepared by the resolution of racemic (+/−) 2-methylpyrrolidine with L-tartaric acid (which is also called (2R,3R)-(+)-tartaric acid, Chemical Abstracts number 87-69-4, available from Aldrich Chemical Co., Milwaukee, Wis.) using enantioselective recrystallization procedures as described by William Gaffield, et al. in Tetrahedron, 37:1861-1869 (1981), or in Karrer and Ehrhardt in Helv. Chim. Acta, 34: 2202, 2208 (1951). (2R)-2-methylpyrrolidine hydrobromide also is a suitable source of (2R)-2-methylpyrrolidine, and was prepared from L-prolinol (which also called (S)-(+)-pyrrolidinemethanol, Chemical Abstracts number 23356-96-9, Aldrich Chemical Co., Milwaukee, Wis.) using the procedure described by Nijhuis, Walter H.N., et al., J.Org.Chem., 54(1): 209-216, 214 (1989). Other procedures describing the synthesis of R-2-methylpyrrolidine and salts thereof can be found in Andres, Jose M., et al. Eur.J.Org.Chem., 9:1719-1726 (2000); and Elworthy, Todd R.; Meyers, A.I., Tetrahedron, 50(20): 6089-6096).

(2S)-2-Methylpyrrolidine can be substituted for (2R)-2-methylpyrrolidine in the experimental procedures provided herein. The (2S)-2-methylpyrrolidine can be prepared by procedures described in Kim, Mahn-Joo, et al., Bioorg. Med. Chem. Lett. 6(1):71-76 (1996).

EXAMPLES

Example 1

4-{2-[2-(2-(R)-Methyl-pyrrolidin-1-yl)-ethyl]-benzothiazol-5-yl}-benzonitrile

Example 1A 2-(5-Bromo-benzothiazol-2-yl)-ethanol

To a dry 100 mL flask, 2,2,6',6'-tetra-methyl piperidine (0.56 g, 4 mmol) and 6 mL of THF was added and cooled to −78° C. Then n-BuLi (1.5 mL, 2.5M) was added rapidly, and the mixture of LiTMP was stirred for 3 hr. 5-Bromo-2-methyl-benzothiazole (0.75 g, 3.3 mmol) was added in solid form in to the reaction at −78° C., and after stirring for 4 hours at −78° C., 6 equivalents of para-formaldehyde was added to the reaction while stirring rapidly. The reaction was worked up by addition of sat. NH$_4$Cl solution, and the reaction was extracted with CH$_2$Cl$_2$ dried, and concentrated in vacuo to give crude product, 1.02 g. The crude product was purified by flash chromatography, eluting with CH$_2$Cl$_2$, then with 20% MeOH/CH$_2$Cl$_2$ to elute the product. $^1$H NMR (400 MHz, CDCl$_3$) d ppm 3.32 (t, J=5.76 Hz, 2 H) 4.11 (q, J=5.95 Hz, 2 H) 7.48 (dd, J=8.51, 1.92 Hz, 1 H) 7.70 (d, J=8.51 Hz, 1 H) 8.11 (d, J=1.92 Hz, 1 H)

Example 1B

Methanesulfonic acid 2-(5-bromo-benzothiazol-2-yl)-ethyl ester

To a mixture of 2-(5-bromo-benzothiazol-2-yl)-ethanol (0.94 g, 3.6 mmol) in 10 mL CH$_2$Cl$_2$, Et$_3$N (0.99 g, 9.8 mmol), was added methanesulfonyl chloride (0.46 g, 4.0 mmol) dropwise at room temperature. The reaction was worked up by concentrating under vacuum and then used in the next step, Example 1C.

Example 1C

5-Bromo-2-[2-(2-(R)-methyl-pyrrolidin-1-yl)-ethyl]-benzothiazole

The methanesulfonic acid 2-(5-bromo-benzothiazol-2-yl)-ethyl ester from Example 1B, and 2 equivalents (7.3 mmol) of 2-(R)-methylpyrrolidine (at a concentration of 10 mg/mL solution in acetonitrile), was combined with excess Et$_3$N (0.99 g, 9.8 mmol), and the resulting mixture was heated to 60° C. for 2 hr. The solvent was removed under vacuum, and the residue dissolved in CH$_2$Cl$_2$. and washed with saturated NaHCO$_3$ (twice). The organic layer as dried over MgSO$_4$ and concentrated in vacuo to give crude product, 1.15 g (97.1%). $^1$H NMR (400 MHz, CDCl$_3$) δ ppm 1.06 (d, J=6.04 Hz, 3 H) 1.78-1.6 (m, 3 H) 1.88 (m, 1H) 2.20 (m, 1 H) 2.38 (m, 1H) 2.55 (m, 1H) 3.23 (m, 4 H) 7.37 (dd, J=8.44, 1.85 Hz, 1 H) 7.61 (d, J=8.51 Hz, 1 H) 8.02 (d, J=1.92 Hz, 1 H). MS m/z 125,127 (M+H)$^+$, (M+3H)$^+$.

Example 1D

4-{2-[2-(2-(R)-Methyl-pyrrolidin-1-yl)-ethyl]-benzothiazol-5-yl}-benzonitrile

To a reaction flask containing K$_2$CO$_3$ (0.326 g, 1.5 mmol), CsF (0.233 g, 1.5 mmol), and (0.19 g, 1.3 mmol) of 4-cyanophenyl boronic acid was added a solution of 5-bromo-2-[2-(2-methyl-pyrrolidin-1-yl)-ethyl]-benzothiazole (0.25 g, 0.77 mmol) in 3 mL of toluene. The resulting mixture was purged with nitrogen, and then 2-dicyclohexylphosphinobiphenyl (54 mg, 0.15 mmol) and Pd$_2$(dba)$_3$ (70 mg, 0.08 mmol) were added. The resulting reaction mixture was then heated at 90° C. for 2 hr. At completion, the reaction was washed with water, then diluted with CH$_2$Cl$_2$, and purified by column chromatography (silica gel, 10% MeOH/CH$_2$Cl$_2$), to give 4-{2-[2-(2-methyl-pyrrolidin-1-yl)-ethyl]-benzothiazol-5-yl}-benzonitrile in an isolated yield of 31.5%. The hydrochloride salt of the product was formed by adding 6N HCl (2 equivalents) in isopropanol solution and then diluting with 1 mL of isopropanol, followed by removal of solvent. $^1$H NMR (400 MHz, Methanol d$_4$) δ 1.47 (d, J=6.45 Hz, 3 H) 1.72 (dd, J=12.76, 8.37 Hz, 1 H) 2.29 (m, 2 H) 3.23 (m, 3 H) 3.36 (t, J=7.14 Hz, 1 H) 3.62 (m, 3 H) 3.99 (m, 1 H) 7.68 (dd, J=8.44, 1.72 Hz, 1 H) 7.77 (m, 4 H) 8.01 (d, J=8.37 Hz, 1 H) 8.17 (d, J=1.51 Hz, 1 H) [M+H]⁺ at m/z 348.

Example 2

5-{2-[2-(2-(R)-Methyl-pyrrolidin-1-yl)-ethyl]-benzothiazol-5-yl}nicotinonitrile

Example 2A

4-Bromo-2-nitro-benzenethiol

Finely powdered $Na_2S$ (41.04 g, 0.170 mol) was added to DMF (400 mL) and purged with $N_2$ in a 3-neck-flask equipped with a mechanical stirrer. After 30 minutes, 1,4-Dibromo-2-nitro-benzene (40 g, 0.142 mol) dissolved in 30 mL of DMF was added in portions. The reaction was stirred at room temperature, and was found to be complete in 2 hours when assessed by HPLC. Water (750 mL) was added, and insoluble material was removed by filtration. The pH of the reaction filtrate was adjusted with HCl (15 mL) to pH 4, at which point a yellow precipitate came out of solution, which was collected by filtration and washed with water. The yield of unpurified 4-bromo-2-nitro-benzenethiol and its disulfide (4-bromo-2-nitro-benzenethiol disulfide) was 28.09 g (84.2%).

Example 2B

2-Amino-4-bromo-benzenethiol

The mixture of 4-bromo-2-nitro-benzenethiol and its disulfide from Example 2A (14.9 g, 53.5 mmol) in THF (450 mL) was mixed with Raney Ni (30 g, 100% wt). The mixture was hydrogenated in a 1000 mL Paar shaker at a hydrogen pressure of 40 psi at 50° C. for 41 hours. When the reaction was complete, the solids were filtered. The solid filter-cake was dissolved in pyridine (600 mL) at 100° C. and filtered to remove the Ni residue. This pyridine solution contained mostly the 2-amino-4-bromophenyldisulfide. Crude yield=11.9 g (92%)

Example 2C

6-Bromo-3-hydroxy-4H-benzo[1,4]thiazine-2-carboxylic acid ethyl ester

The 2-amino-4-bromophenyldisulfide solution in pyridine from Example 2B was concentrated in vacuo to a volume of 300 mL and cooled to 0° C. under nitrogen. Chlorocarbonyl-acetic acid ethyl ester (25 g, 0.167 mol) was added dropwise and the mixture was warmed to room temperature and stirred for 2 days. The mixture was extracted with $CHCl_3$ and washed with water several times to remove pyridine. Evaporation of the chloroform solutions gave the crude material (6-bromo-3-hydroxy-4H-benzo[1,4]thiazine-2-carboxylic acid ethyl ester) which was carried on to the next step.

Example 2D (5-Bromo-benzothiazol-2-yl)-acetic acid ethyl ester

A mixture of the crude material from Example 2C (2.7 g, 8.5 mmol) in acetic acid (60 mL) and heated to 110° C. Then Zn (18 equivalents) was added slowly in portions over 30 min to the mixture under nitrogen. After the completion the mixture was cooled to room temperature and the Zn residue was filtered off. The filter cake was washed with MeOH. And the combined filtrate was stripped to dryness. The residue was dissolved in 70 mL of chloroform and washed with water twice. The chloroform solution was dried with anhydrous $MgSO_4$ and concentrated to dryness. The crude product was purified by column chromatography (silica gel, 10% EtOAc/Hexane). Purified yield for the three steps from example 2B-2D was 1.11 g (43.3%).

Example 2E 2-(5-Bromo-benzothiazol-2-yl)-ethanol (5-Bromo-benzothiazol-2-yl)-acetic acid ethyl ester (1.25 g, 4.2 mmol) was dissolved in THF (20 mL) and EtOH (5 mL) under $N_2$. Then 0.24 g of $NaBH_4$ was dissolved in EtOH (3 mL) and added to the above solution. The reaction mixture was stirred at room temperature for 2 hours. After the completion the mixture was quenched with water and extracted with $CH_2Cl_2$. The aqueous layer was extracted again with more $CH_2Cl_2$. The combined methylene chloride layer was dried over anhydrous $MgSO_4$ and filtered. Removal of solvent gave crude product with a yield of 1.11 g. The crude product was used directly in the next step.

Example 2F

5-Bromo-2-[2-(2-(R)-methyl-pyrrolidin-1-yl)-ethyl]-benzothiazole

A solution of 2-(5-bromo-benzothiazol-2-yl)-ethanol (1.50 g, 5.8 mmol) and triethylamine (1.33 g, 11.6 mmol) in $CH_2Cl_2$ was cooled to 0° C., and mesyl chloride was added dropwise. The mixture was warmed to room temperature and stirred for 1 hr. The solvent was removed under vacuum, and to the residue was added acetonitrile (20 mL), triethylamine (1.33 g, 11.6 mmol) 2-(R)-methylpyrrolidine hydrochloride (2.83 g, 23.2 mmol) to the mixture, and the mixture was stirred at 60° C. for 1 hr. Solvents were removed under vacuum, and the residue was dissolved in 20 mL methylene chloride and washed with 10 mL water. The aqueous layer was re-extracted with 10 mL methylene chloride. The combined methylene chloride extracts were concentrated to give a crude product yield 1.9 g (100%)

Example 2G

5-{2-[2-(2-(R)-Methyl-pyrrolidin-1-yl)-ethyl]-benzothiazol-5-yl}-nicotinonitrile The title compound was prepared by a method similar to that described in Example 1D, but substituting 3-cyano-5-(4,4,5,5,-tetramethyl-[1,3,2]dioxaboronlan-2-yl)-pyridine for 4-cyanophenyl boronic acid. The resulting mixture was silica gel column purified with 100/5/1=$CHCl_3$/MeOH/$NH_4OH$. Isolated yield=51.7%. $^1H$ NMR (400 MHz, Chloroform-D) δ 1.04 (d, 3 H) 1.35 (m, 1 H) 1.67 (m, 2 H) 1.87 (m, 1H) 2.17 (q, 1 H) 2.37 (m, 1 H) 2.55 (m, 1 H) 3.11 (m, 1 H) 3.22 (m, 3 H) 7.46 (dd, J=8.30, 1.85 Hz, 1 H) 7.88 (d, J=8.37 Hz, 1 H) 8.02 (d, J=1.37 Hz, 1 H) 8.16 (t, J=2.13 Hz, 1 H) 8.72 (d, J=1.78 Hz, 1 H) 8.95 (d, J=2.20 Hz, 1 H) $^{13}C$ NMR (400 MHz, Chloroform-d) δ 18.32, 21.58, 24.38, 32.47, 33.05, 52.39, 53.46, 60.04, 120.31, 122.25, 123.25, 132.90, 137.32. [M+H]⁺ at m/z 349.

Example 3

3-{2-[2-(2-(R)-Methyl-pyrrolidin-1-yl)-ethyl]-benzothiazol-5-yl}-benzonitrile The title compound was prepared according to the procedure in Example 1D, but substituting 3-cyanophenyl boronic acid for 4-cyanophenyl boronic acid. Purification by preparative reversed phase HPLC, eluting with acetonitrile/aqueous trifluoroacetic acid gave an isolated yield of 73.3% of 3-{2-[2-(2-(R)-Methyl-pyrrolidin-1-yl)-ethyl]-benzothiazol-5-yl}-benzonitrile. $^1$H NMR (400 MHz, Methanol-d) δ 1.48 (d, J=6.45 Hz, 3 H) 1.73 (m, 1 H) 2.06 (m, 2 H) 2.30 (m, 1 H) 3.26 (m, 1 H) 3.59 (m, 4 H) 3.73 (m, 1 H) 4.01 (m, 1 H) 7.59 (t, J=7.82 Hz, 1 H) 7.67 (m, 2 H) 7.95 (m, 1 H) 8.01 (m, 2 H) 8.18 (d, J=1.78 Hz, 1 H). [M+H]$^+$ at m/z 348.

Example 4

2-[2-(2-(R)-Methyl-pyrrolidin-1-yl)-ethyl]-5-p-tolyl-benzothiazole

The title compound was prepared according to the procedure in Example 1D, but substituting 4-methylphenyl boronic acid for 4-cyanophenyl boronic acid. Purification by preparative reversed phase HPLC, eluting with acetonitrile/aqueous trifluoroacetic acid gave an isolated yield of 24.7%. $^1$H NMR (400 MHz, Methanol-d) δ 0.94 (d, J=6.31 Hz, 3 H) 1.19 (dd, J=12.49, 8.78 Hz, 1 H) 1.51 (m, 2 H) 1.76 (s, 3H) 2.68 (m, 1 H) 3.02 (d, J=11.53 Hz, 2 H) 3.22 (m, 1 H) 3.43 (d, J=12.76 Hz, 1 H) 6.67 (d, J=7.96 Hz, 2 H) 7.19 (dd, J=8.51, 1.37 Hz, 1 H) 7.51 (d, J=8.51 Hz, 1 H) 7.57 (d, J=1.37 Hz, 1 H); $^{13}$C NMR (400 MHz, Methanol-d) δ 16.55, 21.31, 22.69, 25.33, 32.53, 52.11, 54.93, 64.73, 66.72, 118.68, 123.64, 126.56, 127.74, 130.34. [M+H]$^+$ at m/z 337.

Example 5

2-[2-(2-(R)-Methyl-pyrrolidin-1-yl)-ethyl]-5-m-tolyl-benzothiazole

The title compound was prepared according to the procedure in Example 1D, but substituting 3-methylphenyl boronic acid for 4-cyanophenyl boronic acid. Purification by preparative reversed phase HPLC, eluting with acetonitrile/aqueous trifluoroacetic acid gave an isolated yield of 33.8%. $^1$H NMR (400 MHz, methanol-d) δ 0.95 (d, J=6.17 Hz, 1 H) 1.36 (d, J=6.45 Hz, 3 H) 1.61 (m, 1 H) 1.94 (m, 2 H) 2.16 (m, 1 H) 2.21 (d, J=4.94 Hz, 3 H) 3.12 (m, 2 H) 3.42 (m, 2 H) 3.62 (m, 1 H) 3.84 (d, J=12.90 Hz, 1 H) 7.00 (m, 1 H) 7.15 (t, J=7.62 Hz, 1 H) 7.27 (m, 2 H) 7.54 (dd, J=8.51, 1.78 Hz, 1 H) 7.86 (m, 1 H) 7.97 (d, J=1.24 Hz, 1 H). $^{13}$C NMR (400 MHz, Methanol-d) δ 16.57, 21.72, 22.70, 25.36, 32.53, 40.22, 52.32, 54.97, 66.69, 120.15, 123.14, 125.00, 126.12, 128.48, 129.16, 129.55, 133.96, 139.37, 140.78, 141.64, 151.76. [M+H]$^+$ at m/z 337.

Example 6

5-(4-Chloro-phenyl)-2-[2-(2-(R)-methyl-pyrrolidin-1-yl)-ethyl]-benzothiazole The title compound was prepared according to the procedure in Example 1D, but substituting 4-chlorophenyl boronic acid for 4-cyanophenyl boronic acid. Purification by preparative reversed phase HPLC, eluting with acetonitrile/aqueous trifluoroacetic acid gave an isolated yield of 27.0%. $^1$H NMR (400 MHz, Methanol-d) δ 1.14 (d, J=6.17 Hz, 1 H) 1.55 (d, J=6.45 Hz, 3 H) 1.83 (m, 1 H) 2.13 (m, J=5.76 Hz, 2 H) 2.35 (m, J=7.41 Hz, 1 H) 3.30 (m, 2 H) 3.61 (m, 2 H) 3.81 (m, 1 H) 4.04 (d, J=12.76 Hz, 1 H) 7.46 (m, 2 H) 7.69 (m, 3 H) 8.05 (d, J=8.37 Hz, 1 H) 8.17 (d, J=1.51 Hz, 1 H). $^{13}$C NMR (400 MHz, Methanol-d) δ 16.60, 22.72, 32.55, 52.43, 55.02, 66.69, 120.75, 123.17, 125.54, 134.4, 134.94, 139.70, 153.15, 169.00. [M+H]$^+$ at m/z 357.

Example 7

5-(3-Chloro-phenyl)-2-[2-(2-(R)-methyl-pyrrolidin-1-yl)-ethyl]-benzothiazole The title compound was prepared according to the procedure in Example 1D, but substituting 3-chlorophenyl boronic acid for 4-cyanophenyl boronic acid. Purification by preparative reversed phase HPLC, eluting with acetonitrile/aqueous trifluoroacetic acid gave an isolated yield of 28.5%. $^1$H NMR (400 MHz, Methanol-d) δ 1.06 (d, J=6.17 Hz, 1 H) 1.47 (d, J=6.45 Hz, 3 H) 1.74 (m, 1 H) 2.05 (m, 2 H) 2.28 (m, 1 H) 3.23 (m, 2 H) 3.53 (m, 2 H) 3.73 (m, 1 H) 3.96 (d, J=12.90 Hz, 1 H) 7.29 (m, 1 H) 7.36 (t, J=7.82 Hz, 1 H) 7.52 (m, 1 H) 7.61 (m, 2 H) 7.97 (m, 1 H) 8.09 (d, J=1.65 Hz, 1 H). $^{13}$C NMR (400 MHz, Methanol-d) δ 16.59, 22.71, 32.54, 52.41, 55.02, 66.69, 120.97, 123.22, 125.59, 126.3, 127.77, 128.27, 131.14. [M+H]$^+$ at m/z 357.

Example 8

5-(4-Ethyl-phenyl)-2-[2-(2-(R)-methyl-pyrrolidin-1-yl)-ethyl]-benzothiazole

The title compound was prepared according to the procedure in Example 1D, but substituting 4-ethylphenyl boronic acid for 4-cyanophenyl boronic acid. Purification by preparative reversed phase HPLC, eluting with acetonitrile/aqueous trifluoroacetic acid gave an isolated yield of 25.5%. $^1$H NMR (400 MHz, Methanol-d) δ 1.18 (m, 3 H) 1.47 (d, J=6.45 Hz, 3 H) 1.73 (m, 2 H) 2.04 (m, 2 H) 2.27 (m, 1 H) 2.60 (q, J=7.64 Hz, 2 H) 3.22 (m, 2 H) 3.53 (m, 2 H) 3.73 (m, 1 H) 3.95 (d, J=12.76 Hz, 1 H) 7.22 (d, J=8.37 Hz, 2 H) 7.51 (m, 2 H) 7.63 (dd, J=8.37, 1.78 Hz, 1 H) 7.94 (d, J=8.37 Hz, 1 H) 8.08 (d, J=1.37 Hz, 1 H). $^{13}$C NMR (400 MHz, Methanol-d) δ 1659, 22.72, 25.37, 26.74, 29.60, 32.54, 52.44, 55.01, 66.70, 120.36, 122.97, 125.76, 127.78, 129.11. [M+H]$^+$ at m/z 351.

Example 9

Dimethyl-(4-{2-[2-(2-(R)-methyl-pyrrolidin-1-yl)-ethyl]-benzothiazol-5-yl}-phenyl)-amine The title compound was prepared according to the procedure in Example 1D, but substituting (4-dimethylamino)phenyl boronic acid for 4-cyanophenyl boronic acid. Purification by preparative reversed phase HPLC, eluting with acetonitrile/aqueous trifluoroacetic acid gave an isolated yield of 38.0%. $^1$H NMR (400 MHz, Methanol-d) δ 1.46 (d, J=6.45 Hz, 3 H) 1.72 (m, 1 H) 2.04 (m, 2 H) 2.27 (m, 1 H) 3.20 (m, 2 H) 3.24 (m, 6 H) 3.55 (m, 3 H) 3.72 (m, 1 H) 3.96 (m, 1 H) 7.65 (dd, J=8.44, 1.72 Hz, 1 H) 7.73 (m, 2 H) 7.84 (m, 2 H) 7.99 (d, J=8.37 Hz, 1 H) 8.14 (d, J=1.51 Hz, 1 H). $^{13}$C NMR (400 MHz, Methanol-d) δ 16.60, 22.69, 30.69, 32.52, 47.29, 52.46, 55.02, 66.65, 121.44, 122.01, 123.27, 125.44, 129.93, 135.91, 138.62, 142.73, 143.41. [M+H]$^+$ at m/z 366.

Example 10

5-(4-Fluoro-phenyl)-2-[2-(2-(R)-methyl-pyrrolidin-1-yl)-ethyl]-benzothiazole The title compound was prepared according to the procedure in Example 1D, but substituting 4-fluorophenyl boronic acid for 4-cyanophenyl boronic acid. The resulting mixture was silica gel column purified with 10%=MeOH/CHCl$_3$. The isolated yield was 33.3%. $^1$H NMR (400 MHz, Chloroform-d) δ 1.17 (m, 1 H) 1.63 (d, J=6.31 Hz, 3 H) 1.96 (m, 1 H) 2.18 (s, 3 H) 3.28 (s, 1 H) 3.44 (m, 1 H) 3.91 (m, 3 H) 4.00 (m, 1 H) 7.14 (m, 2 H) 7.57 (m, 2 H) 7.72 (d, J=7.41 Hz, 1 H) 8.00 (d, J=8.37 Hz, 1 H) 8.23 (s, 1 H). $^{13}$C NMR (400 MHz, Chloroform-d) δ 16.10, 21.79, 25.41, 31.68, 50.94, 53.41, 65.50, 115.72, 117.66, 122.54, 126.44, 128.84. [M+H]$^+$ at m/z 341.

Example 12

2-[2-(2-(R)-Methyl-pyrrolidin-1-yl)-ethyl]-6-pyridin-3-yl-benzothiazole

Example 12A

2-amino-5-bromothiophenol and its Disulfide

A mixture of 6-bromobenzothiazolone (CAS number 62266-82-4, Aldrich Chemical Company (12.9 g, 56.1 mmol), NaOH (33 g, 0.825 mol) and water (90 mL) was heated to 100° C. for 15 hours under nitrogen. The mixture was cooled to 0° C. and pH was adjusted to pH 5 using 5N acetic acid at 0-10° C. under nitrogen. The precipitate was filtered, washed with water and vac. dried at 45° C. to give the product as a mixture of 2-amino-5-bromothiophenol and its disulfide (11.47 g, 100%).

Example 12B

(6-Bromo-benzothiazol-2-yl)-acetic acid ethyl ester and

Example 12C

7-Bromo-3-hydroxy-4H-benzo[1,4]thiazine-2-carboxylic acid ethyl ester

A solution of compound mixture of 2-amino-5-bromothiophenol and its disulfide (27.30 g, 0.134 mol) (from example 12A) in pyridine (190 mL) was cooled to −20° C., and chlorocarbonyl-acetic acid ethyl ester (50.35 g, 0.334 mol) was added dropwise at −20 to −8° C. The mixture was slowly warmed to room temperature and stirred for 46 h. Pyridine was removed under vacuum and the residue was dissolved in 500 mL methylene chloride, washed with 125 mL each of water, 2N HCl, 5% NaHCO$_3$ and water. The organic layer was concentrated to a pasty residue. The residue was stirred with 190 mL of 10:90 EtOAc:hexane. The precipitate was filtered, washed with 10:90 EtOAc:hexane and vacuum dried at 45° C. to give a brown solid (35.2 g) as a mixture of (6-bromo-benzothiazol-2-yl)-acetic acid ethyl ester and 7-bromo-3-hydroxy-4H-benzo[1,4]thiazine-2-carboxylic acid ethyl ester. The filtrate was concentrated to dryness, stirred with 50 mL hexane and the precipitate was filtered and dried to give 4.9 g of a second crop of the mixture.

A small sample of the second crop was chromatographed (silica gel, 20:90 EtOAc:hexane) to give pure (6-bromo-benzothiazol-2-yl)-acetic acid ethyl ester: $^1$H NMR (CDCl$_3$, 400 MHz) δ 130 (t, 3H, J=7 Hz), 4.15 (s, 2H), 4.25 (q, 2H, J=7 Hz), 7.55 (dd, 1H, J=8, 4 Hz), 7.83 (d, 1H, J=8 Hz), 7.99 (d, 1H, J=4 Hz); $^{13}$C NMR (CDCl$_3$, 400 MHz) §14.4, 39.9, 61.9, 118.5, 123.7, 129.2, 137.1, 151.1, 162.8, 167.6; (DCl/NH$_3$) m/z 300, 302 (M+H)$^+$.

The second pure fraction was identified to be 7-bromo-3-hydroxy-4H-benzo[1,4]thiazine-2-carboxylic acid ethyl ester: $^1$H NMR (CDCl$_3$, 400 MHz) δ 1.19 (t, 3H, J=4 Hz), 4.16 (q, 2H, J=4 Hz), 4.19 (s, 1H), 6.78 (d, 1H, J=4 Hz), 7.30 (dd, 1H, J=4, 2 Hz), 7.45 (d, 1H, J=2 Hz), 8.85 (s, 1H); (DCl/NH$_3$) m/z 316, 318 (M+H)$^+$, 333, 335 (M+NH$_4$)$^+$.

7-Bromo-3-hydroxy-4H-benzo[1,4]thiazine-2-carboxylic acid ethyl ester (2.47 g, 7.8 mmol) was dissolved in 50 mL of acetic acid and heated to 110° C. under nitrogen. Zinc powder (7.5 g, 114.7 mmol) was added in portions at room temperature over 80 minutes. The mixture was stirred at 110° C. for additional 2 hours and cooled to room temperature. Zinc was filtered off and rinsed with 20 mL EtOAc. The combined filtrate was concentrated to yellow crystals and purified by column chromatography (silica gel, 20:90 EtOAc:hexane) to give (6-bromo-benzothiazol-2-yl)-acetic acid ethyl ester.

Example 12D

2-(6-Bromo-benzothiazol-2-yl)-ethanol

To a stirred mixture of sodium borohydride (1.11 g, 29.3 mmol) in ethanol (10 mL) at room temperature was added a solution of the (6-bromo-benzothiazol-2-yl)-acetic acid ethyl ester (2.2 g, 7.3 mmol) in THF (25 mL) at 23-28° C. The mixture was stirred at room temperature for 15 hr, cooled to 3° C. and quenched with 20 mL water at 3-5° C. The product was extracted with 40 mL methylene chloride, washed with 20 mL 15% NaCl and concentrated to crude oil. The crude product was purified by column chromatography (silica gel, 10:90 MeOH:CHCl$_3$) to give the pure 2-(6-Bromo-benzothiazol-2-yl)-ethanol: $^1$H NMR (CDCl$_3$, 400 MHz) δ 3.30 (t, 2H, J=6 Hz), 4.11 (t, 2H, J=6 Hz), 7.54 (dd, 1H, J=5, 2 Hz), 7.78 (d, 1H, J=5 Hz), 7.95 (d, 1H, J=2 Hz). $^{13}$C NMR (CDCl$_3$, 400 MHz) δ 36.7, 60.8, 118.3, 123.3, 129.2, 136.1, 151.3, 169.5; (DCl/NH$_3$) m/z 258, 260 (M+H)$^+$.

Example 12E

6-Bromo-2-[2-(2-(R)-methyl-pyrrolidin-1-yl)-ethyl]-benzothiazole

A solution of 2-(6-bromo-benzothiazol-2-yl)-ethanol (2.23 g, 8.6 mmol) and triethylamine (2.19 g, 21.6 mmol) in THF (45 mL) was cooled to −20° C., and mesyl chloride (1.58 g, 13.8 mmol) was added at −20 to −10° C. The mixture was warmed to room temperature and stirred for 2 hr. Potassium carbonate (1.79 g, 13 mmol), 2-(R)-methylpyrrolidine hydrochloride (2.1 g, 17.2 mmol) and acetonitrile (40 mL) were added to the mixture, and the mixture was stirred at 60° C. for 18 hr. Solvents were removed and the residue was dissolved in 45 mL methylene chloride and washed with 10 mL water. The aqueous layer was re-extracted with 10 mL methylene chloride. The combined methylene chloride was concentrated to oil and purified by column chromatography (silica gel, 10:90 MeOH:CHCl$_3$) to give 6-bromo-2-[2-(2-methyl-pyrrolidin-1-yl)-ethyl]-benzothiazole (2.48 g, 88.3% yield). $^1$H NMR (CDCl$_3$, 400 MHz) δ 1.12 (d, 3H, J=7 Hz), 1.41-1.50 (m, 1H), 1.68-1.87 (m, 2H), 1.91-1.99 (m, 1H), 2.24 (q, 1H, J=7 Hz), 2.39-2.48 (m, 1H), 2.56-2.64 (m, 1H), 3.19-3.33 (m, 4H), 7.52 (dd, 1H, J=8, 4 Hz), 7.79 (d, 1H, J=8 Hz), 7.95 (d, 1H, J=4 Hz); $^{13}$C NMR (CDCl$_3$, 400 MHz) δ 19.3, 22.1, 33.1, 33.9, 52.5, 53.7, 59.9, 117.9, 123.3, 123.7, 128.9, 136.9, 151.3, 170.4; (DCl/NH$_3$) m/z 325, 327 (M+H)$^+$.

Example 12F

2-[2-(2-(R)-Methyl-pyrrolidin-1-yl)-ethyl]-6-pyridin-3-yl-benzothiazole

A mixture of 6-bromo-2-[2-(2-(R)-methyl-pyrrolidin-1-yl)-ethyl]-benzothiazole (0.3 g, 0.9 mmol), 3-pyridinyl boronic acid (0.17 g, 1.4 mmol) and 2-(dicyclohexylphosphino)biphenyl (65 mg, 0.2 mmol) in 15 mL of IPA was purged with nitrogen. Dichlorobis(triphenylphosphine)palladium II (65 mg, 0.1 mmol) was added. Sodium carbonate (0.15 g, 1.35 mmol) was dissolved in 5 g of water, purged with nitrogen, and added to the above mixture. The mixture was heated to 65° C. under nitrogen for 16 hr. After cooling to room temperature 20 mL of methylene chloride was added and the solid was filtered off. The filtrate was concentrated to oil and dissolved in 10 mL of 2N HCl. The acidic aqueous layer was washed with 10 mL methylene chloride, the pH adjusted with 4N NaOH to pH 10, and the product free base was extracted with 20 mL methylene chloride. The methylene chloride layer was concentrated to dryness and purified by column chromatography (silica gel, 10:90 MeOH:CHCl$_3$) to give the pure 2-[2-(2-Methyl-pyrrolidin-1-yl)-ethyl]-6-pyridin-3-yl-benzothiazole (0.2 g, 67% yield). $^1$H NMR (CDCl$_3$, 400 MHz) δ 1.14 (d, 3H, J=8 Hz), 1.42-1.51 (m, 1H), 1.71-1.86 (m, 2H), 1.92-2.00 (m, 1H), 2.27 (q, 1H, J=8 Hz), 2.41-2.48 (m, 1H), 2.60-2.67 (m, 1H), 3.22-3.37 (m, 4H), 7.36-7.39 (m, 1H), 7.64 (broad d, 1H, J=8 Hz), 7.90 (broad d, 1H, J=8 Hz), 8.03-8.05 (m, 2H), 8.60 (d, 1H, J=4 Hz), 8.89 (d, 1H, J=1.5 Hz); $^{13}$C NMR (CDCl$_3$, 400 MHz) δ 19.3, 22.2, 33.0, 34.0, 52.7, 53.8, 59.9, 119.7, 122.6, 123.3, 125.0, 134.2, 135.9, 136.2, 148.0, 148.1, 152.3, 170.7; (DCl/NH$_3$) m/z 324 (M+H)$^+$.

Example 13

2-[2-(2-(R)-Methyl-pyrrolidin-1-yl)-ethyl]-6-pyridin-4-yl-benzothiazole

The title compound was prepared according to the procedure described in Example 12F, but substituting 4-pyridinyl boronic acid for 3-pyridinyl boronic acid. The crude product was purified by column chromatography on silica gel, eluting with 10:90 MeOH:CHCl$_3$, to afford the title compound (33.5% yield). $^1$H NMR (CDCl$_3$, 400 MHz) δ 1.14 (6, 3H, J=8 Hz), 1.44-1.49 (m, 1H), 1.71-1.85 (m, 2H), 1.92-2.00 (m, 1H), 2.23-2.30 (m, 1H), 1.43-1.48 (m, 1H), 2.60-2.67 (m, 1H), 2.22-3.37 (m, 4H), 7.52 (d, 2H, J=6 Hz), 7.69 (dd, 1H, J=8, 2 Hz), 8.03 (d, 1H, J=8 Hz), 8.09 (d, 1H, J=2 Hz), 8.65 (d, 2H, J=6 Hz); $^{13}$C NMR (CDCl$_3$, 400 MHz) 19.1, 22.0, 33.0, 33.9, 52.5, 53.7, 59.9, 119.6, 121.4, 122.1, 122.6, 124.6, 125.4, 134.3, 136.2, 147.4, 149.8, 152.8, 171.2; (DCl/NH$_3$) m/z 324 (M+H)$^+$.

Example 14

6-(6-Methoxy-pyridin-3-yl)-2-[2-(2-(R)-methyl-pyrrolidin-1-yl)-ethyl]-benzothiazole The title compound was prepared according to the procedure described in Example 12F, but substituting 5-(2-methoxypyridinyl)boronic acid for 3-pyridinyl boronic acid. The crude product was purified by column chromatography on silica gel, eluting with 10:90 MeOH:CHCl$_3$, to afford the title compound (61.4% yield). $^1$H NMR (CDCl$_3$, 400 MHz) δ 1.15 (d, 3H, J=8 Hz), 1.42-1.52 (m, 1H), 1.71-1.87 (m, 2H), 1.94-2.00 (m, 1H), 2.24-2.30 (q, 1H, J=8 Hz), 2.44-2.48 (m, 1H), 3.24-3.37 (m, 4H), 3.98 (s, 3H), 6.82 (d, 1H, J=9.3 Hz), 7.58 (dd, 1H, J=8.4, 1.8 Hz), 7.82 (dd, 1H, J=8.6, 2.6 Hz), 7.95 (d, 1H, J=2.0 Hz), 8.00 (d, 1H, J=8.5 Hz), 8.41 (m, 1H); $^{13}$C NMR (CDCl$_3$, 400 MHz) 19.2, 22.1, 33.0, 33.9, 52.8, 53.7, 53.8, 60.0, 110.7, 119.0, 122.5, 124.7, 129.4, 134.4, 136.1, 137.3, 144.8, 151.8, 163.2, 170.1; (DCl/NH$_3$) m/z 354 (M+H)$^+$.

Example 15

6-(3-Chloro-pyridin-4-yl)-2-[2-(2-(R)-methyl-pyrrolidin-1-yl)-ethyl]-benzothiazole The title compound was prepared according to the procedure described in Example 12F, but substituting 4-(3-chloropyridinyl)boronic acid for 3-pyridinyl boronic acid. The crude product was purified by column chromatography on silica gel, eluting with 10:90 MeOH:CHCl$_3$, to afford the title compound (39.4% yield). $^1$H NMR (CDCl$_3$, 400 MHz) δ 1.15 (6, 3H, J=8 Hz), 1.43-1.52 (m 1H), 1.71-1.87 (m, 2H), 1.92-2.01 (m, 1H), 2.28 (q, 1H, J=8 Hz), 2.45-2.50 (m, 1H), 2.63-2.69 (m, 1H), 3.23-3.39 (m, 4H), 7.32 (d, 1H, J=8 Hz), 7.53 (dd, 1H, J=8, 4 Hz), 7.95 (d, 1H, J=4 Hz), 8.04 (d, 1H, J=8 Hz), 8.52 (d, 1H, J=4 Hz), 8.69 (s, 1H); $^{13}$C NMR (CDCl$_3$, 400 MHz) 19.2, 22.1, 33.0, 33.9, 52.6, 53.7, 60.0, 121.8, 122.0, 125.2, 126.5, 129.9, 132.6, 135.4, 146.7, 147.4, 149.8, 152.5, 171.3; (DCl/NH$_3$) m/z 358 (M+H)$^+$.

Example 16

6-(2,6-Difluoro-pyridin-3-yl)-2-[2-(2-(R)-methyl-pyrrolidin-1-yl)-ethyl]-benzothiazole The title compound was prepared according to the procedure described in Example 12F, but substituting 3-(2,6-difluoropyridinyl)boronic acid for 3-pyridinyl boronic acid. The crude product was purified by column chromatography on silica gel, eluting with 10:90 MeOH:CHCl$_3$, to afford the title compound (9.0% yield). $^1$H NMR (CDCl$_3$, 400 MHz) δ 1.15 (6, 3H, J=9 Hz), 1.43-1.52 (m, 1H), 1.69-1.89 (m, 2H), 1.92-2.01 (m, 1H), 2.28 (q, 1H, J=9 Hz), 2.42-2.68 (m, 1H), 3.23-3.39 (m, 4H), 6.94 (dd, 1H, J=8, 4 Hz), 7.57 (m, 1H), 7.98-8.04 (m, 3H); $^{13}$C NMR (CDCl$_3$, 400 MHz) 19.2, 22.1, 33.0, 34.0, 52.6, 53.7, 60.0, 106.3, 106.3, 106.6, 106.7, 121.4, 121.5, 122.4, 126.2, 126.3, 129.0, 129.0, 135.8, 144.6, 144.6, 144.7, 144.7, 152.3, 161.2, 171.2; (DCl/NH$_3$) m/z 360 (M+H)$^+$.

Example 17

2-Methyl-2'42-(2-(R)-methyl-pyrrolidin-1-yl)-ethyl)-[5,6']bibenzothiazolyl

The title product was prepared according to the procedure described in Example 12F, but substituting 5-(2-methyl-benzothiazolyl)boronic acid for 3-pyridinyl boronic acid. The crude product was purified by column chromatography on silica gel, eluting with 10:90 MeOH:CHCl$_3$, to afford the title compound (60.6% yield). $^1$H NMR (CDCl$_3$, 400 MHz) δ 1.15 (6, 3H, J=8 Hz), 1.42-1.51 (m, 1H), 1.70-1.89 (m, 1H), 1.92-2.00 (m, 1H), 2.27 (q, 1H, J=8 Hz), 2.42-2.48 (m, 1H), 2.62-2.70 (m, 1H), 2.86 (s, 3H), 3.23-3.39 (m, 4H), 7.61 (dd, 1H, J=8, 2 Hz), 7.72 (dd, 1H, J=8, 2 Hz), 7.87 (d, 1H, J=8 Hz), 8.03 (d, 1H, J=8 Hz), 8.08 (m, 1H), 8.19 (m, 1H); $^{13}$C NMR (CDCl₃, 400 MHz) 19.3, 20.5, 22.1, 33.1, 34.0, 52.8, 53.8, 59.9, 119.7, 120.7, 121.2, 122.4, 124.4, 125.4, 134.4, 136.0, 137.3, 138.7, 151.9, 153.7, 167.3 170.2; (DCl/NH₃) m/z 394 (M+H)⁺.

Example 18

3-{2-[2-(2-(R)-Methyl-pyrrolidin-1-yl)-ethyl]-benzothiazol-6-yl}-quinoline

The title compound was prepared according to the procedure described in Example 12F, but substituting 3-quinolinylboronic acid for 3-pyridinyl boronic acid. The crude product was purified by column chromatography on silica gel, eluting with 10:90 MeOH:CHCl₃, to afford the title compound (52.3% yield). ¹H NMR (CDCl₃, 400 MHz) δ 1.15 (6, 3H, J=8 Hz), 1.46-1.52 (m, 1H), 1.70-1.87 (m, 2H), 1.93-2.01 (m, 1H), 2.25-2.31 (q, 1H, J=8 Hz), 2.43-2.50 (m, 1H), 2.64-2.69 (m, 1H), 3.24-3.39 (m, 4H), 7.58 (m, 1H), 7.73 (m, 1H), 7.78 (dd, 1H, J=8, 3 Hz), 7.88 (dd, 1H, J=8, 3 Hz), 8.09 (d, 1H, J=8 Hz), 8.14 (dd, 1H, J=8, 3 Hz), 8.17 (m, 1H), 8.34 (m, 1H), 9.23 (d, 1H, J=4 Hz); ¹³C NMR (CDCl₃, 400 MHz) 19.3, 22.1, 33.1, 34.1, 52.7, 53.8, 60.1, 120.0, 122.8, 125.3, 126.8, 127.7, 129.0, 129.2, 133.1, 134.3, 136.3, 147.0, 149.5, 152.3; (DCl/NH₃) m/z 374 (M+H)⁺.

Example 19

2-[2-(2-(R)-Methyl-pyrrolidin-1-yl)-ethyl]-6-pyrimidin-5-yl-benzothiazole

The title compound was prepared according to the procedure described in Example 12F, but substituting 5-(4,4,5,5-tetramethyl-[1,3,2]dioxaborolan-2-yl)-pyrimidine for 3-pyridinyl boronic acid. The crude product was purified by column chromatography on silica gel, eluting with 10:90 MeOH:CHCl₃, to afford the title compound (63.5% yield). ¹H NMR (CDCl₃, 400 MHz) δ 1.15 (6, 3H, J=8 Hz), 1.41-1.52 (m, 1H), 1.71-1.89 (m, 2H), 1.93-2.01 (m, 1H), 2.24-2.31 (q, 1H, J=8 Hz), 2.44-2.49 (m, 1H), 2.61-2.68 (m, 1H), 3.23-3.40 (m, 4H), 7.64 (dd, 1H, J=8, 3 Hz), 8.05 (m, 1H), 8.08 (d, 1H, J=8 Hz), 8.99 (s, 1H), 9.21 (s, 1H); ¹³C NMR (CDCl₃, 400 MHz) 19.3, 22.1, 33.1, 34.0, 52.6, 53.7, 60.0, 119.7, 123.1, 124.6, 130.5, 133.8, 136.6, 152.8, 154.6, 157.1; (DCl/NH₃) m/z 325 (M+H)⁺.

Example 20

6-(6-Fluoro-pyridin-3-yl)-2-[2-(2-(R)-methyl-pyrrolidin-1-yl)-ethyl]-benzothiazole The title compound was prepared according to the procedure described in Example 12F, but substituting 2-fluoro-5-(4,4,5,5-tetramethyl[1,3,2]dioxaborolan-2-yl)-pyridine for 3-pyridinyl boronic acid. The crude product was purified by column chromatography on silica gel, eluting with 10:90 MeOH:CHCl₃, to afford the title compound (66.7% yield). ¹H NMR (CDCl₃, 400 MHz) δ 1.14 (6, 3H, J=8 Hz), 1.42-1.51 (m, 1H), 1.70-1.86 (m, 2H), 1.92-2.00 (m, 1H), 2.27 (q, 1H, J=8 Hz), 2.43-2.49 (m, 1H), 2.61-2.67 (m, 1H), 3.22-3.39 (m 4H), 7.01 (dd, 1H, J=8, 4 Hz), 7.58 (dd, 1H, J=8, 3 Hz), 7.97 (m, 1H), 8.00 (m, 1H), 8.03 (d, 1H, J=8 Hz), 8.45 (d, 1H, J=4 Hz); ¹³C NMR (CDCl₃, 400 MHz) 19.2, 22.1, 33.0, 33.9, 52.6, 53.7, 59.9, 109.1, 109.5, 119.6, 122.6, 124.8, 133.0, 134.1, 136.2, 139.4, 139.5, 145.4, 152.2, 161.4, 163.8, 170.8; (DCl/NH₃) m/z 342 (M+H)⁺.

Example 21

5-{2-[2-(2-(R)-Methyl-pyrrolidin-1-yl)-ethyl]-benzothiazol-6-yl}-nicotinonitrile The title compound was prepared according to the procedure described in Example 12F, but substituting 5-(4,4,5,5-tetramethyl-[1,3,2]dioxaborolan-2-yl)-nicotinitrile for 3-pyridinyl boronic acid. The crude product was purified by column chromatography on silica gel, eluting with 10:90 MeOH:CHCl₃, to afford the title compound (78.6% yield). ¹H NMR (CDCl₃, 400 MHz) δ 1.15 (6, 3H, J=8 Hz), 1.42-1.52 (m, 1H), 1.71-1.87 (m, 2H), 1.93-2.01 (m, 1H), 2.27 (q, 1H, J=8 Hz), 2.44-2.49 (m, 1H), 2.61-2.68 (m, 1H), 3.22-3.40 (m, 4H), 7.62 (dd, 1H, J=8, 4 Hz), 8.04 (m, 1H), 8.07 (d, 1H, J=8 Hz), 8.18 (m, 1H), 8.86 (d, 1H, J=4 Hz), 9.07 (d, 1H, J=4 Hz); ¹³C NMR (CDCl₃, 400 MHz) 19.2, 22.0, 33.0, 34.0, 52.5, 53.7, 59.9, 109.9, 116.2, 119.9, 123.0, 124.7, 131.6, 136.2, 136.5, 136.9, 150.2, 151.4, 152.8, 171.7; (DCl/NH₃) m/z 349 (M+H)⁺.

Example 22

6-(1-Methyl-1H-indol-5-yl)-2-[2-(2-(R)-methyl-pyrrolidin-1-yl)-ethyl]-benzothiazole The title compound was prepared according to the procedure described in Example 12F, but substituting 5-(1-methyl-1H-indolyl)boronic acid for 3-pyridinyl boronic acid. The crude product was purified by column chromatography on silica gel, eluting with 10:90 MeOH:CHCl₃, to afford the title compound (23.1% yield). ¹H NMR (CDCl₃, 400 MHz) δ 1.15 (6, 3H, J=8 Hz), 1.42-1.51 (m, 1H), 1.69-1.86 (m, 2H), 1.90-1.99 (m, 1H), 2.26 (q, 1H, J=8 Hz), 2.42-2.47 (m, 1H), 2.62-2.69 (m, 1H), 3.22-3.37 (m, 4H), 3.79 (s, 3H), 6.52 (m, 1H), 7.05 (d, 1H, J=4 Hz), 7.36 (d, 1H, J=8 Hz), 7.49 (dd, 1H, J=8, 2 Hz), 7.72 (dd, 1H, J=8, 4 Hz), 7.86 (m, 1H), 7.99 (d, 1H, J=8 Hz), 8.05 (m, 1H); ¹³C NMR (CDCl₃, 400 MHz) 19.2, 22.0, 33.0, 33.1, 33.8, 52.9, 53.8, 59.9, 101.2, 109.3, 119.4, 119.4, 121.2, 122.0, 125.5, 128.6, 129.2, 131.9, 135.7, 135.9, 139.2, 151.1, 169.1; (DCl/NH₃) m/z 376 (M+H)⁺.

Example 23

6-(2,6-Dimethyl-pyridin-3-yl)-2-[2-(2-(R)-methyl-pyrrolidin-1-yl)-ethyl]-benzothiazole The title compound was prepared according to the procedure described in Example 12F, but substituting 3-(2,6-dimethylpyridinyl)boronic acid for 3-pyridinyl boronic acid. The crude product was purified by column chromatography on silica gel, eluting with 10:90 MeOH:CHCl₃, to afford the title compound (67.9% yield). ¹H NMR (CDCl₃, 400 MHz) δ 1.15 (6, 3H, J=8 Hz), 1.42-1.52 (m, 1H), 1.69-1.87 (m 2H), 1.92-2.00 (m, 1H), 2.27 (q, 1H, J=8 Hz), 2.41-2.48 (m, 1H), 2.49 (s, 3H), 2.58 (s, 3H), 2.61-2.67 (m, 1H), 3.23-3.40 (m, 4H), 7.05 (d, 1H, J=8 Hz), 7.36 (dd, 1H, J=8, 3 Hz), 7.44 (d, 1H, J=8 Hz), 7.75 (m, 1H), 7.99 (d, 1H, J=8 Hz); ¹³C NMR (CDCl₃, 400 MHz) 19.2, 22.0, 23.7, 24.5, 33.0, 33.9, 52.7, 53.7, 59.9, 120.2, 121.4, 121.8, 126.9, 133.1, 135.3, 136.4, 137.3, 151.6, 154.5, 156.2, 170.1; (DCl/NH₃) m/z 352 (M+H)⁺.

Example 24

4-{2-[2-(2-methyl-pyrrolidin-1-yl)-ethyl]-benzooxazol-5-yl}-benzonitrile and

4-{2-[2-(2-(R)-methyl-pyrrolidin-1-yl)-ethyl]-benzooxazol-5-yl}benzonitrile

Example 24A 2-amino-4-bromo-phenol

4-Bromo-2-nitro-phenol (CAS #7693-52-9, from Aldrich) was reduced to 2-amino-4-bromo-phenol in 87% yield by the method described in D.A. Nugiel, K. Jacobs, L. Cornelius, C.-H. Chang, P.K. Jadhav, E.R. Holler, R.M. Klabe, L.T. Bacheler, B. Cordova, S. Garber, C. Reid, K.A. Logue, L.J. Gorey-Feret, G.N. Lam, S. Erickson-Vitanen, and S.P. Seitz, Journal of Medicinal Chemistry (1997) 40, 1465-474.

Example 24B 5-bromo-2-vinyl-benzooxazole

A mixture of 12 g of methanesulfonic acid and 1.8 g of phosphorus pentoxide ($P_2O_5$) was stirred 12 hours. To this well stirred suspension was added 0.346 g (4.8 mmol) of acrylic acid and 0.808 g (4 mmol) of 2-amino-4-bromo-phenol. The reaction was heated at 78° C. for 5 hours, then cooled to room temperature. The reaction was then slowly poured into a well-stirred slurry of 15 mL of 50% aqueous NaOH in 200 g of ice and water. The mixture was then poured into a separatory funnel and shaken with 300 mL water, 200 mL of diethyl ether, and 75 mL of dichloromethane and shaken vigorously. A small quantity of solid was removed by suction filtration, and the filtrate again shaken vigorously in a separatory funnel. The organic phase was collected, dried over $Na_2SO_4$, and concentrated in vacuo to a thick syrup that crystallized to give large yellow stars. Purification by flash chromatography on silica gel (eluting with 1:1 hexane: dichloromethane) gave 0.404 g (45%) of 5-bromo-2-vinyl-benzooxazole as a white powder, mp 55-56° C. $^1$H NMR (300 MHz, CDCl$_3$) δ 7.84 (d, J=1.8 Hz, 1 H), 7.46 (dd, J=8.7, 1.8 Hz, 1 H), 7.40 (d, J=8.7 Hz, 1 H), 6.76 (dd, J=17, 10.5 Hz, 1 H), 6.50 (d, J=17 Hz, 1 H), 5.90 (d, J=10.5 Hz, 1 H); Mass spectrum: [M+H]+ at 224.0 & 226.0.

Example 24C 4-(2-vinyl-benzooxazol-5-yl)-benzonitrile

A mixture of 224 mg (1 mmol) of 5-bromo-2-vinyl-benzooxazole, 191 mg (1.3 mmol) of 4-cyanophenylboronic acid, 55 mg (0.03 mmol) of tris-(dibenzylidineacetone)dipalladium (0) (CAS #52409-22-0), 0.2 mL (0.06 mmol) of a 10% solution of tri-tert-butylphosphine in hexane, and 1.5 mL of tetrahydrofuran was stirred at 23° C. for 24 hours. It was then heated at 65° C. for 0.5 hour, then cooled. The mixture was suction filtered to remove particulates, then partitioned between 80 mL of water and a mixture of 30 mL of ethyl acetate and 10 mL of hexane. The organic phase was collected, dried over $Na_2SO_4$, and purified by flash chromatography on silica gel (eluting with 1:1 hexane: dichloromethane) to give 4-(2-vinyl-benzooxazol-5-yl)-benzonitrile (192 mg, 78%) as a white solid: mp 143-144° C.; $^1$H NMR (300 MHz, CDCl$_3$) δ 7.90 (d, J=1.8 Hz, 1 H), 7.76 (d, J=8.4 Hz, 2 H), 7.70 (d, J=8.4 Hz, 2 H), 7.62 (d, J=7.5 Hz, 1 H), 7.55 (dd, J=7.5, 1.8 Hz, 1 H), 6.79 (dd, J=17.4, 10.5 Hz, 1 H), 6.52 (d, J=17.4 Hz, 1 H), 5.91 (d, J=10.5 Hz, 1 H); Mass spectrum: [M+H]$^+$247.1.

Example 24D

4-{2-[2-(2-methyl-pyrrolidin-1-yl)-ethyl]-benzooxazol-5-yl}-benzonitrile

A solution of 24.6 mg (0.1 mmol) of 4-(2-vinyl-benzooxazol-5-yl)-benzonitrile and 24 mg of racemic 2-methyl-pyrrolidine (Aldrich, CAS #765-38-8) in 0.25 mL of ethanol was stirred at room temperature for 1 hour, then concentrated in vacuo to a glass to give pure product racemic 4-{2-[2-(2-methyl-pyrrolidin-1-yl)-ethyl]-benzooxazol-5-yl}-benzonitrile 33 mg (100%): $^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 3.2-3.32 (m, 4 H), 1.44-2.65 (m, 7 H), 1.15 (m, 3H); Mass spectrum: [M+H]$^+$332.1.

Example 24E

4-{2-[2-(2-(R)-methyl-pyrrolidin-1-yl)-ethyl]-benzooxazol-5-yl}-benzonitrile

A solution of 2-(R)-methylpyrrolidine in di-isopropyl ether was prepared by adding 535 mg (2.28 mmol) of 2-(R)-methylpyrrolidine L-tartrate to a mixture of 2 mL of di-isopropyl ether and 2 mL of 12% aqueous NaOH. After shaking, the aqueous phase was removed. The organic phase was dried over $Na_2SO_4$, then added to a suspension of 140 mg (0.57 mmol) of 4-(2-vinyl-benzooxazol-5-yl)-benzonitrile in 2 mL of ethanol with stirring. After stirring vigorously at room temperature for 1.5 hours, the reaction was concentrated in vacuo to a glass which was purified by purified by flash chromatography on silica gel (eluting with 2% methanol/0.1% NH$_4$OH: dichloromethane) to give to give pure product as a clear glass that crystallized to give 187 mg (99%) of white solid 4-{2-[2-(2-(R)-methyl-pyrrolidin-1-yl)-ethyl]-benzooxazol-5-yl}-benzonitrile: mp 70-72° C.; $^1$H NMR (300 MHz, CD$_3$OD) δ 7.92 (m, 1 H), 7.82 (m, 4 H), 7.70 (m, 2 H), 3.2-3.45 (m, 4 H), 1.4-2.65 (m, 7 H), 1.15 (d, J=6 Hz, 3 H); Mass spectrum: [M+H]$^+$332.2.

Examples 25-48

Similar to the methods described above, vials containing 15 mg (0.061 mmol) of 4-(2-vinyl-benzooxazol-5-yl)-benzonitrile in 0.3 mL of methanol were treated with various amines or amine hydrochlorides (0.1 mL of Et$_3$N was used as co-additive for amine hydrochlorides). The reactions were stirred up to 5 days, and then concentrated under high vacuum to give products. The following examples show analogs prepared by this route.

Example 25

4-[2-(2-Pyrrolidin-1-yl-ethyl)-benzooxazol-5-yl]-benzonitrile

The title compound was prepared using pyrrolidine as the amine in 57% yield:

$^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz,

1 H), 7.50 (dd, J=7.5, 1.8 Hz), 3.25 (m, 1 H), 3.13 (m, 1 H), 2.7 (m, 4 H), 1.84 (m, 4H); Mass spectrum: [M+H]$^+$318.2.

Example 26

4-{2-[2-(2-(S)-methyl-pyrrolidin-1-yl)-ethyl]-benzooxazol-5-yl}-benzonitrile

The title compound was prepared using 2-(S)-methylpyrrolidine as the amine in 59% yield: $^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 3.2-3.32 (m, 4 H), 1.44-2.65 (m, 7 H), 1.15 (m, 3 H); Mass spectrum: [M+H]$^+$ 332.2.

Example 27

4-{2-[2-(3-(R)-Hydroxy-pyrrolidin-1-yl)-ethyl]-benzooxazol-5-yl}-benzonitrile

The title compound was prepared in 63% yield using 3-(R)-hydroxy-pyrrolidine as the amine: $^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 4.5 (m, 1 H), 3.4 (m, 2 H), 2.05-2.3 (m, 3 H), 1.85 (m, 4 H); Mass spectrum: [M+H]$^+$334.2.

Example 28

4-{2-[2-(2-(S)-Hydroxymethyl-pyrrolidin-1-yl)-ethyl]-benzooxazol-5-yl}-benzonitrile The title compound was prepared in 68% yield using 2-(S)-hydroxymethyl-pyrrolidine as the amine: $^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 3.8 (m, 2 H), 1.8-3.6 (m, 8 H), 1.60 (m, 4 H); Mass spectrum: [M+H]$^+$348.2.

Example 29

4-{2-[2-(2-(R),5-(R)-Dimethyl-pyrrolidin-1-yl)-ethyl]-benzooxazol-5-yl}-benzonitrile The title compound was prepared in 64% yield using 2-(R),5-(R)-dimethyl-pyrrolidine hydrochloride as the amine: $^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 3.4 (m, 4 H), 1.4-2.2 (m, 6 H), 1.2 (m, 6 H); Mass spectrum: [M+H]$^+$346.2.

Example 30

4-[2-(2-Piperidin-1-yl-ethyl)-benzooxazol-5-yl]-benzonitrile

The title compound was prepared using piperidine as the amine in 64% yield:
$^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 3.2 (m, 2 H), 3.0 (m, 2 H), 2.75 (m, 4 H), 1.4-1.65 (m, 6 H); Mass spectrum: [M+H]$^+$332.2.

Example 31

4-{2-[2-(2-(R)-methyl-piperidin-1-yl)-ethyl]-benzooxazol-5-yl}-benzonitrile

The title compound was prepared using 2-(R)-methylpiperidine L-tartrate in 61% yield: $^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 2.9-3.3 (m, 5 H), 2.4 (m, 2 H), 1.65 (m, 4 H), 1.3 (m, 2 H), 1.16 (d, J=6 Hz, 3 H);
Mass spectrum: [M+H]$^+$346.2.

Example 32

4-{2-[2-(2-(S)-Methoxymethyl-pyrrolidin-1-yl)-ethyl]-benzooxazol-5-yl}-benzonitrile The title compound was prepared in 65% yield using 2-(S)-methoxymethyl-pyrrolidine as the amine: $^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 3.35 (s, 3 H), 3.2-3.4 (m, 6 H), 2.4-2.9 (m, 3 H), 1.8-2 (m, 4 H); Mass spectrum: [M+H]$^+$362.2.

Example 33

4-[2-(2-Azepan-1-yl-ethyl)-benzooxazol-5-yl]-benzonitrile

The title compound was prepared using azepane as the amine in 64% yield:
$^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 3.2 (m, 4 H), 2.8 (m, 4 H), 1.6-1.75 (m, 8 H); Mass spectrum: [M+H]$^+$346.2.

Example 34

4-[2-(2-Diethylamino-ethyl)-benzooxazol-5-yl]-benzonitrile

The title compound was prepared using diethylamine in 90% yield: $^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 3.2 (m, 4 H), 2.7 (m, 4 H), 1.12 (t, J=6 Hz, 6 H); Mass spectrum: [M+H]$^+$320.2.

Example 35

4-{2-[2-(Isopropyl-methyl-amino)-ethyl]-benzooxazol-5-yl}-benzonitrile

The title compound was prepared using N-(methyl)isopropylamine in 61% yield: $^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 3.0-3.2 (m, 5 H), 2.39 (m, 2 H), 1.1 (m, 6 H); Mass spectrum: [M+H]$^+$ 320.2.

Example 36

4-{2-[2-(tert-Butyl-methyl-amino)-ethyl]-benzooxazol-5-yl}-benzonitrile

The title compound was prepared using N-(methyl) tert-butylamine in 57% yield: $^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 3.0-3.2 (m, 5 H), 2.35 (m, 2 H), 1.1 (m, 9 H); Mass spectrum: [M+H]⁺ 334.2

Example 37

4-{2-[2-(Butyl-methyl-amino)-ethyl]-benzooxazol-5-yl}-benzonitrile

The title compound was prepared using N-(methyl) butylamine in 70% yield:
$^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 3.0-3.2 (m, 3H), 2.45 (m, 4 H), 1.55 (m, 4 H), 1.35 (m, 2 H), 1.1 (t, J=6.3 Hz, 3 H); Mass spectrum: [M+H]⁺334.2

Example 38

4-{2-[2-(2-Hydroxymethyl-piperidin-1-yl)-ethyl]-benzooxazol-5-yl}-benzonitrile

The title compound was prepared using 2-hydroxymethyl-piperidine in 73% yield: $^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 4.0 (m, 1 H), 3.7 (m, 2 H), 3.4 (m, 5 H), 2.7-2.9 (m, 2 H), 1.7-1.9 (m, 6 H); Mass spectrum: [M+H]⁺362.2

Example 39

4-(2-{2-[2-(2-Hydroxy-ethyl)-piperidin-1-yl]-ethyl}-benzooxazol-5-yl)-benzonitrile The title compound was prepared using 2-hydroxyethyl-piperidine in 73% yield: $^1$H NMR (300 MHz, CDCl$_3$) δ 7.85 (d, J=1.8 Hz, 1H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 3.9 (m, 1 H), 3.78 (m, 1 H), 3.4 (m, 6 H), 1.75-2.05 (m, 10 H); Mass spectrum: [M+H]⁺376.2

Example 40

4-{2-[2-(2-Isopropyl-pyrrolidin-1-yl)-ethyl]-benzooxazol-5-yl}-benzonitrile

The title compound was prepared using racemic 2-isopropyl-pyrrolidine as the amine: $^1$H NMR (300 MHz, CDCl$_3$) δ 7.85 (d, J=1.8 Hz, 1 H), 7.77 (d, J=8.4 Hz, 2 H), 7.70 (d, J=8.4 Hz, 2 H), 7.58 (d, J=7.5 Hz, 1 H), 7.50 (dd, J=7.5, 1.8 Hz), 3.4 (m, 1 H), 3.1-3.25 (m, 3 H), 2.65 (m, 1 H), 2.2-2.28 (m, 2 H), 1.85 (m, 1 H), 1.5-1.7 (m, 4 H), 0.92 (d, J=6 Hz, 3 H), 0.88 (d, J=6 Hz, 3 H); Mass spectrum: [M+H]⁺360.2.

Example 41

4-{2-[2-(2-(R)-Methyl-azetidin-1-yl)-ethyl]-benzooxazol-5-yl}-benzonitrile

The title compound was prepared using 2-(R)-methyl-azetidine hydrochloride in 82% after chromatography (2% and then 5% (9:1 MeOH:conc NH$_4$OH) in CH$_2$Cl$_2$).
$^1$H NMR (300 MHz, CD$_3$OD) δ 1.23 (d, J=6 Hz, 3 H), 1.80 (m, 1 H), 2.12 (m, 1 H), 2.91 (m, 2 H), 3.05-3.20 (m, 3 H), 3.38 (m, 2 H), 7.69 (d, J=1 Hz, 2 H), 7.83 (m, 4 H), 7.92 (t, J=1 Hz, 1 H); Mass spectrum: [M+H]⁺318.

Example 42

4-{2-[2-(2-(S)-Fluoromethyl-azetidin-1-yl)-ethyl]-benzooxazol-5-yl}-benzonitrile The title compound was prepared using 2-(S)-fluoromethyl-azetidine hydrochloride in 80% after chromatography (2% and then 5% (9:1 MeOH:conc NH$_4$OH) in CH$_2$Cl$_2$). $^1$H NMR (300 MHz, CD$_3$OD) δ 1.96 (m, 2 H), 3.03 (m, 4 H), 3.17 (m, 1 H), 3.40 (td, J=7.63, 3.05 Hz, 1 H), 3.55 (m, 1 H), 4.32 (m, 1 H), 4.47 (m, 1 H), 7.69 (d, J=1.02 Hz, 2 H), 7.83 (m, 4 H), 7.92 (t, J=1.36 Hz, 1 H); Mass spectrum: [M+H]⁺336.

Example 43

4-{2-[2-(2-(S)-Hydroxymethyl-azetidin-1-yl)-ethyl]-benzooxazol-5-yl}-benzonitrile The title compound was prepared using 2-(S)-hydroxymethyl-azetidine hydrochloride in 79% after chromatography (2% and then 5% (9:1 MeOH:conc NH$_4$OH) in CH$_2$Cl$_2$). $^1$H NMR (300 MHz, CD$_3$OD) δ 1.92 (m, 1 H), 2.05 (m, 1 H), 2.97 (m, 2 H), 3.10 (m, 2 H), 3.20 (m, 1 H), 3.38 (m, 2 H), 3.56 (s, 1 H), 3.58 (d, J=2.03 Hz, 1 H), 7.68 (d, J=1.02 Hz, 2 H), 7.83 (m, 4 H), 7.92 (s, 1 H); Mass spectrum: [M+H]⁺334.

Example 44

4-[2-(2-Azetidin-1-yl-ethyl)-benzooxazol-5-yl]-benzonitrile

The title compound was prepared using azetidine in 85% after chromatography (2% and then 5% (9:1 MeOH:conc NH$_4$OH) in CH$_2$Cl$_2$); $^1$H NMR (300 MHz, CD$_3$OD) δ 2.10 (m, 2 H), 3.00 (m, 4 H), 3.30 (t, J=7.12 Hz, 4 H), 7.68 (d, J=1.36 Hz, 2 H), 7.82 (m, 4 H), 7.91 (t, J=1.19 Hz, 1 H); Mass spectrum: [M+H]⁺334.

Example 45

4-(2-{2-[cis-2,6-dimethyl-piperidin-1-yl]-ethyl}-benzooxazol-5-yl)-benzonitrile

The title compound was prepared using cis-2,6-dimethylpiperidine; [M+H]⁺360.

Example 46

4-(2-{2-[1,4,5,6-tetrahydropyrimidin-1-yl]-ethyl}-benzooxazol-5-yl)-benzonitrile The title compound was prepared using 1,4,5,6-tetrahydropyrimidine; [M+H]⁺331.

Example 47

4-(2-{2-[ethyl-isopropyl-amino]-ethyl}-benzooxazol-5-yl)-benzonitrile

The title compound was prepared using ethyl-isopropyl-amine; [M+H]⁺334.

Example 48

4-{2-[2-(2-methyl-prowl)-pyrrolidin-1-yl)-ethyl]-benzooxazol-5-yl}-benzonitrile

The title compound was prepared using 2-(2-methyl-propyl)pyrrolidine; [M+H]$^+$374.

Example 65

4-{1-Methyl-2-[2-(2-(R)-methyl-pyrrolidin-1-yl)-ethyl]-1H-indol-5-yl}-benzonitrile

Example 65A

1-But-3-ynyl-2-(R)-methyl-pyrrolidine

To a sealed flask was added 2-(R)-methylpyrrolidine L-tartrate (21.1 g, 90 mmol), 3-butynyl p-toluenesulfonate (15.7 mL, 89 mmol), potassium carbonate powder (18.5 g, 134 mmol) and $CH_3CN$ (160 mL). The resulting mixture was heated to 85° C. for 24 hours and the reaction was monitored by GC for the complete consumption of the tosylate. The reaction mixture was cooled to room temperature and filtered; the wet cake was washed with $CH_3CN$ (40 mL). The combined filtrate was used in the next step without further processing.

Example 65B

4-Bromo-2-[4-(2-(R)-methyl-pyrrolidin-1-yl)-but-1-ynyl]-phenylamine

To a solution of 1-butyn-3-yl-2-methyl-pyrrolidine in $CH_3CN$ (prepared in Example 65A assuming 100% conversion, 89 mmol) was added 4-bromo-2-iodo-phenylamine (12.0 g, 40 mmol) under nitrogen followed by addition of CuI (0.38 g, 2.0 mmol), $PdCl_2(PPh_3)_2$ (0.70 mg, 1.0 mmol) and diisopropylamine (33.6 mL, 240 mmol). The resulting solution was stirred at room temperature for 2 hours, at which time analytical HPLC analysis indicated that all 4-bromo-2-iodo-phenylamine was consumed. The solvent $CH_3CN$ was removed under vacuo and the residue was extracted with IPAC (500 mL) and 5% $NaHCO_3$ (2×300 mL). The organic layer was washed with brine, dried over $Na_2SO_4$ and concentrated under reduced pressure to give the title compound as a thick oil (11.96 g), which was used in the next step without further purification.

Example 65C

5-Bromo-2-[2-(2-(R)-methyl-pyrrolidin-1-yl)-ethyl]-1H-indole

To a cooled (0° C.) suspension of KO-tBu (95%, 7.8 g, 66 mmol) in NMP (150 mL) was added a solution of 4-bromo-2-[4-(2-methyl-pyrrolidin-1-yl)-but-1-ynyl]-phenylamine (10 g, 33 mmol) in NMP (50 mL) dropwise keeping the temperature below 5° C. The resulting mixture was then stirred at room temperature for 3 hours under nitrogen. HPLC indicated that all the starting material was consumed. $H_2O$ (400 mL) was added slowly to the reaction mixture followed by addition of IPAc (500 mL). The resulting mixture was stirred for 5 min. and the organic layer was separated. The organic layer was then washed with 20% brine (3×200 mL), dried over $Na_2SO_4$ and treated with activated carbon. After filtration, the filtrate was concentrated under reduced pressure to give the title compound as a thick oil (6.2 g), which was used in the next coupling reaction without further purification. $^1H$ NMR (400 MHz, $CDCl_3$) δ 10.21 (s, 1H), 7.73 (s, 1H), 7.27 (s, 2H), 6.24 (s, 1H), 3.42-3.50 (m, 1H), 3.21-3.28 (m, 1H), 2.97-3.10 (m, 2H), 2.49-2.60 (m, 2H), 2.33 (q, J=8.78 Hz, 1H), 2.10-2.17 (m, 1H), 1.87-2.02 (m, 2H), 1.58-1.67 (m, 1H), 1.24 (d, J=6.2 Hz, 3H). $^{13}C$ NMR (400 MHz, $CDCl_3$) δ 140.89, 133.92, 129.91, 122.98, 121.77, 112.16, 111.75, 98.32, 60.47, 53.60, 53.34, 33.19, 26.30, 22.14, 19.56. [M+H]$^+$ at m/z 307.

Example 65D

4-{2-[2-(2-(R)-Methyl-pyrrolidin-1-yl)-ethyl]-1H-indol-5-yl}-benzonitrile

A reaction flask was charged with $Cs_2CO_3$ (1.14 g, 3.5 mmol), CsF (0.38 g, 2.5 mmol), 4-cyanophenylboronic acid (425 mg, 2.5 mmol), and $H_2O$ (10 mL) followed by a toluene solution (10 mL) of 5-bromo-2-[2-(2-(R)-methyl-pyrrolidin-1-yl)-ethyl]-1H-indole (307 mg, 1.0 mmol). The resulting mixture was purged with nitrogen. To the reaction mixture was then added 2-dicyclohexylphosphino(biphenyl) (35 mg, 0.1 mmol) and $Pd_2(dba)_3$ (46 mg, 0.05 mmol). The resulting reaction mixture was then heated to 65° C. overnight under nitrogen after which HPLC indicated that all the 5-bromo-2-[2-(-(R)-methyl-pyrrolidin-1-yl-ethyl]-1H-indole was consumed. The reaction mixture was cooled to room temperature and IPAc (20 mL) was added. The organic layer was separated and concentrated. The residue was purified by column chromatography eluting with heptane/acetone/$CH_2Cl_2/Et_3N$ (600 mL/40 mL/5 mL/2 mL). The fractions containing product were combined and concentrated under reduced pressure to provide the title compound as a semi-solid (148 mg). $^1H$ NMR (400 MHz, $CDCl_3$) δ 10.22 (s, 1H), 7.65-7.74 (m, 5H), 7.40 (d, J=8.5 Hz, 1H), 7.33 (dd, J=1.8, 8.5 Hz, 1H), 6.27 (s, 1H), 3.37-3.42 (m, 1H), 3.21-3.25 (m, 1H), 3.01-3.16 (m, 2H), 2.54-2.62 (m, 2H), 2.33 (q, J=8.78 Hz, 1H), 2.04-2.08 (m, 1H), 1.80-1.93 (m, 2H), 1.56-1.63 (m, 1H), 1.21 (d, J=6.2 Hz, 3H). $^{13}C$ NMR (400 MHz, $CDCl_3$) δ 146.99, 139.96, 135.61, 132.05, 130.30, 128.74, 127.32, 120.02, 119.13, 118.36, 111.13, 109.16, 99.49, 61.25, 53.68, 53.57, 32.92, 26.21, 22.14, 18.98. [M+H]$^+$ at m/z 330.

Example 65E

4-{2-[2-(2-(R)-Methyl-pyrrolidin-1-yl)-ethyl]-1H-indol-5-yl}-benzonitrile HCl

The free base 4-{2-[2-(2-Methyl-pyrrolidin-1-yl)-ethyl]-1H-indol-5-yl}-benzonitrile (148 mg) was dissolved in EtOAc (3 mg), to the solution was added a 4N HCl solution in dioxane (0.3 mL). The HCl salt precipitated out and was collected by filtration to give 135 mg HCl salt as solid.

Example 65F

5-Bromo-1-methyl-2-[2-(2-(R)-methyl-pyrrolidin-1-yl)-ethyl]-1H-indole

To a cooled (0° C.) suspension of KO-tBu (95%, 6.2 g, 52 mmol) in NMP (120 mL) was added a solution of 4-bromo-2-[4-(2-(R)-methyl-pyrrolidin-1-yl)-but-1-ynyl]-phenylamine (8.0 g, 26 mmol) in NMP (50 mL) dropwise keeping the temperature below 5° C. The resulting mixture was then stirred at room temperature for 3 hours under nitrogen. HPLC indicated that all the starting material was consumed. MeI (1.95 mL, 31.3 mmol) was then added. The resulting mixture was stirred at room temperature for 2 hours. HPLC indicated that all the indole intermediate was methylated. $H_2O$ (300 mL) was added slowly to the reaction mixture followed by addition of IPAc (400 mL). The resulting mixture was stirred for 5 minutes and the organic layer was separated. The organic layer was washed with 20% brine (3×150 mL), dried over $Na_2SO_4$ and treated with activated carbon. After filtration, the filtrate was concentrated under vacuum to give the title compound as a thick oil (7.5 g), which was used in the next coupling reaction without further purification. $^1$H NMR (400 MHz, $CDCl_3$) δ 7.78 (d, J=1.8 Hz, 1H), 7.36 (dd, J=1.8, 8.7 Hz, 1H), 7.26 (d, J=8.6 Hz, 1H), 6.37 (s, 1H), 3.81 (s, 1H), 3.40-3.45 (m, 1H), 3.26-3.34 (m, 1H), 3.04-3.16 (m, 2H), 2.51-2.61 (m, 2H), 2.39 (q, J=8.78 Hz, 1H), 2.09-2.14 (m, 1H), 1.87-1.99 (m, 2H), 1.61-1.68 (m, 1H), 1.30 (d, J=6.2 Hz, 3H). $^{13}$C NMR (400 MHz, $CDCl_3$) δ 140.30, 135.60, 129.18, 123.08, 121.92, 112.29, 109.95, 98035, 60.16, 54.22, 53.19, 32091, 29.86, 26.85, 22.00, 19.34. $[M+H]^+$ at m/z 322.

Example 65G

4-{1-Methyl-2-[2-(2-(R)-methyl-pyrrolidin-1-yl)-ethyl]-1H-indol-5-yl}-benzonitrile A reaction flask was charged with $Cs_2CO_3$ (1.14 g, 3.5 mmol), CsF (0.38 g, 2.5 mmol), 4-cyanophenylboronic acid (425 mg, 2.5 mmol), and $H_2O$ (10 mL) followed by a toluene solution (10 mL) of 5-bromo-1-methyl-2-[2-(2-methyl-pyrrolidin-1-yl)ethyl]-1H-indole (320 mg, 1.0 mmol). The resulting mixture was purged with nitrogen. To the reaction mixture was then added $Cy_2PPh_2$(5-bromo-2-[2-(R)-methyl-pyrrolidin-1-yl)-ethyl]-1H-indole) (35 mg, 0.1 mmol) and $Pd_2(dba)_3$ (46 mg, 0.05 mmol). The resulting reaction mixture was then heated to 65° C. overnight under nitrogen. HPLC indicated that all of the 5-bromo-1-methyl-2-[2-(2-methyl-pyrrolidin-1-yl)-ethyl]-1H-indole was consumed. The reaction mixture was cooled to room temperature and IPAc (20 mL) was added. The organic layer was separated and concentrated. The residue was purified by column chromatograph eluting with heptane/acetone/$CH_2Cl_2$/$Et_3N$ (600 mL/40 mL/5 mL/2 mL). The fractions containing product were combined and concentrated under reduced pressure to provide the title compound as a semi-solid (154 mg). $^1$H NMR (400 MHz, $CDCl_3$) δ 7.57-7.66 (m, 5H), 7.30 (dd, J=1.7, 8.6 Hz, 1H), 7.25 (d, J=8.51 Hz, 1H), 6.27 (S, 1H), 3.63 (S, 1H), 3.21-3.25 (m, 1H), 3.06-3.13 (m, 1H), 2.87-2.93 (m, 2H), 2.33-2.40 (m, 2H), 2.16 (q, J=8.78 Hz, 1H), 1.84-1.91 (m, 1H), 1.65-1.76 (m, 2H), 1.36-1.44 (m, 1H), 1.07 (d, J=6.1 Hz, 3H). $^{13}$C NMR (400 MHz, $CDCl_3$) δ 146.80, 140.39, 137.11, 132.04, 130.19, 128.11, 127.27, 119.86, 119.08, 118.43, 109.18, 99.37, 60.15, 54.19, 53.24, 32.89, 29.91, 26.85, 21.98, 19.32. $[M+H]^+$ at m/z 344.

Example 66

3-{1-Methyl-2-[2-(2-(R)-methyl-pyrrolidin-1-yl)-ethyl]-1H-indol-5-yl}-benzonitrile The title compound was prepared by the procedure described for Example 65G, except substituting 4-cyanophenylboronic acid with 3-cyanophenylboronic acid.
$^1$H NMR (400 MHz, $CDCl_3$) δ 7.82 (m, 1H), 7.75-7.78 (m, 1H), 7.63 (t, 1H), 7.40-7.48 (m, 2H), 7.27 (d, J=1.8 Hz, 2H), 6.28 (s, 1H), 3.65 (S, 1H), 3.21-3.25 (m, 1H), 3.08-3.15 (m, 1H), 2.89-2.98 (m, 2H), 2.33-2.42 (m, 2H), 2.18 (q, J=8.78 Hz, 1H), 1.87-1.94 (m, 1H), 1.66-1.88 (m, 2H), 1.08 (d, J=6.2 Hz, 3H). $^{13}$C NMR (400 MHz, $CDCl_3$) δ 143.52, 140.31, 136.94, 131.23, 130.40, 129.18, 129.02, 128.13, 119.77, 118.95, 112.41, 109.20, 99.30, 60.19, 54.21, 53.28, 32.91, 29.92, 26.86, 22.00, 19.32. $[M+H]^+$ at m/z 344.

Example 67

3-{2-[2-(2-(R)-Methyl-pyrrolidin-1-yl)-ethyl]-1H-indol-5-yl}-benzonitrile

The title compound was prepared by the procedure described for Example 65D, except substituting 4-cyanophenylboronic acid with 3-cyanophenylboronic acid.
$^1$H NMR (400 MHz, $CDCl_3$) δ 10.07 (s, 1H), 7.82 (m, 1H), 7.76 (t, J=7.7 Hz, 1H), 7.63 (d, J=1.7 Hz, 1H), 7.38-7.47 (m, 2H), 7.31 (d, J=8.4 Hz, 1H), 7.21 (dd, J=1.8, 8.4 Hz, 1H), 6.19 (s, 1H), 3.29 (m, 1H), 3.09 (m, 1H), 2.85-2.95 (m, 2H), 2.33-2.45 (m, 2H), 2.17 (q, J=8.78 Hz, 1H), 1.90-1.97 (m, 1H), 1.70-1.82 (m, 2H), 1.44-1.49 (m, 1H), 1.21 (d, J=6.0 Hz, 3H). $^{13}$C NMR (400 MHz, $CDCl_3$) δ 143.69, 140.77, 135.34, 131.24, 130.39, 129.97, 128.98, 128.77, 119.72, 118.98, 118.07, 112.35, 110.98, 99.17, 60.54, 53.63, 53.45, 33.18, 26.42, 22.15, 19.52. $[M+H]^+$ at m/z 330.

Example 68

5-(4-Fluoro-phenyl)-2-[2-(2-(R)-methyl-pyrrolidin-1-yl)-ethyl]-1H-indole

The title compound was prepared by the procedure described for Example 65D, except substituting 4-cyanophenylboronic acid with 4-fluorophenylboronic acid.
$^1$H NMR (400 MHz, $CDCl_3$) δ 9.90 (s, 1H), 7.59 (s, 1H), 7.46-7.50 (m, 2H), 7.26 (d, J=8.3 Hz, 1H), 7.20 (dd, J=1.7, 8.3 Hz, 1H), 7.01 (t, J=8.7 Hz, 1H), 7.21 (dd, J=1.8, 8.4 Hz, 1H), 6.16 (s, 1H), 3.25-3.30 (m, 1H), 3.04-3.11 (m, 1H), 2.82-2.94 (m, 2H), 2.30-2.42 (m, 2H), 2.16 (q, J=8.78 Hz, 1H), 1.90-1.98 (m, 1H), 1.69-1.84 (m, 2H), 1.43-1.50 (m, 1H), 1.05 (d, J=6.2 Hz, 3H). $^{13}$C NMR (400 MHz, $CDCl_3$) δ 162.53, 160.12, 140.37, 138.68, 134.82, 131.53, 128.66, 128.33, 120.04, 117.84, 115.13, 114.92, 110.61, 99.00, 60.51, 53.68, 53.53, 33.21, 26.52, 22.17, 19.59. $[M+H]^+$ at m/z 323.

Example 69

5-(3,5-Difluoro-phenyl)-2-[2-(2-(R)-methyl-pyrrolidin-1-yl)-ethyl]-1H-indole

The title compound was prepared by the procedure described for Example 65D, except substituting 4-cyanophenylboronic acid 3,5-difluorophenylboronic acid.
$^1$H NMR (400 MHz, $CDCl_3$) δ 10.04 (s, 1H), 7.62 (s, 1H), 7.27 (d, J=8.3 Hz, 1H), 7.20 (dd, J=1.7, 8.3 Hz, 1H), 7.06 (m, 1H), 6.62 (m, 1H), 6.17 (s, 1H), 3.26-3.30 (m, 1H), 3.05-3.10 (m, 1H), 2.83-2.97 (m, 2H), 2.32-2.43 (m, 2H), 2.16 (q, J=8.78 Hz, 1H), 1.92-1.98 (m, 1H), 1.69-1.81 (m, 2H), 1.42-1.49 (m, 1H), 1.05 (d, J=6.2 Hz, 3H). $^{13}$C NMR (400 MHz, $CDCl_3$) δ 164.00 (d), 161.56 (d), 145.94, 140.73, 135.42, 130.09, 128.66, 119.70, 117.99, 110.81, 109.70 (d), 100.94 (t), 99.19, 60.52, 53.68, 53.47, 33.21, 26.45, 22.17, 19.56. $[M+H]^+$ at m/z 341.

Example 70

2-[2-(2-(R)-Methyl-pyrrolidin-1-yl)-ethyl]-5-(4-trifluoromethoxy-phenyl)-1H-indole The title compound was prepared by the procedure described for Example 65D, except substituting 4-cyanophenylboronic acid 4-trifluoromethoxyphenylboronic acid. $^1$H NMR (400 MHz, CDCl$_3$) δ 9.96 (s, 1H), 7.61 (s, 1H), 7.53 (d, J=12 Hz, 2H), 7.27 (d, J=8.2 Hz, 1H), 7.21 (dd, J=1.8, 8.4 Hz, 1H), 7.16 (d, J=8.6 Hz, 2H), 6.17 (s, 1H), 3.26-3.31 (m, 1H), 3.05-3.12 (m, 1H), 2.84-2.95 (m, 2H), 2.32-2.44 (m, 2H), 2.16 (q, J=8.78 Hz, 1H), 1.90-1.98 (m, 1H), 1.69-1.81 (m, 2H), 1.44-1.50 (m, 1H), 1.06 (d, J=3.5 Hz, 3H). $^{13}$C NMR (400 MHz, CDCl$_3$) δ 147.40, 141.36, 140.41, 135.05, 131.08, 128.70, 128.13, 121.60, 120.79, 120.04, 119.07, 118.01, 110.74, 99.11, 60.61, 53.66, 53.53, 33.19, 26.47, 22.17, 19.51. [M+H]$^+$ at m/z 389.

Example 71

2-[2-(2-(R)-Methyl-pyrrolidin-1-yl)-ethyl]-5-pyridin-3-yl-1H-indole

The title compound was prepared by the procedure described for Example 65D, except substituting 4-cyanophenylboronic acid with 3-pyridinylboronic acid. $^1$H NMR (400 MHz, CDCl$_3$) δ 10.29 (s, 1H), 8.79 (s, 1H), 8.44 (d, J=4.0 Hz, 1H), 7.82 (d, J=8.0 Hz, 1H), 7.63 (s, 1H), 7.38 (d, J=8.2 Hz, 1H), 7.25 (m, 2H), 6.22 (s, 1H), 3.38-3.46 (m, 2H), 3.05-3.18 (m, 2H), 2.76-2.90 (m, 2H), 2.57 (q, J=8.78 Hz, 1H), 2.03-2.09 (m, 1H), 1.90-1.98 (m, 1H), 1.80-1.86 (m, 1H), 1.61-1.68 (m, 1H), 1.28 (d, J=6.3 Hz, 3H). $^{13}$C NMR (400 MHz, CDCl$_3$) δ 147.90, 146.77, 137.76, 136.70, 135.76, 134.10, 128.95, 128.69, 123.17, 120.46, 118.14, 111.58, 100.15, 63.18, 53.67, 53.13, 31.91, 25.73, 21.86, 16.81. [M+H]$^+$ at m/z 306.

Example 72

1-(3-{2-[2-(2-(R)-Methyl-pyrrolidin-1-yl)-ethyl]-1H-indol-5-yl}-phenyl)-ethanone The title compound was prepared by the procedure described for Example 65D, except substituting 4-cyanophenylboronic acid 3-acetylphenylboronic acid. $^1$H NMR (400 MHz, CDCl$_3$) δ 9.95 (s, 1H), 8.13 (s, 1H), 7.73-7.78 (m, 2H), 7.67 (s, 1H), 7.40 (t, J=8.2 Hz, 1H), 7.28 (s, 2H), 6.18 (s, 1H), 3.23-3.28 (m, 1H), 3.03-3.09 (m, 1H), 2.81-2.93 (m, 2H), 2.56 (s, 3H), 2.29-2.41 (m, 2H), 2.13 (q, J=8.78 Hz, 1H), 1.88-1.96 (m, 1H), 1.67-1.79 (m, 2H), 1.39-1.48 (m, 1H), 1.04 (d, J=6.3 Hz, 3H). $^{13}$C NMR (400 MHz, CDCl$_3$) δ 197.75, 142.94, 140.50, 137.08, 135.11, 131.58, 131.27, 128.72, 128.44, 126.79, 125.63, 119.99, 118.04, 110.73, 99.08, 60.42, 53.64, 53.48, 33.18, 27.02, 26.53, 27.02, 26.53, 22.13, 19.57. [M+H]$^+$ at m/z 347.

Example 73

5-Furan-2-yl-2-[2-(2-(R)-methyl-pyrrolidin-1-yl)-ethyl]-1H-indole

The title compound was prepared by the procedure described for Example 65D, except substituting 4-cyanophenylboronic acid 5-furanylboronic acid. $^1$H NMR (400 MHz, CDCl$_3$) δ 9.88 (s, 1H), 7.76 (s, 1H), 7.34-7.37 (m, 2H), 7.20-7.22 (M, 1H), 6.45 (dd, J=0.82, 3.29 Hz, 1H), 6.36 (dd, J=1.92, 3.29 Hz, 1H), 6.14 (s, 1H), 3.24-3.29 (m, 1H), 3.04-3.09 (m, 1H), 2.80-2.92 (m, 2H), 2.28-2.41 (m, 2H), 2.14 (q, J=8.78 Hz, 1H), 1.82-1.98 (m, 1H), 1.65-1.78 (m, 2H), 1.42-1.49 (m, 1H), 1.05 (d, J=6.0 Hz, 3H). $^{13}$C NMR (400 MHz, CDCl$_3$) δ155.44, 140.48, 140.25, 134.91, 128.31, 122.55, 117.33, 115.05, 111.05, 111.20, 110.55, 99.15, 60.48, 53.66, 53.45, 33.21, 26.49, 22.15, 19.59. [M+H]$^+$ at m/z 275.

Example 74

5-(2,6-Difluoro-pyridin-3-yl)-2-[2-(2-(R)-methyl-pyrrolidin-1-yl)-ethyl]-1H-indole The title compound was prepared by the procedure described for 65D, except substituting 4-cyanophenylboronic acid (2,6-difluoro-3-pyridinyl)boronic acid. $^1$H NMR (400 MHz, CDCl$_3$) δ 10.08 (s, 1H), 7.88 (m, 1H), 7.57 (s, 1H), 7.28 (d, J=12 Hz, 1H), 7.14 (m, 1H), 6.77 (dd, J=3.02, 8.10 Hz, 1H), 6.16 (s, 1H), 3.24-3.29 (m, 1H), 3.03-3.09 (m, 1H), 2.80-2.92 (m, 2H), 2.30-2.42 (m, 2H), 2.14 (q, J=8.78 Hz, 1H), 1.91-1.97 (m, 1H), 1.70-1.89 (m, 2H), 1.39-1.49 (m, 1H), 1.05 (d, J=6.0 Hz, 3H). $^{13}$C NMR (400 MHz, CDCl$_3$) δ 160.32 (d), 158.00 (dd), 156.21 (d), 144.69 (m), 140.78, 135.16, 128.43, 126.60, 121.04, 119.82, 110.64, 105.74 (d), 99.03, 60.44, 53.64, 53.45, 33.20, 26.43, 22.15, 19.59. [M+H]$^+$ at m/z 342.

Example 75

5-(6-Methoxy-pyridin-3-yl)-2-[2-(2-(R)-methyl-pyrrolidin-1-yl)-ethyl]-1H-indole

The title compound was prepared by the procedure described for 65D, except substituting 4-cyanophenylboronic acid with (6-methoxy-3-pyridinyl)boronic acid. $^1$H NMR (400 MHz, CDCl$_3$) δ 9.93 (s, 1H), 7.73 (dd, J=2.54, 8.58 Hz, 1H), 7.56 (s, 1H), 7.27 (d, J=8.37 Hz, 1H), 7.16 (dd, J=1.78, 8.37 Hz, 1H), 6.70 (d, J=8.58 Hz, 1H), 6.16 (s, 1H), 3.89 (s, 3H), 3.24-3.29 (m, 1H), 3.03-3.06 (m, 1H), 2.82-2.93 (m, 2H), 2.29-2.41 (m, 2H), 2.13 (q, J=8.78 Hz, 1H), 1.88-1.96 (m, 1H), 1.67-1.79 (m, 2H), 1.41-1.48 (m, 1H), 1.04 (d, J=6.0 Hz, 3H). $^{13}$C NMR (400 MHz, CDCl$_3$) δ 162.35, 144.44, 140.47, 137.44, 134.85, 131.51, 128.99, 128.75, 119.68, 117.54, 110.79, 110.23, 98.96, 60.43, 53.67, 53.51, 33.20, 26.55, 22.15, 19.595. [M+H]$^+$ at m/z 336.

Example 76

5-(4-Methanesulfonyl-phenyl)-2-[2-(2-(R)-methyl-pyrrolidin-1-yl)-ethyl]-1H-indole The title compound was prepared by the procedure described for 65D, except substituting 4-cyanophenylboronic acid with 4-methanesulfonylphenylboronic acid.
$^1$H NMR (400 MHz, CDCl$_3$) δ 10.09 (s, 1H), 7.86 (m, 2H), 7.68-7.72 (m, 3H), 7.25-7.32 (m, 2H), 6.19 (s, 1H), 3.25-3.30 (m, 1H), 3.04-3.11 (m, 1H), 3.00 (s, 3H), 2.84-2.95 (m, 2H), 2.32-2.44 (m, 2H), 2.16 (q, J=8.78 Hz, 1H), 1.90-1.97 (m, 1H), 1.70-1.81 (m, 2H), 1.43-1.48 (m, 1H), 1.06 (d, J=6.2 Hz, 3H). $^{13}$C NMR (400 MHz, CDCl$_3$) δ 148.04, 140.82, 137.19, 135.56, 130.04, 128.75, 127.47, 127.34, 119.95, 118.45, 110.89, 99.22, 60.47, 53.62, 53.41, 44.82, 33.15, 26.43, 22.12, 19.52. [M+H]$^+$ at m/z 383.

Example 77

5-(2,6-Dimethyl-pyridin-3-yl)-2-[2-(2-(R)-methyl-pyrrolidin-1-yl)-ethyl]-1H-indole The title compound was prepared by the procedure described for 65D, except substituting 4-cyanophenylboronic acid (2,6-dimethyl-3-pyridinyl)boronic acid. $^1$H NMR (400

MHz, CDCl₃) δ 10.03 (s, 1H), 7.39 (d, J=7.82 Hz, 1H), 7.34 (d, J=1.10 Hz, 1H), 7.25 (d, J=8.37 Hz, 1H), 6.93-6.95 (m, 2H), 6.15 (s, 1H), 3.25-3.30 (m, 1H), 3.06-3.13 (m, 1H), 2.84-2.95 (m, 2H), 2.49 (s, 3H), 2.43 (s, 3H), 2.30-2.40 (m, 2H), 2.15 (q, J=8.78 Hz, 1H), 1.90-1.98 (m, 1H), 1.68-1.84 (m, 2H), 1.43-1.49 (m, 1H), 1.06 (d, J=6.2 Hz, 3H). ¹³C NMR (400 MHz, CDCl₃) δ 154.98, 154.83, 140.31, 137.83, 135.19, 134.50, 130.81, 128.11, 121.78, 120.18, 119.83, 110.13, 98.79, 60.45, 53.64, 53.50, 33.20, 26.52, 24.28, 23.45, 22.14, 19.59. [M+H]⁺ at m/z 334.

Example 78

1-(4-{2-[2-(2-(R)-Methyl-pyrrolidin-1-yl)-ethyl]-1H-indol-5-yl}-phenyl)-ethanone The title compound was prepared by the procedure described for 65D, except substituting 4-cyanophenylboronic acid with 4-acetylphenylboronic acid. ¹H NMR (400 MHz, CDCl₃) δ 10.02 (s, 1H), 7.92 (d, J=8.65 Hz, 2H), 7.71 (s, 1H), 7.63 (d, J=8.64 Hz, 2H), 7.30 (d, J=1.23 Hz, 2H), 6.19 (s, 1H), 3.25-3.30 (m, 1H), 3.04-3.11 (m, 1H), 2.83-2.94 (m, 2H), 2.54 (s, 3H), 2.31-2.43 (m, 2H), 2.15 (q, J=8.78 Hz, 1H), 1.91-1.98 (m, 1H), 1.69-1.83 (m, 2H), 1.40-1.48 (m, 1H), 1.06 (d, J=6.0 Hz, 3H). ¹³C NMR (400 MHz, CDCl₃) δ 197.24, 147.22, 140.60, 135.43, 134.38, 130.89, 128.49, 126.80, 120.04, 118.29, 110.82, 99.22, 60.49, 53.66, 53.48, 33.17, 26.85, 26.51, 22.14, 19.54. [M+H]⁺ at m/z 347.

Example 79

5-(3-Fluoro-phenyl)-2-[2-(2-(R)-methyl-pyrrolidin-1-yl)-ethyl]-1H-indole

The title compound was prepared by the procedure described for 65D, except substituting 4-cyanophenylboronic acid with 3-fluorophenylboronic acid. ¹H NMR (400 MHz, CDCl₃) δ 9.95 (s, 1H), 7.64 (s, 1H), 7.23-7.34 (m, 5H), 6.85-6.91 (m, 1H), 6.18 (s, 1H), 3.25-3.30 (m, 1H), 3.04-3.11 (m, 1H), 2.82-2.98 (m, 1H), 2.29-2.43 (m, 2H), 2.15 (q, J=8.78 Hz, 1H), 1.90-1.98 (m, 1H), 1.69-1.83 (m, 2H), 1.41-1.50 (m, 1H), 1.06 (d, J=6.0 Hz, 3H). ¹³C NMR (400 MHz, CDCl₃) δ 163.88, 161.46, 144.91, 140.50, 135.16, 131.16, 129.58, 129.49, 128.66, 122.56, 119.97, 118.00, 113.87, 113.65, 112.57, 110.69, 99.11, 60.48, 53.67, 53.51, 33.21, 26.52, 22.16, 19.59. [M+H]⁺ at m/z 323.

Example 80

Dimethyl-(4-{2-[2-(2-(R)-methyl-pyrrolidin-1-yl)-ethyl]-1H-indol-5-yl}-phenyl)-amine The title compound was prepared by the procedure described for 65D, except substituting 4-cyanophenylboronic acid with 4-dimethylphenylboronic acid. ¹H NMR (400 MHz, CDCl₃) δ 9.74 (s, 1H), 7.49 (dd, J=0.82, 8.92 Hz, 2H), 7.27 (s, 1H), 6.78 (d, J=8.51 Hz, 2H), 6.18 (s, 1H), 3.28-3.33 (m, 1H), 3.07-3.12 (m, 1H), 2.85-2.99 (m, 2H), 2.93 (s, 6H), 2.35-2.45 (m, 2H), 2.15 (q, J=8.78 Hz, 1H), 1.92-2.00 (m, 1H), 1.71-1.84 (m, 2H), 1.46-1.50 (m, 1H), 1.09 (d, J=6.0 Hz, 3H). ¹³C NMR (400 MHz, CDCl₃) δ 148.88, 139.82, 134.37, 132.61, 131.19, 128.68, 127.55, 119.88, 117.05, 112.82, 110.40, 98.92, 60.48, 53.70, 53.60, 41.00, 33.19, 26.63, 22.15, 19.56. [M+H]⁺ at m/z 348.

Example 81

5-(4-Chloro-phenyl)-2-[2-(2-(R)-methyl-pyrrolidin-1-yl)-ethyl]-1H-indole

The title compound was prepared by the procedure described for 65D, except substituting 4-cyanophenylboronic acid with 4-chlorophenylboronic acid. ¹H NMR (400 MHz, CDCl₃) δ 9.92 (s, 1H), 7.58 (d, J=0.82 Hz, 1H), 7.43-7.45 (m, 2H), 7.24-7.28 (m, 3H), 7.18-7.20 (m, 1H), 6.14 (s, 1H), 3.23-3.28 (m, 1H), 3.02-3.09 (m, 1H), 2.82-2.95 (m, 2H), 2.30-2.41 (m, 2H), 2.13 (q, J=8.78 Hz, 1H), 1.88-1.96 (m, 1H), 1.67-1.82 (m, 2H), 1.39-1.48 (m, 1H), 1.04 (d, J=6.0 Hz, 3H). ¹³C NMR (400 MHz, CDCl₃) δ 140.99, 140.35, 135.02, 131.67, 131.18, 128.69, 128.30, 128.17, 119.93, 117.85, 110.71, 99.09, 60.57, 53.67, 53.53, 33.17, 26.49, 22.15, 19.50. [M+H]⁺ at m/z 339.

Example 82

5-(2,4-Dimethoxy-pyrimidin-5-yl)-2-[2-(2-(R)-methyl-pyrrolidin-1-yl)-ethyl]-1H-indole The title compound was prepared by the procedure described for 65D, except substituting 4-cyanophenylboronic acid with 2,4-dimethoxy-5-pyrimidinyboronic acid. ¹H NMR (400 MHz, CDCl₃) δ 9.92 (s, 1H), 8.19 (s, 1H), 7.52 (m, 1H), 7.25-7.27 (m, 1H), 7.11 (dd, J=1.78, 8.37 Hz, 1H), 6.14 (s, 1H), 3.95 (s, 3H), 3.93 (s, 3H), 3.25-3.28 (m, 1H), 3.02-3.08 (m, 1H), 2.82-2.97 (m, 2H), 2.29-2.41 (m, 2H), 2.14 (q, J=8.78 Hz, 1H), 1.89-1.96 (m, 1H), 1.66-1.82 (m, 2H), 1.39-1.48 (m, 1H), 1.04 (d, J=6.0 Hz, 3H). ¹³C NMR (400 MHz, CDCl₃) δ 167.76, 163040, 156.90, 140.28, 134.91, 128.30, 123.77, 121.50, 119.85, 117.54, 110.27, 98.94, 60.42, 54.78, 54.08, 53.67, 53.55, 33.18, 26.55, 22.13, 19.56. [M+H]⁺ at m/z 367.

Example 83

2-[2-(2-(R)-Methyl-pyrrolidin-1-yl)-ethyl]-5-(3-trifluoromethyl-phenyl)-1H-indole The title compound was prepared by the procedure described for 65D, except substituting 4-cyanophenylboronic acid with 3-trifluorophenylboronic acid. ¹H NMR (400 MHz, CDCl₃) δ 10.00 (s, 1H), 7.61-7.65 (m, 3H), 7.54 (d, J=8.23 Hz, 2H), 7.23-7.29 (m, 2H), 6.17 (s, 1H), 3.24-3.29 (m, 1H), 3.04-3.10 (m, 1H), 2.82-2.97 (m, 2H), 2.30-2.43 (m, 2H), 2.13 (q, J=8.78 Hz, 1H), 1.91-1.96 (m, 1H), 1.68-1.83 (m, 2H), 1.40-1.47 (m, 1H), 1.05 (d, J=6.0 Hz, 3H). ¹³C NMR (400 MHz, CDCl₃) δ 146.02, 140.53, 135.34, 130.91, 128.74, 127.07, 125.19, 125.11, 120.07, 118.27, 110.56, 99.22, 60.62, 53.67, 53.52, 33.17, 26.46, 22.17, 19.48. [M+H]⁺ at m/z 373.

Example 84

2-Methyl-5-{2-[2-(2-(R)-methyl-pyrrolidin-1-yl)-ethyl]-1H-indol-5-yl}-benzothiazole The title compound was prepared by the procedure described for 65D, except substituting 4-cyanophenylboronic acid with 2-methyl-5-(4,4,5,5-tetramethyl-[1,3,2]dioxaborolan-2-yl)-benzothiazole. ¹H NMR (400 MHz, CDCl₃) δ 9.87 (s, 1H), 8.08 (d, J=1.51 Hz, 1H), 7.67-7.72 (m, 2H), 7.52 (dd, J=1.78, 8.23 Hz, 1H), 7.25-7.30 (m, 2H), 6.15 (s, 1H), 3.21-3.26 (m, 1H), 3.02-3.08 (m, 1H), 2.79-2.93 (m, 2H), 2.73 (s, 3H), 2.26-2.38 (m, 2H), 2.10 (q, J=8.64 Hz, 1H), 1.85-1.91 (m, 1H), 1.63-1.80 (m, 2H), 1.36-1.44 (m, 1H), 1.01 (d, J=6.0 Hz, 3H). $^{13}$C NMR (400 MHz, CDCl$_3$) δ 166.68, 153.65, 140.97, 140.33, 134.97, 133.00, 131.99, 128.74, 124.39, 120.91, 120.45, 120.36, 118.21, 110.72, 99.12, 60.48, 53.68, 53.54, 33.19, 26.57, 22.15, 20.47, 19.56. [M+H]$^+$ at m/z 376.

Example 85

8-{2-[2-(2-(R)-Methyl-pyrrolidin-1-yl)-ethyl]-1H-indol-5-yl}-quinoline

The title compound was prepared by the procedure described for 65D, except substituting 4-cyanophenylboronic acid with 8-quinolinylboronic acid. $^1$H NMR (400 MHz, CDCl$_3$) δ 9.68 (s, 1H), 8.00 (dd, J=1.78, 4.12 Hz, 1H), 8.03 (dd, J=1.92, 8.23 Hz, 1H), 7.62-7.67 (m, 3H), 7.44 (dd, J=7.00, 8.23 Hz, 1H), 7.22-7.33 (m, 3H), 6.13 (s, 1H), 3.20-3.25 (m, 1H), 2.97-3.03 (m, 1H), 2.76-2.92 (m, 2H), 2.22-2.36 (m, 2H), 2.08 (q, J=8.78 Hz, 1H), 1.83-1.90 (m, 1H), 1.63-1.78 (m, 2H), 1.36-1.44 (m, 1H), 1.00 (d, J=6.0 Hz, 3H). $^{13}$C NMR (400 MHz, CDCl$_3$) δ149.50, 146.11, 142.20, 139.58, 135.74, 135.04, 130.39, 130.13, 128.42, 126.22, 125.92, 123.60, 121.35, 120.40, 109.74, 99.19, 60.45, 53.75, 53.72, 33.17, 26.72, 22.14, 19.54. [M+H]$^+$ at m/z 356.

Example 86

5-{2-[2-(2-(R)-Methyl-pyrrolidin-1-yl)-ethyl]-1H-indol-5-yl}-nicotinonitrile

The title compound was prepared by the procedure described for 65D, except substituting 4-cyanophenylboronic acid with 5-(4,4,5,5-tetramethyl-[1,3,2]dioxaborolan-2-yl)-nicotinonitrile. $^1$H NMR (400 MHz, CDCl$_3$) δ 10.24 (s, 1H), 8.98 (d, J=2.33 Hz, 1H), 8.67 (d, J=1.78 Hz, 1H), 8.05 (t, J=2.06 Hz, 1H), 7.63 (s, 1H), 7.34 (d, J=8.37 Hz, 1H), 7.19 (dd, J=1.78, 8.37 Hz, 1H), 6.20 (s, 1H), 3.26-3.31 (m, 1H), 3.05-3.12 (m, 1H), 2.83-2.99 (m, 2H), 2.32-2.45 (m, 2H), 2.15 (q, J=8.78 Hz, 1H), 1.91-2.00 (m, 1H), 1.70-1.82 (m, 2H), 1.41-1.50 (m, 1H), 1.06 (d, J=6.0 Hz, 3H). $^{13}$C NMR (400 MHz, CDCl$_3$) δ 151.20, 148.90, 141.34, 138.23, 136.62, 135.69, 128.96, 126.24, 119.43, 118.31, 111.40, 109.59, 99.23, 60.46, 53.63, 53.36, 33.21, 26.38, 22.16, 19.60. [M+H]$^+$ at m/z 331.

Example 87

5-(5-Methoxy-pyridin-3-yl)-2-[2-(2-(R)-methyl-pyrrolidin-1-yl)-ethyl]-1H-indole

The title compound was prepared by the procedure described for 65D, except substituting 4-cyanophenylboronic acid with 3-methoxy-5-(4,4,5,5-tetramethyl-[1,3,2]dioxaborolan-2-yl)-pyridine. $^1$H NMR (400 MHz, CDCl$_3$) δ 10.09 (s, 1H), 8.43 (d, J=1.78, 1H), 8.14 (d, J=2.74 Hz, 1H), 7.64 (d, J=1.65 Hz, 1H), 7.29-7.34 (m, 2H), 7.22-7.24 (m, 1H), 6.18 (s, 1H), 3.83 (s, 3H), 3.24-3.29 (m, 1H), 3.04-3.09 (m, 1H), 2.82-2.98 (m, 2H), 2.29-2.43 (m, 2H), 2.14 (q, J=8.78 Hz, 1H), 1.83-1.96 (m, 1H), 1.68-1.83 (m, 2H), 1.40-1.49 (m, 1H), 1.05 (d, J=6.0 Hz, 3H). $^{13}$C NMR (400 MHz, CDCl$_3$) δ 155.25, 140.62, 138.66, 135.32, 134.46, 128.77, 128.61, 119.90, 118.89, 118.18, 110.91, 99.08, 60.45, 55.65, 53.66, 53.48, 33.18, 26.63, 22.14, 19.56. [M+H]$^+$ at m/z 336.

Example 88

5-(6-Fluoro-pyridin-3-yl)-2-[2-(2-(R)-methyl-pyrolidin-1-yl)-ethyl]-1H-indole

The title compound was prepared by the procedure described for 65D, except substituting 4-cyanophenylboronic acid with 2-fluoro-5-(4,4,5,5-tetramethyl-[1,3,2]dioxaborolan-2-yl)-pyridine. $^1$H NMR (400 MHz, CDCl$_3$) δ 10.07 (s, 1H), 8.35 (m, 1H), 7.88-7.92 (m, 1H), 7.58 (d, J=2.3 Hz, 1H), 7.30 (d, J=8.0 Hz, 1H), 7.11 (dd, J=1.78, 8.0 Hz, 1H), 6.86-6.89 (m, 1H), 6.18 (s, 1H), 3.25-3.30 (m, 1H), 3.04-3.11 (m, 1H), 2.82-2.98 (m, 2H), 2.29-2.43 (m, 2H), 2.15 (q, J=8.78 Hz, 1H), 1.85-1.99 (m, 1H), 1.69-1.85 (m, 2H), 1.40-1.50 (m, 1H), 1.06 (d, J=3.6 Hz, 3H). $^{13}$C NMR (400 MHz, CDCl$_3$) δ 163.15, 160.81, 145.29, 145.15, 140.86, 139.35, 139.15, 136.14, 135.18, 128.80, 119.69, 117.99, 111.00, 109.01, 108.65, 99.03, 60.45, 53.67, 53.47, 33.21, 26.49, 22.16, 19.60. [M+H]$^+$ at m/z 324.

Example 89

2-[2-(2-(R)-Methyl-pyrrolidin-1-yl)-ethyl]-5-pyrimidin-5-yl-1H-indole

The title compound was prepared by the procedure described for 65D, except substituting 4-cyanophenylboronic acid with 5-(4,4,5,5-tetramethyl-[1,3,2]dioxaborolan-2-yl)-pyrimidine. $^1$H NMR (400 MHz, CDCl$_3$) δ 10.29 (s, 1H), 9.12 (s, 1H), 8.97 (s, 2H), 7.72 (d, J=1.78 Hz, 1H), 7.42 (d, J=12.0 Hz, 1H), 7.29 (dd, J=1.85, 8.30 Hz, 1H), 6.29 (s, 1H), 3.34-3.38 (m, 1H), 3.14-3.19 (m, 1H), 2.92-3.08 (m, 2H), 2.39-2.53 (m, 2H), 2.25 (q, J=8.64 Hz, 1H), 2.01-2.08 (m, 1H), 1.78-1.93 (m, 2H), 1.49-1.59 (m, 1H), 1.14 (d, J=6.0 Hz, 3H). $^{13}$C NMR (400 MHz, CDCl$_3$) δ 155.86, 154.38, 141.08, 135.61, 135.50, 128.96, 125.02, 119.33, 118.07, 111.38, 99.19, 60.53, 53.63, 53.41, 33.18, 26.39, 22.16, 19.54. [M+H]$^+$ at m/z 307.

Example 90

1-Methyl-2-[2-(2-(R)-methyl-pyrrolidin-1-yl)-ethyl]-5-pyridin-3-yl-1H-indole

The title compound was prepared by the procedure described for Example 65G, except substituting 4-cyanophenylboronic acid with 3-pyridinylboronic acid. $^1$H NMR (400 MHz, CDCl$_3$) δ 8.79 (d, J=1.78 Hz, 1H), 8.42 (dd, J=1.58, 4.73 Hz, 1H), 7.78-7.81 (m, 1H), 7.63 (s, 1H), 7.21-7.27 (m, 3H), 6.26 (s, 1H), 3.61 (s, 3H), 3.18-3.23 (m, 1H), 3.08-3.11 (m, 1H), 2.84-2.96 (m, 2H), 2.29-2.40 (m, 2H), 2.15 (q, J=8.78 Hz, 1H), 1.85-1.92 (m, 1H), 1.64-1.83 (m, 2H), 1.36-1.43 (m, 1H), 1.06 (d, J=6.0 Hz, 3H). $^{13}$C NMR (400 MHz, CDCl$_3$) δ 147.95, 146.77, 140.03, 137.64, 136.76, 133.94, 128.76, 128.08, 119.80, 118.15, 109.13, 99.16, 60.13, 54.09, 53.20, 32.82, 29.82, 26.73, 21.2, 19.20. [M+H]$^+$ at m/z 320.

Example 91

1-Methyl-2-[2-(2-(R)-methyl-pyrrolidin-1-yl)-ethyl]-5-pyrimidin-5-yl-1H-indole

The title compound was prepared by the procedure described for Example 65G, except substituting 4-cyanophenylboronic acid with 5-(4,4,5,5-tetramethyl-[1,3,2]dioxaborolan-2-yl)-pyrimidine. $^1$H NMR (400 MHz, CDCl$_3$) δ 9.13 (s, 1H), 8.97 (s, 2H), 7.72 (m, 1H), 7.33-7.39 (m, 2H), 6.37 (s, 1H), 3.73 (s, 3H), 3.27-3.32 (m, 1H), 3.15-3.20 (m, 1H), 2.94-3.06 (m, 2H), 2.35-2.49 (m, 2H), 2.25 (q, J=8.78 Hz, 1H), 1.92-2.01 (m, 1H), 1.73-1.87 (m, 2H), 1.42-1.52 (m, 1H), 1.15 (d, J=6.20 Hz, 3H). $^{13}$C NMR (400 MHz, CDCl$_3$) δ 155.91, 154.33, 140.59, 137.14, 135.27, 128.30, 125.04, 119.33, 118.15, 109.55, 99.31, 60.13, 54.19, 53.20, 32.88, 29.91, 26.86, 21.97, 19.33 [M+H]$^+$ at m/z 321.

Example 92

5-{1-Methyl-2-[2-(2-(R)-methyl-pyrrolidin-1-yl)-ethyl]-1H-indol-5-yl}-nicotinonitrile The title compound was prepared by the procedure described for Example 65G, except substituting 4-cyanophenylboronic acid with 5-(4,4,5,5-tetramethyl-[1,3,2]dioxaborolan-2-yl)-nicotinonitrile. $^1$H NMR (400 MHz, CDCl$_3$) δ 9.05 (d, J=2.20 Hz, 1H), 8.74 (d, J=1.74 Hz, 1H), 8.12 (m, 1H), 7.71 (d, J=0.82 Hz, 1H), 7.25-7.38 (M, 2H), 6.37 (s, 1H), 3.73 (S, 3H), 3.25-3.32 (m, 1H), 3.15-3.22 (m, 1H), 2.97-3.05 (m, 2H), 2.39-2.50 (m, 2H), 2.25 (q, J=8.78 Hz, 1H), 1.93-2.02 (m, 1H), 1.74-1.87 (m, 2H), 1.40-1.52 (m, 1H), 1.16 (d, J=6.1 Hz, 3H). $^{13}$C NMR (400 MHz, CDCl$_3$) δ 151012, 148.93, 140.72, 137.99, 137.25, 136.55, 128.27, 126.24, 119.47, 118.40, 116.67, 109.59, 99.40, 60.17, 54.16, 53.14, 32.86, 29.94, 26.79, 21.96, 19.26. [M+H]$^+$ at m/z 345.

Example 93

4-{2-[2-(2-(R)-Methyl-pyrrolidin-1-yl)-ethyl]-1H-benzoimidazol-5-yl}-benzonitrile

Example 93A

3-(2-(R)-Methyl-pyrrolidin-1-yl)-propionic acid ethyl ester

In a round-bottom flask, 2-(R)-methylpyrrolidine HCl (5.5 g, 45 mmol) was dissolved in CH$_3$CN (20 mL). To the stirred solution was added milled K$_2$CO$_3$ (8.3 g, 60 mmol). The suspension was stirred at room temperature for approximately 1 h. Ethyl acrylate (3.25 mL, 30 mmol) and EtOH (40 mL) were then added. The reaction mixture was stirred until analysis by GC showed completion (the Area % of ethyl acrylate was less than 1% (approximately 2 h)). The reaction mixture was filtered and the wet cake (excess K$_2$CO$_3$) was washed with CH$_3$CN (5-10 mL). The filtered solution was then concentrated under reduced pressure to minimum volume (white slurry). Methyl t-butyl ether (MTBE) and H$_2$O were added, at which time all solids dissolved. The organic layer was washed a second time with water and then concentrated to yield 5.6 g of the title compound. The oil product was used in the next step without further purification.

Example 93B

4-Bromo-benzene-1,2-diamine

4-Bromo-2-nitroaniline (12 g, 55 mmol), 1% Pt/C (1.2 g) and THF (120 mL) were added to a 250 mL bottle. The reaction mixture was hydrogenated at a pressure of approximately 40 psig H$_2$. The hydrogenation reaction mixture was monitored by HPLC until the Area % of 4-bromo-2-nitroaniline was less than 1%. The reaction mixture was filtered and then concentrated to yield 10.6 g of 4-bromo-benzene-1,2-diamine (as a black oil that solidifies). 4-Bromo-benzene-1,2-diamine was used in the next step without further purification. $^1$H NMR (400 MHz, CDCl$_3$) δ 3.28 (br, 4H), 6.54 (d, 1H), 6.77-6.81 (m, 2H).

Example 93C

5-Bromo-2-[2-(2-(R)-methyl-pyrrolidin-1-yl)-ethyl]-1H-benzoimidazole

In a round-bottom flask was charged 3-(2-(R)-methyl-pyrrolidin-1-yl)-propionic acid ethyl ester (5.6 g, 30 mmol), 4-bromo-benzene-1,2-diamine (5.6 g, 30 mmol) and 56 mL of 5% P$_2$O$_5$ in CH$_3$SO$_3$H (Eaton's reagent). After briefly stirring, the homogeneous solution was heated to 110° C. for approximately 24-48 h. The reaction mixture was quenched with ice (~50 g) and then the pH slowly adjusted to pH>11 with 50% NaOH. The product was extracted with isopropyl acetate (100 mL). The organic layer was then extracted with 5% NaHCO$_3$, H$_2$O and then distilled to dryness. The crude product was purified by column chromatography to provide the title compound (3.7 g). $^1$H NMR (500 MHz, [(CD$_3$)$_2$SO] δ 1.00 (d, 3H), 1.27 (m, 1H), 1.63 (m, 2H), 1.85 (m, 1H), 2.11 (m, 1H), 2.31 (m, 1H), 2.45 (m, 1H), 2.91-2.99 (m, 2H), 3.09 (m, 1H), 3.19 (m, 1H), 7.24 (m, 1H), 7.43 (d, 1H), 7.66 (s, 1H), some protons were not readily identified due to exchange broadening. $^{13}$C NMR (500 MHz, [(CD$_3$)$_2$SO+2 drops DCl] δ 15.3, 21.0, 23.2, 31.0, 48.3, 52.3, 64.3, 115.9, 116.6, 117.9, 128.8, 130.2, 132.2, 151.1 (some $^{13}$C peaks were not readily identified due to exchange broadening at 25° C., but were observed under acidic conditions, 2 drops DCl). APPI-MS: (M+1)$^+$ at 308 m/z.

Example 93D

4-{2-[2-(2-(R)-Methyl-pyrrolidin-1-yl)-ethyl]-1H-benzoimidazol-5-yl}-benzonitrile Nitrogen (N$_2$) gas was bubbled through a solution of 5-bromo-2-[2-(2-methyl-pyrrolidin-1-yl)-ethyl]-1H-benzoimidazole (0.19 g, 0.6 mmol) and 4-cyanophenylboronic acid (0.13 g, 0.9 mmol) in 1,2-dimethoxyethane (4 mL) and H$_2$O (2 mL). To the mixture was added 2M Na$_2$CO$_3$ (1.2 mL, 2.4 mmol) and Pd(dppf)$_2$Cl$_2$:CH$_2$Cl$_2$ (1:1), and this mixture heated to 80° C. After approximately 24 h, the reaction mixture was cooled and extracted with ethyl acetate. The organic layer was then washed with H$_2$O and distilled to dryness. The crude product was purified by column chromatography to afford the title compound (0.08 g). $^1$H NMR (400 MHz, CDCl$_3$) δ 1.18 (d, 3H), 1.52-1.62 (m, 1H), 1.77-1.95 (m, 2H), 2.03-2.12 (m, 1H), 2.30 (q, 1H), 2.47-2.56 (m, 1H), 2.57-2.62 (m, 1H), 3.15-3.20 (m, 2H), 3.21-3.35 (m, 2H), 7.43 (dd, J=1.7 & 8.3, 1H), 7.62 (d, 1H), 7.68-7.73 (m, 4H), 7.76 (s, 1H); $^{13}$C NMR (400 MHz, CDCl$_3$) δ 19.5, 22.2, 27.4, 33.2, 51.5, 53.3, 60.5, 109.9, 118.9, 121.2, 127.5, 132.2, 133.0, 146.1, 156.1 (2 peaks overlapping and some $^{13}$C peaks were not readily identified due to exchange broadening). APPI-MS: (M+1)$^+$ at 331 m/z.

Example 94

2-[2-(2-(R)-Methyl-pyrrolidin-1-yl)-ethyl]-5-pyridin-3-yl-1H-benzoimidazole

The title compound was prepared according to the procedures described for Example 93D, except substituting 3-pyridinylboronic acid for 4-cyanophenylboronic acid. $^1$H NMR (400 MHz, [(CD$_3$)$_2$SO] δ 1.45(d, 3H), 1.63-173 (m, 1H), 1.94-2.05 (m, 2H), 2.18-2.26 (m, 1H), 3.21-3.32 (m, 5H), 3.47-3.83 (m, 5H), 4.02-4.13 (m, 1H), 7.92-7.98 (m, 2H), 8.04-8.07 (m, 1H), 8.23-8.27 (m, 1H), 8.83-8.87 (m, 2H), 9.30 (s, 1H). $^{13}$C NMR (400 MHz, [(CD$_3$)$_2$SO]δ15.1, 31.0, 23.4, 30.9, 112.6, 114.4, 124.3, 126.2, 131.0, 132.0, 137.2, 141.1, 141.3, 141.6, 151.1 (some $^{13}$C peaks were not readily identified due to exchange broadening). APPI-MS: (M+H)$^+$ at 307 m/z.

Example 95

5-(4-Fluoro-phenyl)-2-[2-(2-(R)-methyl-pyrrolidin-1-yl)-ethyl]-1H-benzoimidazole The title compound was prepared according to the procedures described for Example 93D, except substituting 4-fluororophenylboronic acid for 4-cyanophenylboronic acid. $^1$H NMR (400 MHz, CDCl$_3$) δ 1.18 (d, 3H), 1.52-1.62 (m, 1H), 1.76-1.93 (m, 2H), 2.01-2.11 (m, 1H), 2.28 (q, 1H), 2.46-2.53 (m, 1H), 2.54-2.62 (m, 1H), 3.11-3.18 (m, 2H), 3.22-3.35 (m, 2H), 7.07-7.13 (m, 2H), 7.38 (dd, J=1.7 & 8.3, 1H), 7.54-7.59 (m, 3H), 7.68 (s, 1H); $^{13}$C NMR (400 MHz, CDCl$_3$) δ 19.5, 22.2, 27.4, 33.2, 51.6, 53.4, 60.5, 115.1, 115.3, 121.3, 128.5, 128.6, 134.3, 137.8, 137.8, 155.4, 1604.4, 162.8 (some $^{13}$C peaks were not readily identified due to exchange broadening). APCI-MS: (M+1)$^+$ at 324 m/z.

Example 96

1-(4-{2-[2-(2-(R)-Methyl-pyrrolidin-1-yl)-ethyl]-1H-benzoimidazol-5-yl}-phenyl)-ethanone The title compound was prepared according to the procedures described for Example 93D, except substituting 4-acetylphenylboronic acid for 4-cyanophenylboronic acid. $^1$H NMR (400 MHz, [(CD$_3$)$_2$SO]) δ 1.03 (d, 3H), 1.26-1.34 (m, 1H), 1.61-1.64 (m, 2H), 1.83-1.91 (m, 1H), 2.16 (q, 1H), 2.31-2.39 (m, 1H), 2.61 (s, 3H), 2.92-3.07 (m, 2H), 3.11-3.16 (m, 1H), 3.21-3.28 (m, 1H), 7.49-7.58 (m, 2H), 7.81-7.84 (m, 3H), 8.00-8.03 (m, 2H) (some peaks overlapping with DMSO peaks); $^{13}$C NMR (400 MHz, CDCl$_3$) δ 19.5, 22.2, 26.9, 27.4, 33.1, 51.6, 53.3, 60.5, 121.4, 127.0, 128.6, 133.7, 134.9, 146.3, 155.8, 197.2 (2 peaks overlapping and some $^{13}$C peaks were not readily identified due to exchange broadening). ESI-MS: (M+1)$^+$ at 348 m/z.

Example 97

3-{2-[2-(2-(R)-Methyl-pyrrolidin-1-yl)-ethyl]-1H-benzoimidazol-5-yl}-benzonitrile The title compound was prepared according to the procedures described for Example 93D, except substituting 3-cyanophenylboronic acid for 4-cyanophenylboronic acid. $^1$H NMR (400 MHz, CDCl$_3$) δ 1.19 (d, 3H), 1.53-1.62 (m, 1H), 1.77-1.95 (m, 2H), 2.03-2.12 (m, 1H), 2.30 (q, 1H), 2.47-2.56 (m, 1H), 2.57-2.62 (m, 1H), 3.15-3.22 (m, 2H), 3.25-3.35 (m, 2H), 7.40 (dd, J=1.7 & 8.3, 1H), 7.51 (t, 1H), 7.58 (dt, J=1.45 & 7.7, 1H), 7.62 (d, 1H), 7.72 (dt, J=1.4 & 7.8, 1H), 7.83-7.86 (t, 1H), 7.89 (m, 1H); $^{13}$C NMR (400 MHz, CDCl$_3$) δ 19.4, 22.1, 27.3, 33.1, 51.6, 53.3, 60.6, 112.5, 118.7, 121.1, 129.2, 129.7, 130.5, 131.4, 132.7, 142.9, 155.9 (some $^{13}$C peaks were not readily identified due to exchange broadening). ESI-MS: (M+1)$^+$ at 331 m/z.

Example 98

1-(3-{2-[2-(2-(R)-Methyl-pyrrolidin-1-yl)-ethyl]-1H-benzoimidazol-5-yl}-phenyl)-ethanone The title compound was prepared according to the procedures described for Example 93D, except substituting 3-acetylphenylboronic acid for 4-cyanophenylboronic acid. $^1$H NMR (400 MHz, CDCl$_3$) δ 1.18 (d, 3H), 1.53-1.62 (m, 1H), 1.77-1.95 (m, 2H), 2.03-2.12 (m, 1H), 2.29 (q, 1H), 2.46-2.53 (m, 1H), 2.55-2.63 (m, 1H), 2.66 (s, 3H), 3.14-3.19 (m, 2H), 3.24-3.35 (m, 2H), 7.47 (dd, J=1.8 & 8.4, 1H), 7.52 (t, 1H), 7.62 (d, 1H), 7.77 (s, 1H), 7.83 (dq, J=1.0 & 7.7, 1H), 7.90 (dq, J=1.0 & 7.7, 1H), 8.22 (t, 1H); $^{13}$C NMR (400 MHz, CDCl$_3$) δ 19.5, 22.2, 27.0, 27.4, 33.2, 51.6, 53.3, 60.5, 121.3, 126.3, 126.8, 128.6, 131.7, 134.1, 137.2, 142.1, 155.7, 197.6 (some $^{13}$C peaks were not readily identified due to exchange broadening). ESI-MS: (M+1)$^+$ at 348 m/z.

Example 99

5-(3-Methoxy-phenyl)-2-[2-(2-(R)-methyl-pyrrolidin-1-yl)-ethyl]-1H-benzoimidazole The title compound was prepared according to the procedures described for Example 93D, except substituting 3-methoxyphenylboronic acid for 4-cyanophenylboronic acid. $^1$H NMR (400 MHz, CDCl$_3$ δ 1.18 (d, 3H), 1.52-1.61 (m, 1H), 1.76-1.95 (m, 2H), 2.02-2.10 (m, 1H), 2.28 (q, 1H), 2.46-2.55 (m, 1H), 2.56-2.62 (m, 1H), 3.14-3.20 (m, 2H), 3.23-3.35 (m, 2H), 3.86 (s, 3H), 6.86 (dq, J=1.3 & 8.2, 1H), 7.16 (t, 1H), 7.22 (dq, J=1.0 & 7.7, 1H), 7.84 (t, 1H), 7.44 (dd, J=1.7 & 8.3, 1H), 7.58 (d, 1H), 7.73 (s, 1H); $^{13}$C NMR (400 MHz, CDCl$_3$) δ 19.5, 22.2, 27.4, 33.2, 51.6, 53.4, 55.4, 60.6, 111.9, 112.9, 119.7, 121.4, 129.3, 135.1, 143.2, 155.3, 159.4 (some $^{13}$C peaks were not readily identified due to exchange broadening). ESI-MS: (M+1)$^+$ at 336 m/z.

Example 100

5-Furan-2-yl-2-[2-(2-(R)-methyl-pyrrolidin-1-yl)-ethyl]-1H-benzoimidazole

The title compound was prepared according to the procedures described for Example 93D, except substituting 2-furanboronic acid for 4-cyanophenylboronic acid.
$^1$H NMR (400 MHz, CDCl$_3$) δ 1.18 (d, 3H), 1.51-1.61 (m, 1H), 1.76-1.94 (m, 2H), 2.02-2.10 (m, 1H), 2.28 (q, 1H), 2.46-2.54 (m, 1H), 2.55-2.62 (m, 1H), 3.12-3.17 (m, 2H), 3.23-3.34 (m, 2H), 6.46 (q, 1H), 6.60 (dd, J=0.8 & 3.4, 1H), 7.44 (dd, J=0.8 & 1.9, 1H), 7.54 (d, 2H), 7.83 (s, 1H); $^{13}$C NMR (400 MHz, CDCl$_3$) δ 19.4, 22.1, 27.3, 33.1, 51.6, 53.3, 60.6, 103.7, 111.4, 118.4, 125.1, 141.0, 154.4, 155.4 (some $^{13}$C peaks were not readily identified due to exchange broadening). ESI-MS: (M+1)$^+$ at 296 m/z.

Example 101

5-(2,6-Difluoro-pyridin-3-yl)-2-[2-(2-(R)-methyl-pyrrolidin-1-yl)-ethyl]-1H-benzoimidazole The title compound was prepared according to the procedures described for Example 93D, except substituting (2,6-difluoro-3-pyridinyl)boronic acid for 4-cyanophenylboronic acid. $^1$H NMR (400 MHz, CDCl$_3$) δ 1.18 (d, 3H), 1.53-1.62 (m, 1H), 1.77-1.96 (m, 2H), 2.03-2.12 (m, 1H), 2.30 (q, 1H), 2.46-2.57 (m, 1H), 2.58-2.63 (m, 1H), 3.15-3.20 (m, 2H), 3.24-3.35 (m, 2H), 6.90 (dd, J=2.9 & 8.1, 1H), 7.84 (dt, J=1.7 & 8.4, 1H), 7.61 (d, 1H), 7.69 (s, 1H), 7.99 (dt, J=7.8 & 9.6, 1H); $^{13}$C NMR (400 MHz, CDCl$_3$) δ 19.4, 22.1, 27.3, 33.1, 51.6, 53.3, 60.6, 106.0-106.4 (dd), 121.1-121.2 (dd), 122.5, 144.8, 155.9, 160.7, 160.8 (some $^{13}$C peaks were not readily identified due to exchange broadening). ESI-MS: (M+1)$^+$ at 343 m/z.

Example 102

5-(6-Methoxy-pyridin-3-yl)-2-[2-(2-(R)-methyl-pyrrolidin-1-yl)-ethyl]-1H-benzoimidazole The title compound was prepared according to the procedures described for Example 93D, except (6-methoxy-3-pyridinyl)boronic acid for 4-cyanophenylboronic acid. $^1$H NMR (400 MHz, CDCl$_3$) δ 1.18 (d, 3H), 1.52-1.61 (m, 1H), 1.77-1.95 (m, 2H), 2.02-2.10 (m, 1H), 2.29 (q, 1H), 2.46-2.55 (m, 1H), 2.57-2.62 (m, 1H), 3.14-3.20 (m, 2H), 3.23-3.34 (m, 2H), 3.98 (s, 3H), 6.81 (dd, J=0.7 & 8.6, 1H), 7.36 (dd, J=1.7 & 8.3, 1H), 7.59 (d, 1H), 7.66 (d, 1H), 7.81 (dd, J=2.6 & 8.6, 1H), 8.40 (dd, J=0.7 & 2.5, 1H); $^{13}$C NMR (400 MHz, CDCl$_3$) δ 19.4, 22.1, 27.4, 33.1, 51.6, 53.4, 53.6, 60.6, 110.4, 120.9, 130.7, 131.8, 137.4, 144.6, 155.4, 162.7 (some $^{13}$C peaks were not readily identified due to exchange broadening). ESI-MS: (M+1)$^+$ at 337 m/z.

Example 103

5-(4-Methanesulfonyl-phenyl)-2-[2-(2-(R)-methyl-pyrrolidin-1-yl)-ethyl]-1H-benzoimidazole The title compound was prepared according to the procedures described for Example 93D, except substituting 4-methanesulfonylphenylboronic acid for 4-cyanophenylboronic acid. $^1$H NMR (400 MHz, CDCl$_3$) δ 1.18 (d, 3H), 1.52-1.62 (m, 1H), 1.79-1.95 (m, 2H), 2.03-2.12 (m, 1H), 2.30 (q, 1H), 2.47-2.56 (m, 1H), 2.57-2.62 (m, 1H), 3.09 (s, 3H), 3.15-3.21 (m, 2H), 3.24-3.35 (m, 2H), 7.46 (dd, J=1.8 & 8.4, 1H), 7.62 (d, 1H), 7.78 (s, 1H), 7.80 (dt, J=1.9 & 8.6, 2H), 7.97 (dt, J=2.0 & 8.6, 2H); $^{13}$C NMR (400 MHz, CDCl$_3$) δ 19.5, 22.2, 27.4, 33.2, 44.8, 51.5, 53.3, 60.5, 121.4, 127.5, 127.7, 132.9, 137.9, 147.2, 156.1 (2 peaks overlapping and some $^{13}$C peaks were not readily identified due to exchange broadening). ESI-MS: (M+1)$^+$ at 384 m/z.

Example 104

5-(2,4-Dimethoxy-pyrimidin-5-yl)-2-[2-(2-(R)-methyl-pyrrolidin-1-yl)-ethyl]-1H-benzoimidazole The title compound was prepared according to the procedures described for Example 93D, except substituting 2,4-dimethoxy-5-pyrimidinylboronic acid for 4-cyanophenylboronic acid. $^1$H NMR (400 MHz, CDCl$_3$) δ 1.18 (d, 3H), 1.52-1.61 (m, 1H), 1.77-1.97 (m, 2H), 2.00-2.11 (m, 1H), 2.29 (q, 1H), 2.47-2.55 (m, 1H), 2.57-2.63 (m, 1H), 3.14-3.20 (m, 2H), 3.22-3.35 (m, 2H), 4.02 (s, 3H), 4.04 (s, 3H), 7.30 (dd, J=1.6 & 8.2, 1H), 7.57 (d, 1H), 7.66 (s, 1H), 8.28 (s, 1H); $^{13}$C NMR (400 MHz, CDCl$_3$) δ 19.5, 22.2, 27.4, 33.1, 51.6, 53.4, 54.2, 54.9, 60.6, 116.8, 122.8, 126.6, 155.4, 157.1, 163.7, 167.7 (some $^{13}$C peaks were not readily identified due to exchange broadening). DCl-MS: (M+1)$^+$ at 368 m/z.

Example 105

5-Benzo[1,3]-dioxol-5-yl-2-[2-(2-(R)-methyl-pyrrolidin-1-yl)-ethyl]-1H-benzoimidazole The title compound was prepared according to the procedures described for Example 93D, except substituting 3,4-(methylenedioxy)phenylboronic acid for 4-cyanophenylboronic acid. $^1$H NMR (400 MHz, CDCl$_3$) δ 1.17 (d, 3H), 1.51-1.60 (m, 1H), 1.76-1.94 (m, 2H), 1.99-2.10 (m, 1H), 2.28 (q, 1H), 2.45-2.54 (m, 1H), 2.55-2.62 (m, 1H), 3.12-3.18 (m, 2H), 3.22-3.34 (m, 2H), 5.98 (s, 2H), 6.87 (d, 1H), 7.06-7.10 (m, 2H), 7.36 (dd, J=1.5 & 8.3, 1H), 7.55 (d, 1H), 7.65 (s, 1H); $^{13}$C NMR (400 MHz, CDCl$_3$) δ 19.5, 22.1, 27.4, 33.1, 51.6, 53.3, 60.5, 100.9, 107.8, 108.3 120.5, 121.2, 135.1, 136.1, 146.2, 147.6, 155.2 (some $^{13}$C peaks were not readily identified due to exchange broadening). DCl-MS: (M+1)$^+$ at 350 m/z.

Example 106

5-(5-Methoxy-pyridin-3-yl)-2-[2-(2-(R)-methyl-pyrrolidin-1-yl)-ethyl]-1H-benzoimidazole The title compound was prepared according to the procedures described for Example 93D, except substituting 3-methoxy-5-(4,4,5,5-tetramethyl-[1,3,2]dioxaborolan-2-yl)-pyridine for 4-cyanophenylboronic acid. $^1$H NMR (400 MHz, CDCl$_3$) δ 1.18 (d, 3H), 1.53-1.62 (m, 1H), 1.78-1.96 (m, 2H), 2.03-2.11 (m, 1H), 2.30 (q, 1H), 2.48-2.56 (m, 1H), 2.58-2.63 (m, 1H), 3.15-3.21 (m, 2H), 3.24-3.35 (m, 2H), 3.92 (s, 3H), 7.41-7.43 (m, 2H), 7.62 (d, 1H), 7.74 (s, 1H), 8.25 (d, 1H), 8.49 (d, 1H); $^{13}$C NMR (400 MHz, CDCl$_3$) δ 19.5, 22.2, 27.4, 33.1, 51.6, 53.4, 55.7, 60.6, 119.1, 121.3, 131.4, 135.0, 137.9, 140.5, 155.3, 155.8 (some $^{13}$C peaks were not readily identified due to exchange broadening). DCl-MS: (M+1)$^+$ at 337 m/z.

Example 107

5-(2,6-Dimethyl-pyridin-3-yl)-2-[2-(2-(R)-methyl-pyrrolidin-1-yl)-ethyl]-1H-benzoimidazole The title compound was prepared according to the procedures described for Example 93D, except substituting 2,6-dimethyl-3-(4,4,5,5-tetremethyl-[1,3,2]dioxaborolan-2-yl)-pyridine for 4-cyanophenylboronic acid. $^1$H NMR (400 MHz, CDCl$_3$) δ 1.18 (d, 3H), 1.51-1.60 (m, 1H), 1.77-1.94 (m, 2H), 2.02-2.10 (m, 1H), 2.29 (q, 1H), 2.46-2.54 (m, 4H), 2.56-2.63 (m, 4H), 3.13-3.21 (m, 2H), 3.24-3.35 (m, 2H), 3.92 (s, 3H), 7.03 (d, 1H), 7.12 (dd, J=1.7 & 8.2, 1H), 7.44-7.46 (m, 2H), 7.56 (d, 1H); $^{13}$C NMR (400 MHz, CDCl$_3$) δ 19.5, 22.1, 23.7, 24.4, 27.4, 33.1, 51.6, 53.3, 60.6, 120.2, 121.3, 133.7, 134.3, 137.6, 154.7, 155.3, 155.6 (some $^{13}$C peaks were not readily identified due to exchange broadening). DCl-MS: (M+1)$^+$ at 335 m/z.

Example 108

4-{2-[2-(2-Methyl-pyrrolidin-1-yl)-ethyl]-1H-benzoimidazol-5-yl}-benzoic acid methyl ester The title compound was prepared according to the procedures described for Example 93D, except substituting 4-methoxycarbonylphenylboronic acid for 4-cyanophenylboronic acid. $^1$H NMR (400 MHz, CDCl$_3$) δ 1.18 (d, 3H), 1.53-1.62 (m, 1H), 1.78-1.94 (m, 2H), 2.03-2.12 (m, 1H), 2.29 (q, 1H), 2.47-2.56 (m, 1H), 2.57-2.62 (m, 1H), 3.15-3.21 (m, 2H), 3.24-3.35 (m, 2H), 3.93 (s, 3H), 7.48 (dd, J=1.7 & 8.3, 1H), 7.61 (d, 1H), 7.69 (dt, J=1.9 & 8.6, 2H), 7.78 (d, 1H), 8.08 (dt, J=1.9 & 8.6, 2H); $^{13}$C NMR (400 MHz, CDCl$_3$) δ 19.5, 22.2, 27.4, 33.2, 51.6, 52.2, 53.3, 60.6, 121.4, 126.9, 127.9, 129.7, 133.9, 146.1, 155.7, 166.6 (2 peaks overlapping and some $^{13}$C peaks were not readily identified due to exchange broadening). DCl-MS: (M+1)$^+$ at 364 m/z.

Example 109

2-[2-(2-(R)-Methyl-pyrrolidin-1-yl)-ethyl]-5-(4-methylsulfanyl-phenyl)-1H-benzoimidazole The title compound was prepared according to the procedures described for Example 93D, except substituting 4-methylsulfanylphenylboronic acid for 4-cyanophenylboronic acid. $^1$H NMR (400 MHz, CDCl$_3$) δ 1.18 (d, 3H), 1.52-1.61 (m, 1H), 1.76-1.93 (m, 2H), 2.02-2.10 (m, 1H), 2.29 (q, 1H), 2.46-2.55 (m, 4H), 2.57-2.62 (m, 1H), 3.14-3.20 (m, 2H), 3.23-3.34 (m, 2H), 7.32 (dt, J=2.2 & 8.5, 2H), 7.42 (dd, J=1.7 & 8.4, 1H), 7.52-7.59 (m, 3H), 7.70 (d, 1H); $^{13}$C NMR (400 MHz, CDCl$_3$) δ 16.4, 19.4, 22.1, 27.4, 33.1, 51.6, 53.4, 60.6, 121.1, 126.8, 127.4, 134.6, 136.3, 138.6, 155.2 (2 peaks overlapping and some $^{13}$C peaks were not readily identified due to exchange broadening). DCl-MS: (M+1)$^+$ at 352 m/z.

Example 110

5-(3,5-Difluoro-phenyl)-2-[2-(2-(R)-methyl-pyrrolidin-1-yl)-ethyl]-1H-benzoimidazole The title compound was prepared according to the procedures described for Example 93D, except substituting 3,5-difluorophenylboronic acid for 4-cyanophenylboronic acid. $^1$H NMR (400 MHz, CDCl$_3$) δ 1.18 (d, 3H), 1.52-1.62 (m, 1H), 1.77-1.95 (m, 2H), 2.03-2.12 (m, 1H), 2.29 (q, 1H), 2.47-2.55 (m, 1H), 2.56-2.63 (m, 1H), 3.14-3.20 (m, 2H), 3.23-3.35 (m, 2H), 6.74 (tt, J=2.3 & 8.9, 1H), 7.10-7.16 (m, 2H), 7.39 (dd, J=1.8 & 8.4, 1H), 7.59 (d, 1H), 7.70 (d, 1H); $^{13}$C NMR (400 MHz, CDCl$_3$) δ 19.5, 22.2, 27.3, 33.2, 51.6, 53.3, 60.6, 101.6 (t), 109.7 (d), 109.9 (d), 121.1, 132.8, 145.0 (t), 155.9, 161.4 (d), 163.9 (d) (some $^{13}$C peaks were not readily identified due to exchange broadening). DCl-MS: (M+1)$^+$ at 342 m/z.

Example 111

2-[2-(2-(R)-Methyl-pyrrolidin-1-yl)-ethyl]-5-pyrimidin-5-yl-1H-benzoimidazole

The title compound was prepared according to the procedures described for Example 93D, except substituting 5-(4,4,5,5-tetramethyl-[1,3,2]dioxaborolan-2-yl)-pyrimidine for 4-cyanophenylboronic acid. $^1$H NMR (400 MHz, CDCl$_3$) δ 1.21 (d, 3H), 1.55-1.64 (m, 1H), 1.80-1.98 (m, 2H), 2.05-2.14 (m, 1H), 2.34 (q, 1H), 2.52-2.61 (m, 1H), 2.62-2.67 (m, 1H), 3.15-3.24 (m, 2H), 3.27-3.37 (m, 2H), 7.41 (dd, J=1.7 & 8.3, 1H), 7.66 (d, 1H), 7.76 (d, 1H), 8.99 (s, 2H), 9.16 (s, 1H); $^{13}$C NMR (400 MHz, CDCl$_3$) δ 19.3, 22.2, 27.3, 33.1, 51.6, 53.3, 60.8, 120.8, 127.8, 134.8, 154.5, 156.1, 156.4 (1 peak overlapping and some $^{13}$C peaks were not readily identified due to exchange broadening). DCl-MS: (M+1)$^+$ at 308 m/z.

Example 112

8-{2-[2-(2-(R)-Methyl-pyrrolidin-1-yl)-ethyl]-1H-benzoimidazol-5-yl}-quinoline

The title compound was prepared according to the procedures described for Example 93D, except substituting 8-quinolinylboronic acid for 4-cyanophenylboronic acid. $^1$H NMR (400 MHz, CDCl$_3$) δ 1.15 (d, 3H), 1.47-1.57 (m, 1H), 1.73-1.91 (m, 2H), 1.98-2.08 (m, 1H), 2.27 (q, 1H), 2.45-2.53 (m, 1H), 2.54-2.60 (m, 1H), 3.06-3.18 (m, 2H), 3.21-3.32 (m, 2H), 7.39 (dd, J=4.1 & 8.2, 1H), 7.50 (dd, J=1.6 & 8.2, 1H), 7.60 (dd, J=7.2 & 8.0, 1H), 7.65 (d, 1H), 7.77 (dd, J=1.4 & 7.2, 1H), 7.80 (dd, J=1.5 & 8.1, 1H), 7.84 (d, 1H), 8.20 (dd, J=1.8 & 8.3, 1H), 8.91 (dd, J=1.8 & 4.2, 1H); $^{13}$C NMR (400 MHz, CDCl$_3$) δ 19.3, 22.1, 27.5, 33.1, 51.7, 53.4, 60.6, 120.6, 124.5, 126.0, 126.8, 128.5, 130.4, 133.1, 136.0, 141.2, 145.8, 149.6, 154.7 (some $^{13}$C peaks were not readily identified due to exchange broadening). DCl-MS: (M+1)$^+$ at 357 m/z.

Example 113

Dimethyl-(4-{2-[2-(2-(R)-methyl-pyrrolidin-1-yl)-ethyl]-1H-benzoimidazol-5-yl}-phenyl)-amine The title compound was prepared according to the procedures described for Example 93D, except substituting 4-(dimethylamino)-phenylboronic acid for 4-cyanophenylboronic acid. $^1$H NMR (400 MHz, CDCl$_3$) δ 1.17 (d, 3H), 1.50-1.60 (m, 1H), 1.75-1.94 (m, 2H), 1.98-2.09 (m, 1H), 2.27 (q, 1H), 2.44-2.52 (m, 1H), 2.54-2.59 (m, 1H), 2.98 (s, 6H), 3.12-3.19 (m, 2H), 3.22-3.33 (m, 2H), 6.80 (dt, J=2.6 & 8.8, 2H), 7.41 (dd, J=1.7 & 8.3, 1H), 7.51-7.56 (m, 3H), 7.67 (d, 1H); $^{13}$C NMR (400 MHz, CDCl$_3$) δ 19.5, 22.1, 27.5, 33.2, 40.9, 51.7, 53.4, 60.5, 112.7, 120.9, 127.6, 130.0, 135.4, 149.2, 154.8 (3 peaks overlapping and some $^{13}$C peaks were not readily identified due to exchange broadening). DCl-MS: (M+1)$^+$ at 349 m/z.

Example 114

5-(6-Fluoro-pyridin-3-yl)-2-[2-(2-(R)-methyl-pyrrolidin-1-yl)-ethyl]-1H-benzoimidazole The title compound was prepared according to the procedures described for Example 93D, except substituting 2-fluoro-5-(4,4,5,5-tetramethyl-[1,3,2]dioxaborolan-2-yl)-pyridine for 4-cyanophenylboronic acid. $^1$H NMR (400 MHz, CDCl$_3$) δ 1.18 (d, 3H), 1.53-1.62 (m, 1H), 1.78-1.96 (m, 2H), 2.03-2.12 (m, 1H), 2.30 (q, 1H), 2.48-2.56 (m, 1H), 2.57-2.63 (m, 1H), 2.98 (s, 6H), 3.11-3.21 (m, 2H), 3.24-3.35 (m, 2H), 6.99 (ddd, J=0.6 & 8.5 & 3.0, 1H), 7.86 (dd, J=1.7 & 8.3, 1H), 7.62 (d, 1H), 7.69 (d, 1H), 7.99 (ddd, J=2.6 & 7.7 & 8.4, 1H), 8.43-8.44 (m, 1H); $^{13}$C NMR (400 MHz, CDCl$_3$) δ 19.5, 22.2, 27.3, 33.2, 51.6, 53.3, 60.6, 109.1 (d), 121.1, 130.5, 135.3 (d), 139.5 (d), 145.4 (d), 155.9, 162.2 (d) (some $^{13}$C peaks were not readily identified due to exchange broadening). DCl-MS: (M+1)$^+$ at 325 m/z.

Example 115

Determination of Biological Activity

To determine the effectiveness of representative compounds of this invention as histamine-3 receptor ligands (H$_3$ receptor ligands), the following tests were conducted according to methods previously described (European Journal of Pharmacology, 188:219-227 (1990); Journal of Pharmacology and Experimental Therapeutics, 275:598-604 (1995); Journal of Pharmacology and Experimental Therapeutics, 276:1009-1015 (1996); and Biochemical Pharmacology, 22:3099-3108 (1973)).

Briefly, male Sprague-Dawley rat brain cortices were homogenized (1 g tissue/10 mL buffer) in 50 mM Tris-HCl/5 mM EDTA containing protease inhibitor cocktail (Calbiochem) using a polytron set at 20,500 rpm. Homogenates were centrifuged for 20 minutes at 40,000×g. The supernatant was decanted, and pellets were weighed. The pellet was resuspended by polytron homogenization in 40 mL 50 mM Tris-HCl/5 mM EDTA with protease inhibitors and centrifuged for 20 minutes at 40,000×g. The membrane pellet was resuspended in 6.25 volumes (per gram wet weight of pellet) of 50 mM Tris-HCl/5 mM EDTA with protease inhibitors and aliquots flash frozen in liquid $N_2$ and stored at −70° C. until used in assays. Rat cortical membranes (12 mg wet weight/tube) were incubated with (3H)—N-α-methylhistamine (~0.6 nM) with or without $H_3$ receptor antagonists in a total incubation volume of 0.5 mL of 50 mM Tris-HCl/5 mM EDTA (pH 7.7). Test compounds were dissolved in DMSO to provide a 20 mM solution, serially diluted and then added to the incubation mixtures prior to initiating the incubation assay by addition of the membranes. Thioperamide (3 μM) was used to determine nonspecific binding. Binding incubations were conducted for 30 minutes at 25° C. and terminated by addition of 2 mL of ice cold 50 mM Tris-HCl (pH 7.7) and filtration through 0.3% polyethylenimine-soaked Unifilter plates (Packard). These filters were washed 4 additional times with 2 mL of ice-cold 50 mM Tris-HCl and dried for 1 hour. Radioactivity was determined using liquid scintillation counting techniques. Results were analyzed by Hill transformation and $K_i$, values were determined using the Cheng-Prusoff equation.

Representative compounds of the invention bound to histamine-3 receptors with binding affinities from about 810 nM to about 0.12 nM. Preferred compounds of the invention bound to histamine-3 receptors with binding affinities from about 100 nM to about 0.12 nM. More preferred compounds of the invention bound to histamine-3 receptors with binding affinities from about 20 nM to about 0.12 nM.

Compounds of the invention are histamine-3 receptor ligands that modulate function of the histamine-3 receptor by altering the activity of the receptor. These compounds may be inverse agonists that inhibit the basal activity of the receptor or they may be antagonists that completely block the action of receptor-activating agonists. These compounds may also be partial agonists that partially block or partially activate the histamine-3 receptor or they may be agonists that activate the receptor.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. All references cited herein are incorporated by reference. In the case of inconsistencies, the instant disclosure, including definitions, will prevail.

What is claimed is:
1. A compound of the formula:

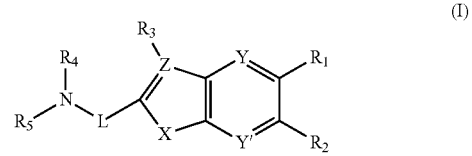

(I)

or a pharmaceutically acceptable salt, ester, or amide thereof, wherein:
X is NH or N(alkyl);
Y and Y' are each independently CH or CF;
Z is C;
one of $R_1$ and $R_2$ is selected from the group consisting of aryl substituted with 0, 1, 2, 3, 4, or 5 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, formyl, haloalkoxy, haloalkyl, halo, hydroxy, hydroxyalkyl, mercapto, nitro, thioalkoxy, dialkylamino, and dialkylaminosulfonyl, heteroaryl substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, formyl, haloalkoxy, haloalkyl, halo, hydroxy, hydroxyalkyl, mercapto, nitro, thioalkoxy, dialkylamino, and dialkylaminosulfonyl, and heterocycle substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, arylalkyl, arylalkoxycarbonyl, carboxy, cyano, formyl, haloalkoxy, haloalkyl, halo, hydroxy, hydroxyalkyl, mercapto, nitro, oxo, thioalkoxy, dialkylamino, and dialkylaminosulfonyl;
the other of $R_1$ and $R_2$ is selected from the group consisting of hydrogen, alkyl, alkoxy, aryl, cycloalkyl, halo, cyano, and thioalkoxy;
$R_3$ is selected from the group consisting of hydrogen, methyl, alkoxy, halo, and cyano;
$R_4$ and $R_5$ are each independently selected from the group consisting of alkyl, haloalkyl, hydroxyalkyl, alkoxyalkyl, cycloalkyl, and cycloalkylalkyl, or
$R_4$ and $R_5$ taken together with the nitrogen atom to which each is attached form a non-aromatic ring of the structure (a):

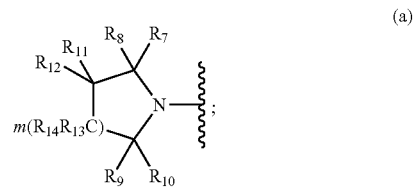

(a)

$R_7$, $R_8$, $R_9$, and $R_{10}$ are each independently selected from the group consisting of hydrogen, halo, hydroxyalkyl, fluoroalkyl, and alkyl; or one of the pair $R_7$ and $R_8$ or the pair $R_9$ and $R_{10}$ is taken together to form a $C_3$-$C_6$ ring, wherein 0, 1, or 2 heteroatoms selected from O, N, or S replace a carbon atom in the ring;

$R_{11}$ and $R_{12}$ are each independently selected from the group consisting of hydrogen, hydroxy, hydroxyalkyl, alkyl, and fluoro;

$R_{13}$ and $R_{14}$ at each occurrence are independently selected from the group consisting of hydrogen, alkyl, and fluoro;

L is —$[C(R_{15})(R_{16})]_n$—;

$R_{15}$ and $R_{16}$ at each occurrence are independently selected from the group consisting of hydrogen, alkyl, alkoxy, and fluoro;

m is 0, 1, 2 or 3; and n is 2 or 3.

2. The compound of claim 1, wherein $R_1$ is heteroaryl substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, formyl, haloalkoxy, haloalkyl, halo, hydroxy, hydroxyalkyl, mercapto, nitro, thioalkoxy, dialkylamino, and dialkylaminosulfonyl.

3. The compound of claim 1, wherein $R_1$ and $R_2$ are each independently selected from the group consisting of furyl, imidazolyl, isoxazolyl, isothiazolyl, oxadiazolyl, oxazolyl, nicotinyl, phenyl, pyrazinyl, pyrazolyl, pyridazinyl, pyridazinonyl, pyridinyl, pyrimidinyl, pyrrolyl, tetrazolyl, thiadiazolyl, thiazolyl, thienyl, triazinyl, triazolyl, azepanyl, azetidinyl, aziridinyl, azocanyl, morpholinyl, piperazinyl, piperidinyl, pyrrolidinyl, pyrrolinyl, thiomorpholinyl, tetrahydrofuryl, tetrahydropyranyl, benzothienyl, isoquinolyl, indolyl, indolizin-2-yl, indazolyl, imidazo[1,2-a]pyridin-2-yl, pyrazolo[1,5-a]pyridin-2-yl, 3-oxo-2H-pyridazin-2-yl, quinolyl, and 2-oxo-1H-pyridin-1-yl.

4. The compound of claim 1, wherein L is selected from the group consisting of —$CH_2CH_2$— or —$CH_2CH_2CH_2$—.

5. The compound of claim 1, wherein $R_3$ is hydrogen or methyl.

6. The compound of claim 1, wherein $R_4$ and $R_5$ taken together with the nitrogen atom to which each is attached form a 4- to 7-membered non-aromatic ring represented by formula (a).

7. The compound of claim 6, wherein the 4- to 7-membered non-aromatic ring is selected from the group consisting of azepanyl, pyrrolidinyl, and piperidinyl.

8. The compound of claim 1, wherein at least one substituent represented by $R_7$, $R_8$, $R_9$, and $R_{10}$ is selected from the group consisting of alkyl, halo, fluoroalkyl, and hydroxyalkyl.

9. The compound of claim 6, wherein the 4- to 7-membered non-aromatic ring is selected from the group consisting of methylpyrrolidinyl, ethylpyrrolidinyl, dimethylaminopyrrolidinyl, isopropylpyrrolidinyl, isobutylpyrrolidinyl, hydroxymethylpyrrolidinyl, and fluoromethylpyrrolidinyl.

10. The compound of claim 1, wherein:

$R_1$ is heteroaryl substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, formyl, haloalkoxy, haloalkyl, halo, hydroxy, hydroxyalkyl, mercapto, nitro, thioalkoxy, dialkylamino, and dialkylaminosulfonyl;

$R_2$ and $R_3$ are hydrogen;

L is —$CH_2CH_2$—;

m is 1; and $R_4$ and $R_5$ are taken together to form a pyrrolidinyl ring of formula (a), wherein one of $R_7$, $R_8$, $R_9$, and $R_{10}$ is methyl and the remaining three substituents are hydrogen.

11. The compound of claim 1 selected from the group consisting of

4-{2-[2-(2-(R)-methyl-pyrrolidin-1-yl)-ethyl]-1H-indol-5-yl}-benzonitrile;

4-{1-Methyl-[2-(2-(R)-methyl-pyrrolidin-1-yl)-ethyl]-1H-indol-5-yl}-benzonitrile;

3-{1-Methyl-2-[2-(2-(R)-methyl-pyrrolidin-1-yl)-ethyl]-1H-indol-5-yl}-benzonitrile;

3-{2-[2-(2-(R)-Methyl-pyrrolidin-1-yl)-ethyl]-1H-indol-5-yl}-benzonitrile;

5-(4-Fluoro-phenyl)-2-[2-(2-(R)-methyl-pyrrolidin-1-yl)-ethyl]-1H-indole;

5-(3,5-Difluoro-phenyl)-2-[2-(2-(R)-methyl-pyrrolidin-1-yl)-ethyl]-1H-indole;

2-[2-(2-(R)-Methyl-pyrrolidin-1-yl)-ethyl]-5-(4-trifluoromethoxy-phenyl)-1H-indole;

2-[2-(2-(R)-Methyl-pyrrolidin-1-yl)-ethyl]-5-pyridin-3-yl-1H-indole;

1-(3-{2-[2-(2-(R)-Methyl-pyrrolidin-1-yl)-ethyl]-1H-indol-5-yl}-phenyl)-ethanone;

5-Furan-2-yl-2-[2-(2-(R)-methyl-pyrrolidin-1-yl)-ethyl]-1H-indole;

5-(2,6-Difluoro-pyridin-3-yl)-2-[2-(2-(R)-methyl-pyrrolidin-1-yl)-ethyl]-1H-indole;

5-(6-Methoxy-pyridin-3-yl)-2-[2-(2-(R)-methyl-pyrrolidin-1-yl)-ethyl]-1H-indole;

5-(4-Methanesulfonyl-phenyl)-2-[2-(2-(R)-methyl-pyrrolidin-1-yl)-ethyl]-1H-indole;

5-(2,6-Dimethyl-pyridin-3-yl)-2-[2-(2-(R)-methyl-pyrrolidin-1-yl)-ethyl]-1H-indole;

1-(4-{2-[2-(2-(R)-Methyl-pyrrolidin-1-yl)-ethyl]-1H-indol-5-yl}-phenyl)-ethanone;

5-(3-Fluoro-phenyl)-2-[2-(2-(R)-methyl-pyrrolidin-1-yl)-ethyl]-1H-indole;

Dimethyl-(4-{2-[2-(2-(R)-methyl-pyrrolidin-1-yl)-ethyl]-1H-indol-5-yl}-phenyl)-amine;

5-(4-Chloro-phenyl)-2-[2-(2-(R)-methyl-pyrrolidin-1-yl)-ethyl]-1H-indole;

5-(2,4-Dimethoxy-pyrimidin-5-yl)-2-[2-(2-(R)-methyl-pyrrolidin-1-yl)-ethyl]-1H-indole;

2-[2-(2-(R)-Methyl-pyrrolidin-1-yl)-ethyl]-5-(3-trifluoromethyl-phenyl)-1H-indole;

2-Methyl-5-{2-[2-(2-(R)-methyl-pyrrolidin-1-yl)-ethyl]-1H-indol-5-yl}-benzothiazole;

8-{2-[2-(2-(R)-Methyl-pyrrolidin-1-yl)-ethyl]-1H-indol-5-yl}-quinoline;

5-{2-[2-(2-(R)-Methyl-pyrrolidin-1-yl)-ethyl]-1H-indol-5-yl}-nicotinonitrile;

5-(5-Methoxy-pyridin-3-yl)-2-[2-(2-(R)-methyl-pyrrolidin-1-yl)-ethyl]-1H-indole;

5-(6-Fluoro-pyridin-3-yl)-2-[2-(2-(R)-methyl-pyrrolidin-1-yl)-ethyl]-1H-indole;

2-[2-(2-(R)-Methyl-pyrrolidin-1-yl)-ethyl]-5-pyrimidin-5-yl-1H-indole;

1-Methyl-2-[2-(2-(R)-methyl-pyrrolidin-1-yl)-ethyl]-5-pyridin-3-yl-1H-indole;

1-Methyl-2-[2-(2-(R)-methyl-pyrrolidin-1-yl)-ethyl]-5-pyrimidin-5-yl-1H-indole; and 5-{1-Methyl-2-[2-(2-(R)-methyl-pyrrolidin-1-yl)-ethyl]-1H-indol-5-yl}-nicotinonitrile.

12. A pharmaceutical composition comprising a therapeutically effective amount of a compound of claim 1 in combination with a pharmaceutically acceptable carrier.

* * * * *